US011364259B2

(12) United States Patent
Uchida et al.

(10) Patent No.: US 11,364,259 B2
(45) Date of Patent: Jun. 21, 2022

(54) MRNA FUNCTIONALIZATION METHOD

(71) Applicants: THE UNIVERSITY OF TOKYO, Tokyo (JP); KAWASAKI INSTITUTE OF INDUSTRIAL PROMOTION, Kawasaki (JP)

(72) Inventors: Satoshi Uchida, Tokyo (JP); Keiji Itaka, Tokyo (JP); Kazunori Kataoka, Tokyo (JP); Naoto Yoshinaga, Tokyo (JP)

(73) Assignees: THE UNIVERSITY OF TOKYO, Tokyo (JP); KAWASAKI INSTITUTE OF INDUSTRIAL PROMOTION, Kawasaki (JP)

( * ) Notice: Subject to any disclaimer, the term of this patent is extended or adjusted under 35 U.S.C. 154(b) by 366 days.

(21) Appl. No.: 16/473,535

(22) PCT Filed: Dec. 27, 2017

(86) PCT No.: PCT/JP2017/046906
§ 371 (c)(1),
(2) Date: Jun. 25, 2019

(87) PCT Pub. No.: WO2018/124181
PCT Pub. Date: Jul. 5, 2018

(65) Prior Publication Data
US 2019/0328769 A1    Oct. 31, 2019

(30) Foreign Application Priority Data

Dec. 27, 2016 (JP) ............................. JP2016-252487
Dec. 27, 2016 (JP) ............................. JP2016-252488

(51) Int. Cl.
*A61K 31/711* (2006.01)
*A61K 31/7115* (2006.01)
*A61K 47/69* (2017.01)
*A61K 39/00* (2006.01)
*C12N 15/117* (2010.01)

(52) U.S. Cl.
CPC ...... *A61K 31/7115* (2013.01); *A61K 39/0001* (2013.01); *A61K 39/0003* (2013.01); *A61K 39/0011* (2013.01); *A61K 47/6911* (2017.08); *C12N 15/117* (2013.01); *A61K 2039/53* (2013.01)

(58) Field of Classification Search
CPC ................................................. A61K 31/7115
See application file for complete search history.

(56) References Cited

U.S. PATENT DOCUMENTS

| | | |
|---|---|---|
| 2004/0110126 A1 | 6/2004 | Kukolj et al. |
| 2008/0176293 A1 | 7/2008 | Rohayem et al. |
| 2012/0190026 A1 | 7/2012 | Loeffert et al. |
| 2013/0211063 A1 | 8/2013 | Manoharan et al. |
| 2013/0317087 A1 | 11/2013 | Maquat et al. |
| 2015/0267192 A1 | 9/2015 | Heartlein et al. |
| 2017/0173182 A1 | 6/2017 | Kataoka et al. |

FOREIGN PATENT DOCUMENTS

| | | |
|---|---|---|
| JP | 2004-520839 A | 7/2004 |
| JP | 2007-513148 A | 5/2007 |
| JP | 2007-524373 A | 8/2007 |
| JP | 2010-540500 A | 12/2010 |
| JP | 2012-502074 A | 1/2012 |
| JP | WO2015/121924 A1 | 8/2015 |
| WO | WO 2004/078922 A2 | 9/2004 |
| WO | WO 2005/053600 A2 | 6/2005 |
| WO | WO 2009/040443 A1 | 4/2009 |
| WO | WO 2010/037539 A1 | 4/2010 |
| WO | WO 2015/051045 A2 | 4/2015 |

OTHER PUBLICATIONS

Ryskov et al. (Molecular Biology Reports 1 (1973) 215-219) (Year: 1973).*
Bacolla et al. (PLOS Genetics | DOI:10.1371/journal.pgen.1005696 Dec. 23, 2015) (Year: 2015).*
Rich, A. (2009). The Era of RNA Awakening: Structural biology of RNA in the early years. Quarterly Reviews of Biophysics, 42(2), 117-137. doi:10.1017/S0033583509004776 (Year: 2009).*
Extended European Search Report for European Application No. 17889018.2, dated Nov. 16, 2020.
Lächelt et al., "Nucleic Acid Therapeutics Using Polyplexes: A Journey of 50 Years {and Beyond)", Chemical Reviews, vol. 115, No. 19, Apr. 15, 2015, pp. 11043-11078.
Schlake et al. "Developing mRNA-vaccine technologies", RNA Biology. vol 9, No. 11. Nov. 1, 2012, pp. 1319-1330.
International Search Report for International Application No. PCT/JP2017/046906, dated Apr. 3, 2018.
Kallen et al., "A novel, disruptive vaccination technology," Human Vaccines & Immunotherapeutics, vol. 9, Issue 10, Jun. 4, 2013, pp. 2263-2276 (15 pages total).
Meis et al., "In Vitro Synthesis of 2'-Fluoro-Modified RNA Transcripts That Are Completely Resistant to RNase a Digestion Using the DuraScribe™ T7 Transcription Kit," EPICENTRE Forum, vol. 9, No. 1, 2002, pp. 10-11.
Uchida et al., "Designing immunostimulatory double stranded messenger RNA with maintained translational activity through hybridization with poly A sequences for effective vaccination," Biomaterials, vol. 150, 2018 (published online Sep. 27, 2017), pp. 162-170.
Uchida et al., "Systemic delivery of messenger RNA for the treatment of pancreatic cancer using polyplex nanomicelles with a cholrosterol moiety," Biomaterials, vol. 82, 2016 (published online Dec. 31, 2015), pp. 221-228.
Japanese Office Action, dated Jun. 30, 2020. for Japanese Application No. 2018-559579, with an English translation.
Office Action dated Dec. 21, 2021, in Japanese Patent Application No. 2020-180549.

* cited by examiner

Primary Examiner — Scott Long
(74) Attorney, Agent, or Firm — Birch, Stewart, Kolasch & Birch, LLP

(57) ABSTRACT

The present invention provides a functionalized mRNA including mRNA and double-stranded RNA including at least one RNA oligomer hybridized with mRNA. Functionalized mRNA is provided according to this configuration.

10 Claims, 42 Drawing Sheets

Specification includes a Sequence Listing.

Fig. 11
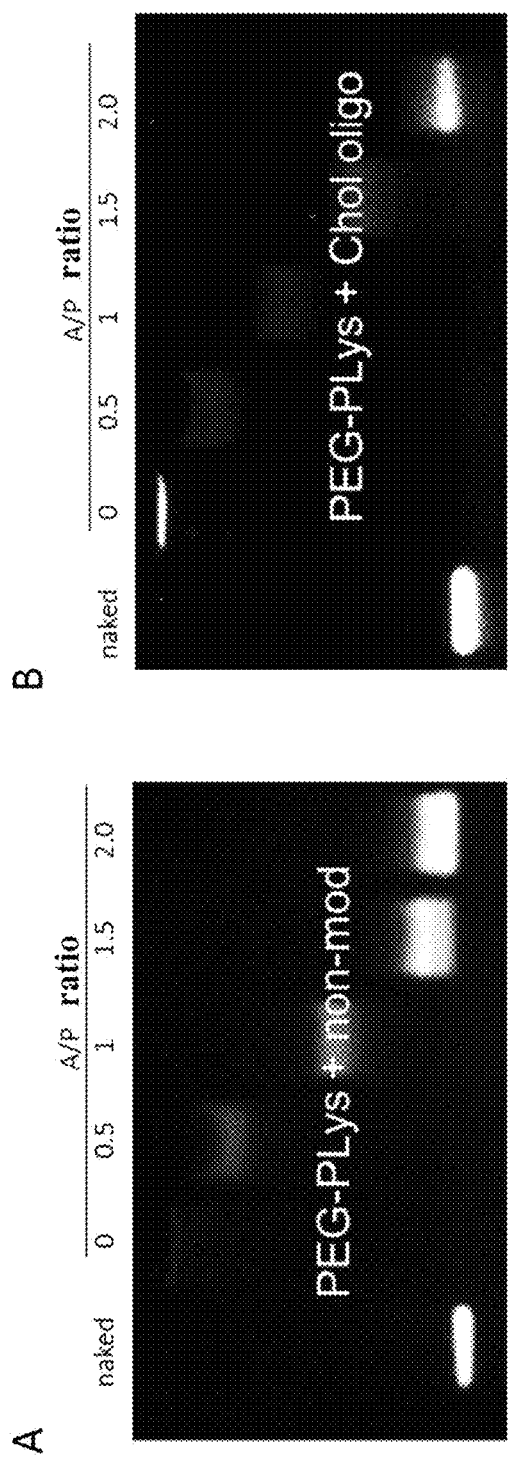
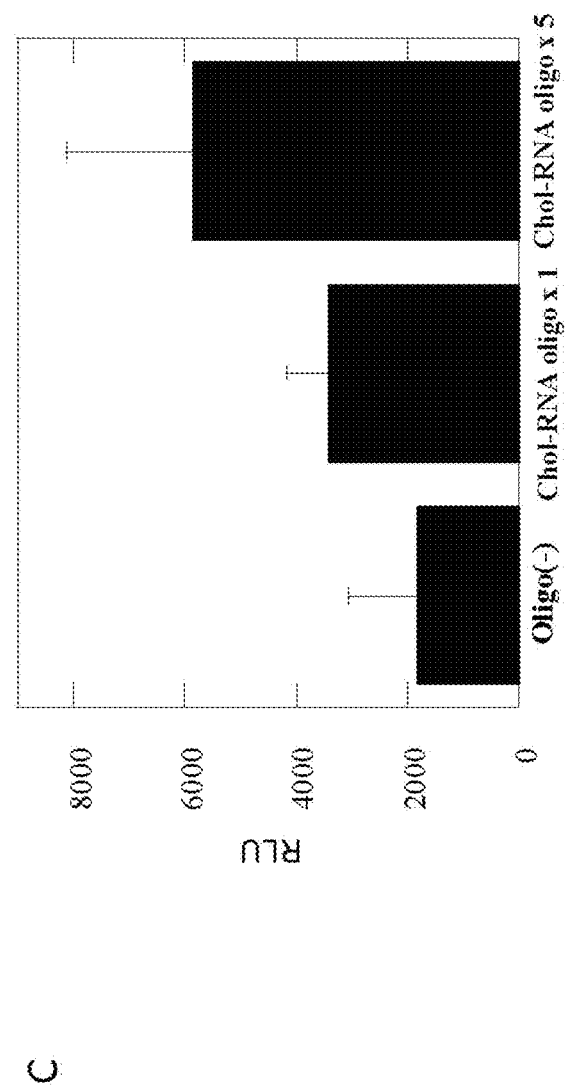

Fig. 14

Gluc sense strand (underline: open reading frame) (SEQ ID NO: 1)

```
GGGAGACCGGCCUGAGCAGUGAAGCUUGAGUACCGAGCUGGAUCCAGCCACCAU
GGGAGUCAAAGUUCUGUUUGCCCUGCAUCUGCCUGGGCCUGGGCCGAGGCCAAGCCC
ACGGAGAACAAGAAGAACUUCAACAUGUGGCCGAGCAACUUCGGACCACG
GAUCUCGAUGCUGACGGGAAGUUCCCGGAAGUGCAGAAGCUGCGUGGAGGUG
UCAAAGAGAUGGAAGCCCACAAGCUGGCACGGGCUGUCUGAUC
UGCCUGUCCACAAGUCACGCCAAGAUGAAGUUCAUCCAGGACGCUG
CCACCUAGAAGGGACAAAGAGUCACAGGCGCAUAGGGCGAGGGAUCG
UCGACAUUCCUGAGGUUCAAGGACACUGGGCCUCAAGGGCUUGCAU
ACGUGCAGAGCUUCUGAGCUCAGGUGGCCAACGUGUGGACCUU
UGCCAGCAAGAUCCAGGCCAUGCAAGAGGAUCCCGGGUGACUAA
GCGGCCGCUCGAGCAUGCAUCUAGAAAAAAAAAAAAAAAAAAAA
AAAAAAAAAAAAAAAAAAAAAAAAAAAAAAAAAAAAAAAAAAAAA
AAAAAAAAAAAAAAAAAAAAAAAAAAAAAAA
A
```

Fig. 15

Gluc coding sequence (SEQ ID NO: 32)

atgggagtcaaagttctgtttgccctgatctgcatcgctgttgccgaggccaagccaccgagaacaacgaagactt
caacatcgtggccgtggccagcaacttcgcgaccacgatctcgatgctgaccggaagttgcccggcaagaag
ctgccgctggagtgctcaaagagatggaagcaatgcccggaaagcaatgcccggaaagtcggtctgcaccaggagctgtctgatctgcc
tgtccacatcaagtgcacgccaagatgaagaagaagaagttcatccaggacgctgcacctacgaaggcgacaaaga
gtccgcacaggggcgggcataggcgaggcgatcgtcgatcattcctggttcaaggactggagccatgg
agcagttcatcgcacagtcgatctgtgttggactgcacaactggctgcctcaaaggcttgccacgtgcagtgtt
ctgacctgctcaagaagttggctgccgcaacgctgtgcgaccttgccagcaagatccaggcaggtggacaagat
caagggccggtggtgactaa

Fig. 16

Luc sense strand (underline: open reading frame) (SEQ ID NO: 33)

AUGGAAGACGCCAAAAACAUAAAGAAAGGCCCGGCGCCAUUCUAUCCGCUGGAAGAUGGAACCGCUG
GAGAGCAACUGCAUAAGGCUAUGAAGAGAUACGCCCUGGUUCCUGGAACAAUUGCUUUUACAGAUGC
ACAUAUCGAGGUGGACAUCACUUACGCUGAAGGUCUGAAAUGCCUUGGUUCUCAUUCUUAU
GCCCGUGUUGCGCUUCGUUAUUUAUGGCGUUAUACAGACAAACUCACGGCAUUUAUGAUGAACGU
GAAUUGCUCAACAGUAUGAACAUUUCGCAGCCUACCGUAGUGUUUGUGUUCCAAAAAGGGGUUGCAAA
AAAUUUUGAACGUGCAAAAAAAUUAGGCUCCCAAUCACCCCCAAUCAUGGAUUCUAAAAACGGAU
UACCAGGGAUUUCAGUCGAUGUACACGUUCGUCACAUCUCAUCUACCUCCCGGUUUUAAUGAAUACGA
UUUUGUGCCAGAGUCCUUCGAUAGGGACAAGACAAUUGCACUGAUCAUGAACUCCUCUGGAUCU
ACUGGGUUACCUAAGGGUGUGGCCCUUCCGCAUAGAACUGCCUGCGUGAGAUUCUCGCAUGCCAGAGAU
CCUAUUUUUGGCAAUCAAAUCAUUCCGGAUACUGCGAUUUUAAGUGUUGUUCCAUUCCAUCACGGUUUUG
GAAUGUUUACUACACUCGGAUAUUUGAUAUGUGGAUUGCGCUCAAGGAAUACCGAGAUCGU
CUCUCGCAAGGAAGCGAAGUCUCUCAUGGGCCCCUUGACAAUGACUAUCAAGAGGUUACCUCGCAUAUU
CCCGGGUAAUGGAUUCCAUCAACCGCAUCCCGCAAUAAUUCUCAACGGAUAAAUGAAGAUU
UCGCGGUAAUUCAACGAACACUUUUCAAGGAGUCAACCGCUACCAGGGGCAAUCUCUAAGAGCAAC
CUGAUACAGAAUCUCCUGAAACUUGUAAGGCACUCUAGAACGGAAAAAUCCUACGUAGGUCUU
GGUGAUGGGCGGAACGCCCAGGGCAAAUCUAACCCGGAAAGCAGUCGCACGGCCGCCUGCGCGAG
CUUCGACGGAUUGAACGAACUUGUUGACACCGGCGCUGUGAGUGCGUGUGAGUGAGUCCGGAGGAGCAGGAGGUGGA
ACUUUUUGUGGCAGAUGAACAUGGCCGAAAAAAGCAGAAGCUCCCCCGAAAAGGGCGGUAAA
CUCUUCGCCACACAGAUUCCUCCGCCCACCCCCUUCAUCCUUGCCAAGCCCCGGACAACCGAUCACCC
CCGACGGAAUACGGAUUGUACGAACCGACCGCGCCGCAGGUACGAGGCUUACCGCGACGGGCUUU
AAAGAGAGCGAGUUCGAGAUAGGCCACGGCGCCUUUUGGUCAAAGCUUCGAAGCGGUGAGGACAGG
CCCGGGUAAUGGGGCGGACAACUCCGGAAAAGUCGCUUACGGUAAA
AUAAAGGCCGGGAAGCGGAAGAUCGCCGUGUAA

Fig. 27

Gluc sense strand (SEQ ID NO: 51) (underline: open reading frame):
GGGAGAGACCGGCCUGAGCCUGAAGCUGAAGCUGAAGCUACCGAGCUCGGAUCCAGCCA
CCAUGGGAGUCAAAGUUCUGUUUGCCCUGAUCUGCAUCGCUGUGGCCGAGGC
CAAGCCCACCGAGAACAACGAAGACUUCAACAUCGUGGCCGUGGCCAGCAACUU
UCGGGACCACGGAUCUCGAUGCUGAAGAGAUGCCUGAAGCCAAGAAGCU
GCCGGCUGGAGGCUCUGUCUGCCUGUCCCACACAUCAAGGCCUGCAGAUGA
ACCAGGGCUGUCAUUCCAGGCGCUGGCGAGGCCACCUACGACCAAAGAGUCCGC
AGAAGUUCAUCCAGGCCCAUAGGCGAGGCGAUCGUCCUGACAUUCGAGAUUCCUGGGUUC
ACAGGGCCCACUGGCCUGGCUCAAGGCCUGCACGUUGCCACCUUUGCCAGAUCCAG
AAGGACUUGGACAAGAGGACAAGAUCAAGGGGGCGGUGACAUUUGCCGCCAUUAAGCCUGAG
CAUGUAGUCGGACAAGGAUCCCGGCGUACCCGGGCUGACGAAUUCAAAAAAAAAAAAAAAAAAAAAAAA
AAAAAAAAAAAAAAAAAAAAAAAAAAAAAAAAAAAAAA

Fig. 28

Gluc antisense strand (with poly U) (SEQ ID NO: 52):
GAACCAGAUCUCGUCUUUUUUUUUUUUUUUUUUUUUUUUUUU
UUUUUUUUUUUUUUUUUUUUUUUUUUUUUUGAAUCGAGCUACCCCG
GGAUCCUCUAGAUGCAUGCUCGAGCGGCCGCUUAGUCACCGGCCCUU
GAUCUUGCCACCUCUUGACCUGGAUCUGCAAAGGUCGCAAGCGUUGC
GGCAGCAGCCAGAACACUGCAGAACACUGCACCUGCAAGCCCUUUGA
GGCAGCCAGUUGCAGUCCAGUCCUUGACCUGCGAUCGAACUGCUC
CAUGGGCUCCAAGUCCCUUGAACCCAGGAAUCUCAGGAAUGCGAUCGCC
UCGCCUAUGCCGGCCGGGACUCUUGUCGCCUUGAGGUGUGGCAGC
GUCCUGGGAUGAACUUCACUUGGGCACUUGGGACACAGGCA
GAUCAGACAGCCCGGCCAGCGCCUUUCGGCAUUGGCCUUCCAUCUCU
UUGAGCACCUCCAGCGGCGCCAGCUUGCCCGGCAACCGGUCAGCAU
CGAGACCUCGGGGUCCGCGAAGUUGCCACCGAUGCCAGUUGAGUCUUC
GUUGUUCUCCAUGGGCUGGAUCCGGACCAGCCACAGGCCAAAC
AGAACUUUGACUCCCAUGGCCUGGACUCCGAGCUCGGUACCAAGCU

Fig. 29

Gluc antisense strand (without poly U) (SEQ ID NO: 53):
GAACCAGAUCUGAUAUCAUCGAUGAAUUCGAGCUACCCGGGGAUCCUCUAGA
UGCAUGCUCGAGCGGCCGCCUUAGUCACCACCCCUUGAUCUGUCCACCUGG
CCCUGGAUCUUGCCUGGCAAAGGUCCACAGGCCAGCAGCAGCCAGCCUUUGAGCAG
GUCAGAACACUGACCUGCAAGCCCUUUGAGGCAGUUGCAGUCCACAC
ACAGACCCUGCGAUGAACUCGAUGGCUCCAAGCCUUGAACCCAGGA
AUCUCAGGAAUGUCGACAUCGCCCUAUGCCCUGCGGACUCUUUGUC
GCCUUCGUAGGUGUGGCCAGCGUCCUGGAUGAACUUCUUCAUCGGGCGUCCACU
UGAGUGGGACAGGACAGAUCAGAACAGCUCCAGCAGCCUUUCCGGCCAUUG
GCUUCCAUCUCUUUGAGCACCUCCAGCGUCCGCAAGUUGUGGCCCAACUUCCCCGCG
GUCAGCAUCGAGAUCGGCCUGCUUGCCAAGUUGGCCACGAGCCAGAUCAGGUUGAAGU
CUUCGUUGUUCCGGGCUUGGCCUGGAUCCGCAGCAGCGAUCAGGCAAAC
AGAACUUUGACUCCCAUGGCCUGGAUCCGCAGCCUCGGCUACCAAGCU

Fig. 30 poly U (SEQ ID NO: 54):
GAACCAGAUCUCGUCUCUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUGAAUCGAGCUCGGUACCC

Fig. 31

OVA sense strand (SEQ ID NO: 55) (underline: open reading frame):
GGGAGACCGGCCUCGAGAUGGCAGCAUCCGGAGCAAGCGGGCCAGCAAGCAUGGAGUUUUGUUUUGACCGU
GUUUAAGGAACUGAAGUCACGGCAUCACGCUAAUGAGAAUAUCUCUACUGCCCAUCGCCAUUA
UGUCCUGCCCUGGCUAUGGGCUAUCUCCCGGGAGCUAAGGACCAGAACAGAAUCAACAAG
GUGGUCCGCUUCGACAAACUGGGCGAGCAUGGACACAGCAUGCAGUGGCACUUC
CGUGAAUGUCCACAAGUCCCUGAGGACACCUGAUGACCAGCCUAAUGACGUGU
ACUCUCUCUGCCCUCCCGGGCCUGAGGACUGUACGCCGAGAAGGUAUCCCUCGAGUAC
CUGCAGUGGGUGAAAGAACUGUAUAGGGCGGACUGGAGCCAACUCAACUUUCAGACAGCCGC
UGACCAGGCCAGAGAACUACUGCAUUAAUGUGUGGAGAGUCAAGGUGCACUAACGGUAUCAUCCGCA
AUGUGCUGGCAGCCCUCUAGGCAUGCCGAUGUAGCCAGAGACGAAGCCCAUUCAGGCGAGU
UUCAAGGCGUGUGGGAGAAGCAAACCGUCAGAUGUAUCAGAUCGCCUGUUCAGAGUGGCUA
GACAGAGGAUCCAUCCGAGAAGAUGAACUGGAACUGCCCUUUGCCUCAGAACCAUGAGCAUG
GCAUGGCUGCUUAAGAGAUGGACCUGCCGGAAUCAGUGAAAGAAUCAACAAAGUCUACCUGC
CUGGGAUGACUGAAUGGAGGAAGAACCAUCAAGCAAAGAAUCAACAAAGUCUACCUGC
GAAGCUGAAUGGAACCUCAAGCAAUAUAACCUGAAAAAACCUGAAGCUAUGGGCUAUACA
CUCGGGACUCUUUCCUCUCGUGGCCAAUCUGCUGCCAUCAGCCGAGUCCCUGAAGAUUC
GAUGUCGUUUCCUCUCGUGGCCAAUCGCAGAGAUCAAUGAAGCCCGAGUCCCUGAAGAUUUC
UCAAGCCAGCACGGGGUCCUGCAGCCCAGCUCACAAUGAAGCCCGAGUCCCUGAAGCGGAUCU
GCAAGGCGGGUCAUCAACAACGCCGAGUGCAGAGAGCAGCCGAGUUCCGGCCAUCCAUUUC
UGUUCUGUAACAACAUAGCCACAAUGCCCACAAGCCGUAGAUGCCGUGCACCA
UGAAAUUCAAAAAAAAAAAAAAAAAAAAAAAAAAAAAAAAAAAAAAAAA
AA

Fig. 32 poly U (SEQ ID NO: 56)
GAACCAGAUCUCGUCUCUCUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUGAAUU

Fig. 33

Gluc coding sequence (SEQ ID NO: 57)
atgggagtcaaagttctgttgcctgatctgcatcgctgctggccgaggccaagcccaccgagaacacgaagaactcaacatcgtgccgtg
gccagcaacttcgcgaccacgatctcgatgtgctgaccggagaagtgcccgcaagagtgcccgaggtgctcaaagagatggaag
ccaatgcccggaaagctggctgcaccagggctgatctgcctgtccacatcaagtgcacgcccaagatgaagttcatcccaggac
gctgccactacctacgaaggcgacaagagtccgcacaggacggcatagggcgaggcgatgtcgacattcctgatccctgggttcaagga
cttggagcccatggagagcagtgagagcagtcatcgacacggttgtgtggactgcacaactggcctcaaaggccttgccaactgcagtgtct
gacctgctcaagagaagtggctgccgcaacgctgtgcgaccttgccagcaagatccaggggcaagatcaaggggcgctgggtg
actaa

Fig. 34

OVA coding sequence (SEQ ID NO: 58)
atgggcagcatcggggcagcaagcatggagtttgttgacgtgtttaaggaactgaaagtgcatcacgctaatgaaatatcttctactgcc
catgccattatgtcctgctatggtgtatctggagctaaggacgtaaggacacagacaacaaggtgtccgctcgacaaactg
cccggtttggcgacagcattgaggctcagtgtggcacttccgtgaatgtcctgaggacatctcgaaccagattaccaagccta
atgacgtgtactcctctctggcctcccggctgagctgagcatccatgcctgagtacctgagtgctgaaagaactgtat
agggcgggactgctgcagccaatcaactccagacagccgctgaccaggccctctgcaatgattaattcttggtggaagtcagtacttaacggtat
cattcgcaatgtgctgcagccctctagtgtgcgatagccagatgtgtgtgttcaaccaatcgtccaagatgtatcagagcctgtcag
ttcaaggaagatactcaaggcatccgagtgcagacaggcaggaaagcaaaccgtccagatgatgtatcgatcggcctgttcag
agtgctagcatcgagagatgaaaatcatttggaactgctttgctctgaaccatgagcatgcttgtgtgctcgcagagcgaggt
cagtgggctggagcagctggagaatgaagatggaagaaaaatcattaacttcgagaagatgaccaagcaatgatggaggaacgaaagatcaaa
gtctacctgctcggaatcccagccatcgagcagatggcatacagatgccgctatgggctatgatgctattactccgtgatgttccttcctcttaggccaat
ctgtcttggccatctcaaggccgccgagtcctgaagattctcaggcagtcacgcagcagagagatcaatgaaccatgcaggcgcgaggtggtc
ggatctgcgaaagccgggggtggagtcaaggtgtccagaggagttccgggccgatcatccattcgtctgtatcaaacatattgccacaa
atgccgtgctgttcttcggtagatgcgtgtcaccatga

Fig. 36

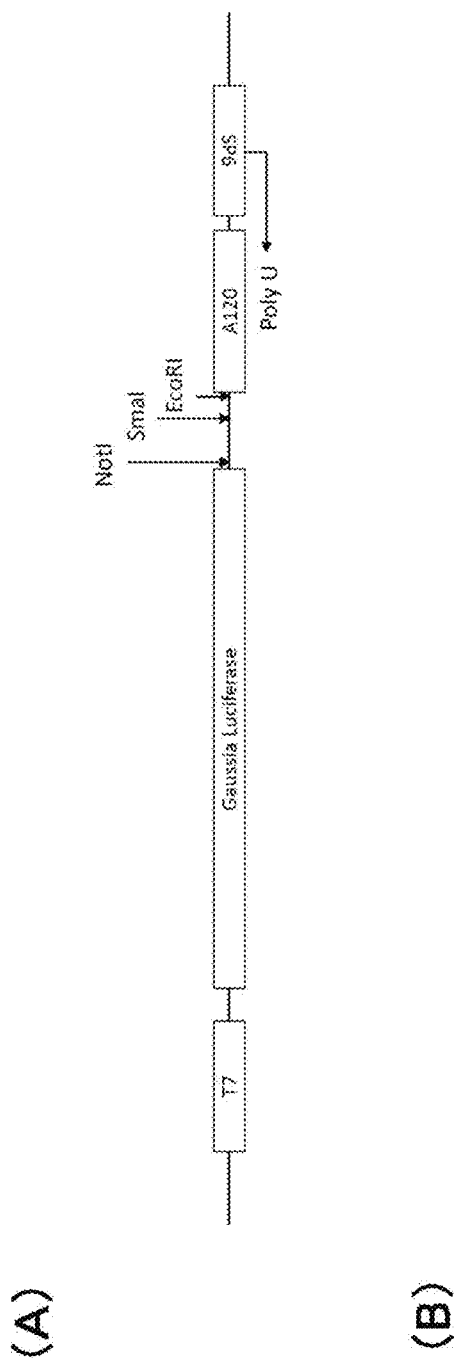

(B)

poly U produced by cleavage with EcoRI (chain length of sequence complementary to 3' UTR: 5 nucleotides)
(SEQ ID NO: 56)
GAACCAGAUCUCGUCUCUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUGAAUU poly U produced by cleavage with SmaI (chain length of sequence complementary to 3' UTR: 19 nucleotides)
(SEQ ID NO: 54)
GAACCAGAUCUCGUCUCUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUGAAUUCGAGCUCGGUACCC poly U produced by cleavage with NotI (chain length of sequence complementary to 3' UTR: 50 nucleotides)
(SEQ ID NO: 59)
GAACCAGAUCUCGUCUCUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUUGAAUUCGAGCUCGGUACCCGGGGAUCCUCUAGAUGCAUGCUCGAGCGGCC

Fig. 41

Vector sequence (SEQ ID NO: 65) (underline: DNA sequence encoding second RNA sequence; italic: T7 promoter):
TGGGCCTTTCTTCGGTAGAAATCAAGGATCTTCTTGAGATCCTTTTTTCTGCGCGTAATCTGCTGCT
TGCAAACAAAAAAACCACCGCTACCAGCGGTGGTTTGTTTGCCGGATCAAGAGCTACCAACTCTTTTTC
CGAGGTAACTGGCTTCAGCAGAGCGCAGATACCAAATACTGTTCTTCTAGTGTAGCCGTAGTTAGGCCAC
CACTTCAAGAACTCTGTAGCACCGCCTACATACCTCGCTCTGCTAATCCTGTTACCAGTGGCTGCTGCCA
GTGGCGATAAGTCGTGTCTTACCGGGTTGGACTCAAGACGATAGTTACCGGATAAGGCGCAGCGGTCGG
GCTGAACGGGGGGTTCGTGCACACAGCCCAGCTTGGAGCGAACGACCTACACCGAACTGAGATACCTA
CAGCGTGAGCTATGAGAAAGCGCCACGCTTCCCGAAGGGAGAAAGGCGGACAGGTATCCGGTAAGCGG
CAGGGTCGGAACAGGAGAGCGCACGAGGGAGCTTCCAGGGGGAAACGCCTGGTATCTTTATAGTCCTG
TCGGGTTTCGCCACCTCTGACTTGAGCATCGATTTTTGTGATGCTCGTCAGGGGGGCGGAGCCTATGGA
AAAACGCCAGCAACGCGGCCTTTTTACGGTTCCTGGCCTTTTGCTGGCCTTTTGCTCACATGTTCTTTCCT
GCGTTATCCCCTGATTCTGTGGATAACCGTATTACCGCCTTTGAGTGAGCTGATACCGCTCGCCGCAGC
CGAACGACCGAGCGCAGCGAGTCAGTGAGCGAGGAAGCGGAAGAGCGCCCAATACGCAAACCGCCTCTC
CCCGCGCGTTGGCCGATTCATTAATGCAGCTGGCACGACAGGTTTCCCGACTGGAAAGCGGGCAGTGA
GCGCAACGCAATTAATGTGAGTTAGCTCACTCATTAGGCACCCCAGGCTTTACACTTTATGCTTCCGGCTCG
TATGTTGTGTGGAATTGTGAGCGGATAACAATTTCACACAGGAAACAGCTATGACCATGATTACGAATTCGA
GCTCGGTACCCGGGGATCCTCTAGAGTCGACCTGCAGGCATGCAAGCTTGGCGTAATCATGGTCATAGCTG
TTTCCTGTGTGAAATTGTTATCCGCTCACAATTCCACACAACATACGAGCCGGAAGCATAAAGTGTAAAGCC
TGGGGTGCCTAATGAGTGAGCTAACTCACATTAATTGCGTTGCGCTCACTGCCCGCTTTCCAGTCGGGAAA
CCTGTCGTGCCAGCTGCATTAATGAATCGGCCAACGCGCGGGGAGAGGCGGTTTGCGTATTGGGCGC
TCTTCCGCTTCCTCGCTCACTGACTCGCTGCGCTCGGTCGTTCGGCTGCGGCGAGCGGTATCAGCTCA
CTCAAAGGCGGTAATACGGTTATCCACAGAATCAGGGGATAACGCAGGAAAGAACATGTGAGCAAAAGGCCA
GCAAAAGGCCAGGAACCGTAAAAAGGCCGCGTTGCTGGCGTTTTTCCATAGGCTCCGCCCCCCTGACGA
GCATCACAAAAATCGACGCTCAAGTCAGAGGTGGCGAAACCCGACAGGACTATAAAGATACCAGGCGT
TTCCCCCTGGAAGCTCCCTCGTGCGCTCTCCTGTTCCGACCCTGCCGCTTACCGGATACCTGTCCGCCTTTCT
CCCTTCGGGAAGCGTGGCGCTTTCTCATAGCTCACGCTGTAGGTATCTCAGTTCGGTGTAGGTCGTTCG
CTCCAAGCTGGGCTGTGTGCACGAACCCCCCGTTCAGCCCGACCGCTGCGCCTTATCCGGTAACTATCGTC
TTGAGTCCAACCCGGTAAGACACGACTTATCGCCACTGGCAGCAGCCACTGGTAACAGGATTAGCAGA
GCGAGGTATGTAGGCGGTGCTACAGAGTTCTTGAAGTGGTGGCCTAACTACGGCTACACTAGAAGAA
CAGTATTTGGTATCTGCGCTCTGCTGAAGCCAGTTACCTTCGGAAAAAGAGTTGGTAGCTCTTGATCC
GGCAAACAAACCACCGCTGGTAGCGGTGGTTTTTTTGTTTGCAAGCAGCAGATTACGCGCAGAAAAAA
AGGATCTCAAGAAGATCCTTTGATCTTTTCTACGGGGTCTGACGCTCAGTGGAACGAAAACTCACGT
TAAGGGATTTTGGTCATGAGATTATCAAAAAGGATCTTCACCTAGATCCTTTTAAATTAAAAATGAAGTTT
TAAATCAATCTAAAGTATATATGAGTAAACTTGGTCTGACAGTTACCAATGCTTAATCAGTGAGGCACCTA
TCTCAGCGATCTGTCTATTTCGTTCATCCATAGTTGCCTGACTCCCCGTCGTGTAGATAACTACGATACG
GGAGGGCTTACCATCTGGCCCCAGTGCTGCAATGATACCGCGAGACCCACGCTCACCGGCTCCAGATT
TATCAGCAATAAACCAGCCAGCCGGAAGGGCCGAGCGCAGAAGTGGTCCTGCAACTTTATCCGCCTCC
ATCCAGTCTATTAATTGTTGCCGGGAAGCTAGAGTAAGTAGTTCGCCAGTTAATAGTTTGCGCAACGTTGTT
GCCATTGCTACAGGCATCGTGGTGTCACGCTCGTCGTTTGGTATGGCTTCATTCAGCTCCGGTTCCCAACG
ATCAAGGCGAGTTACATGATCCCCCATGTTGTGCAAAAAAGCGGTTAGCTCCTTCGGTCCTCCGATCGT
TGTCAGAAGTAAGTTGGCCGCAGTGTTATCACTCATGGTTATGGCAGCACTGCATAATTCTCTTACTGTCA
TGCCATCCGTAAGATGCTTTTCTGTGACTGGTGAGTACTCAACCAAGTCATTCTGAGAATAGTGTATGCGG
CGACCGAGTTGCTCTTGCCCGGCGTCAATACGGGATAATACCGCGCCACATAGCAGAACTTTAAAAGTG
CTCATCATTGGAAAACGTTCTTCGGGGCGAAAACTCTCAAGGATCTTACCGCTGTTGAGATCCAGTTCG
ATGTAACCCACTCGTGCACCCAACTGATCTTCAGCATCTTTTACTTTCACCAGCGTTTCTGGGTGAGCAAAA
ACAGGAAGGCAAAATGCCGCAAAAAAGGGAATAAGGGCGACACGGAAATGTTGAATACTCATACTCT
TCCTTTTTCAATATTATTGAAGCATTTATCAGGGTTATTGTCTCATGAGCGGATACATATTTGAATGTATTT
AGAAAAATAAACAAATAGGGGTTCCGCGCACATTTCCCCGAAAAGTGCCACCTGACGTCTAAGAAACCA
TTATTATCATGACATTAACCTATAAAAATAGGCGTATCACGAGGCCCTTTCGTCTTCAAGAA*TTCTCATGT*
*TTGACAGCTTATCATCGAT*ATCAAGCTTCGACGAGGAGCCCTCAGCCTCAGTCGATCTGCTGGATCAT
GGTCGGAATCTGGATCAAGTCAAGCTAGAATCAGTCGACTAGATAAACTGGCCGTGATCAACTCACTACTGGATCCAT
CCGGTCCGCATATCATTCAAGGACCTAGAATCAGCTGACTAAACTGGAAGCTAGTTGAAAAAGTGGACCTAGATGT
CTTGCCAGCGATCACTGGTGCTTCAGCCGTAACTGGCACTAGATTGGCAGATTATCGTCAACTAGATAGA
GAAGCGATCAGAGAGCAGCAGCCCAGCCAGTCCAGCCAGCATCAAGCTAGTTATCAGGCGAGATCAGGAGAT
GCCTAGAATAGCGCCTAGCGAGCGAGGACCGAGGACGAGGACAGGCCATCAATAAGGCTAGTTAACCGGGG
AAAAAGCTCCACCGCTAGCGTATTAACTGCTACGTATATAGGTTGAATGTCGCCCGTCTAAGTACTAGA
GCTAGAATAATGCCTAGCGAAACAGCCTATATAACGCCTGATATCAAAGTGACTCAAGCCTGACCCGGAT
TAAAAAGCTTGAGGCGTAACGAATCAGCTAAATACGTCTGATGTCAGCATGATCTGTCCCCTCCCGGCC
GGCTCCGGATATCATTCAAGGACGATCAGCTGCTGAGTCTCCAGCACTGCACTGAGCTAACTGCAGGGGATCT
CTTTAAAAGCTTGATGCGATCAAGGACGATCAGCAAGCTAGAATCAGCGTAACGAATCAACTCACTCGGG
GGTCGGACATCAACCAGACTAGAATCAAGCTGACTAGATAACTGGCCGTCGTTTTACAACGTCGTGACTGGG
CTTCCGGGCGATCAGGCAGTCGAGGAGATCAAGCTAGATAGAATCAAAAAACTGGCGTAACGTCGTGACTGGG

```
                              SEQUENCE LISTING

<160> NUMBER OF SEQ ID NOS: 68

<210> SEQ ID NO 1
<211> LENGTH: 783
<212> TYPE: RNA
<213> ORGANISM: Artificial sequence
<220> FEATURE:
<223> OTHER INFORMATION: synthetic RNA

<400> SEQUENCE: 1
gggagaccgg ccucgagcag cugaagcuug guaccgagcu cggauccagc caccauggga        60 gucaaguuc uguuugcccu gaucugcauc gcuguggccg aggccaagcc caccgagaac       120
aacgaagacu ucaacaucgu ggccguggcc agcaacuucg cgaccacgga ucucgaugcu       180
gaccgcggga aguugcccgg caagaagcug ccgcuggagg ugcucaaaga gauggaagcc       240
aaugcccgga aagcuggcug caccagggge ugucugaucu gccuguccca caucaagugc       300
acgcccaaga ugaagaaguu caucccagga cgcugccaca ccuacgaagg cgacaaagag       360
uccgcacagg gcggcauagg cgaggcgauc gucgacauuc cugagauucc uggguucaag       420
gacuuggagc ccauggagca guucaucgca caggucgauc ugugugugga cugcacaacu       480
ggcugccuca aagggcuugc caacgugcag uguucugacc ugcucaagaa guggcugccg       540
caacgcugug cgaccuuugc cagcaagauc cagggccagg uggacaagau caagggggcc       600
gguggugacu aagcggccgc ucgagcaugc aucuagagga uccccgggua ccgagcucga       660
auucaaaaaa aaaaaaaaaa aaaaaaaaaa aaaaaaaaaa aaaaaaaaaa aaaaaaaaaa       720
aaaaaaaaaa aaaaaaaaaa aaaaaaaaaa aaaaaaaaaa aaaaaaaaaa aaaaaaaaaa       780
aaa                                                                   783
```

```
<210> SEQ ID NO 2
<211> LENGTH: 17
<212> TYPE: RNA
<213> ORGANISM: Artificial sequence
<220> FEATURE:
<223> OTHER INFORMATION: synthetic RNA

<400> SEQUENCE: 2
ucuuugagca ccuccag                                                    17

<210> SEQ ID NO 3
<211> LENGTH: 17
<212> TYPE: RNA
<213> ORGANISM: Artificial sequence
<220> FEATURE:
<223> OTHER INFORMATION: synthetic RNA

<400> SEQUENCE: 3
cucuagaugc augcucg                                                    17

<210> SEQ ID NO 4
<211> LENGTH: 17
<212> TYPE: RNA
<213> ORGANISM: Artificial sequence
<220> FEATURE:
<223> OTHER INFORMATION: synthetic RNA

<400> SEQUENCE: 4
cucggccaca gcgaugc                                                    17

<210> SEQ ID NO 5
<211> LENGTH: 17
<212> TYPE: RNA
<213> ORGANISM: Artificial sequence
<220> FEATURE:
<223> OTHER INFORMATION: synthetic RNA

<400> SEQUENCE: 5
gcggcagcca cuucuug                                                    17

<210> SEQ ID NO 6
<211> LENGTH: 17
<212> TYPE: RNA
<213> ORGANISM: Artificial sequence
<220> FEATURE:
<223> OTHER INFORMATION: synthetic RNA

<400> SEQUENCE: 6
aucucaggaa ugucgac                                                    17

<210> SEQ ID NO 7
<211> LENGTH: 23
<212> TYPE: RNA
<213> ORGANISM: Artificial sequence
<220> FEATURE:
<223> OTHER INFORMATION: synthetic RNA

<400> SEQUENCE: 7
uccaucucuu ugagcaccuc cag                                             23

<210> SEQ ID NO 8
<211> LENGTH: 40
<212> TYPE: RNA
<213> ORGANISM: Artificial sequence
<220> FEATURE:
<223> OTHER INFORMATION: synthetic RNA
```

<400> SEQUENCE: 8
cuuuccgggc auuggcuucc aucucuuuga gcaccuccag                                40

<210> SEQ ID NO 9
<211> LENGTH: 60
<212> TYPE: RNA
<213> ORGANISM: Artificial sequence
<220> FEATURE:
<223> OTHER INFORMATION: synthetic RNA

<400> SEQUENCE: 9
acagccccug gugcagccag cuuuccgggc auuggcuucc aucucuuuga gcaccuccag          60

<210> SEQ ID NO 10
<211> LENGTH: 19
<212> TYPE: RNA
<213> ORGANISM: Artificial sequence
<220> FEATURE:
<223> OTHER INFORMATION: synthetic RNA

<400> SEQUENCE: 10
aaucuuugag caccuccag                                                      19

<210> SEQ ID NO 11
<211> LENGTH: 22
<212> TYPE: RNA
<213> ORGANISM: Artificial sequence
<220> FEATURE:
<223> OTHER INFORMATION: synthetic RNA

<400> SEQUENCE: 11
aauaaucuuu gagcaccucc ag                                                  22

<210> SEQ ID NO 12
<211> LENGTH: 19
<212> TYPE: RNA
<213> ORGANISM: Artificial sequence
<220> FEATURE:
<223> OTHER INFORMATION: synthetic RNA

<400> SEQUENCE: 12
aacucuagau gcaugcucg                                                      19

<210> SEQ ID NO 13
<211> LENGTH: 22
<212> TYPE: RNA
<213> ORGANISM: Artificial sequence
<220> FEATURE:
<223> OTHER INFORMATION: synthetic RNA

<400> SEQUENCE: 13
aauaacucua gaugcaugcu cg                                                  22

<210> SEQ ID NO 14
<211> LENGTH: 19
<212> TYPE: RNA
<213> ORGANISM: Artificial sequence
<220> FEATURE:
<223> OTHER INFORMATION: synthetic RNA

<400> SEQUENCE: 14
aacucggcca cagcgaugc                                                      19

```
<210> SEQ ID NO 15
<211> LENGTH: 19
<212> TYPE: RNA
<213> ORGANISM: Artificial sequence
<220> FEATURE:
<223> OTHER INFORMATION: synthetic RNA

<400> SEQUENCE: 15
aagcggcagc cacuucuug                                                       19

<210> SEQ ID NO 16
<211> LENGTH: 19
<212> TYPE: RNA
<213> ORGANISM: Artificial sequence
<220> FEATURE:
<223> OTHER INFORMATION: synthetic RNA

<400> SEQUENCE: 16
auaucucagg aaugucgac                                                       19

<210> SEQ ID NO 17
<211> LENGTH: 19
<212> TYPE: RNA
<213> ORGANISM: Artificial sequence
<220> FEATURE:
<223> OTHER INFORMATION: synthetic RNA

<400> SEQUENCE: 17
aagcagccag cuuucccgg                                                       19

<210> SEQ ID NO 18
<211> LENGTH: 19
<212> TYPE: RNA
<213> ORGANISM: Artificial sequence
<220> FEATURE:
<223> OTHER INFORMATION: synthetic RNA

<400> SEQUENCE: 18
aaacucuuug ucgccuucg                                                       19

<210> SEQ ID NO 19
<211> LENGTH: 19
<212> TYPE: RNA
<213> ORGANISM: Artificial sequence
<220> FEATURE:
<223> OTHER INFORMATION: synthetic RNA

<400> SEQUENCE: 19
aauugaggca gccaguugu                                                       19

<210> SEQ ID NO 20
<211> LENGTH: 19
<212> TYPE: RNA
<213> ORGANISM: Artificial sequence
<220> FEATURE:
<223> OTHER INFORMATION: synthetic RNA

<400> SEQUENCE: 20
uagugggaca ggcagauca                                                       19

<210> SEQ ID NO 21
<211> LENGTH: 19
<212> TYPE: RNA
<213> ORGANISM: Artificial sequence
<220> FEATURE:
<223> OTHER INFORMATION: synthetic RNA
```

<400> SEQUENCE: 21
aauugaaguc uucguuguu                                                  19

<210> SEQ ID NO 22
<211> LENGTH: 19
<212> TYPE: RNA
<213> ORGANISM: Artificial sequence
<220> FEATURE:
<223> OTHER INFORMATION: synthetic RNA

<400> SEQUENCE: 22
aauuuuuuuu uuuuuuuuu                                                  19

<210> SEQ ID NO 23
<211> LENGTH: 19
<212> TYPE: RNA
<213> ORGANISM: Artificial sequence
<220> FEATURE:
<223> OTHER INFORMATION: synthetic RNA

<400> SEQUENCE: 23
ucuuugagca ccuccagau                                                  19

<210> SEQ ID NO 24
<211> LENGTH: 19
<212> TYPE: RNA
<213> ORGANISM: Artificial sequence
<220> FEATURE:
<223> OTHER INFORMATION: synthetic RNA

<400> SEQUENCE: 24
aaaaaaaaaa aaaaaaaaa                                                  19

<210> SEQ ID NO 25
<211> LENGTH: 17
<212> TYPE: RNA
<213> ORGANISM: Artificial sequence
<220> FEATURE:
<223> OTHER INFORMATION: synthetic RNA

<400> SEQUENCE: 25
ucgaaguacu cagcgua                                                    17

<210> SEQ ID NO 26
<211> LENGTH: 19
<212> TYPE: RNA
<213> ORGANISM: Artificial sequence
<220> FEATURE:
<223> OTHER INFORMATION: synthetic RNA

<400> SEQUENCE: 26
aaucgaagua cucagcgua                                                  19

<210> SEQ ID NO 27
<211> LENGTH: 17
<212> TYPE: RNA
<213> ORGANISM: Artificial sequence
<220> FEATURE:
<223> OTHER INFORMATION: synthetic RNA

<400> SEQUENCE: 27
ucuuugagca ccuccag                                                    17

```
<210> SEQ ID NO 28
<211> LENGTH: 21
<212> TYPE: DNA
<213> ORGANISM: Artificial sequence
<220> FEATURE:
<223> OTHER INFORMATION: synthetic DNA/RNA

<400> SEQUENCE: 28
cuuacgcuga guacuucgat t                                              21

<210> SEQ ID NO 29
<211> LENGTH: 21
<212> TYPE: DNA
<213> ORGANISM: Artificial sequence
<220> FEATURE:
<223> OTHER INFORMATION: synthetic DNA/RNA

<400> SEQUENCE: 29
ucgaaguacu cagcguaagt t                                              21

<210> SEQ ID NO 30
<211> LENGTH: 21
<212> TYPE: DNA
<213> ORGANISM: Artificial sequence
<220> FEATURE:
<223> OTHER INFORMATION: synthetic DNA/RNA

<400> SEQUENCE: 30
uucuccgaac gugucacgut t                                              21

<210> SEQ ID NO 31
<211> LENGTH: 21
<212> TYPE: DNA
<213> ORGANISM: Artificial sequence
<220> FEATURE:
<223> OTHER INFORMATION: synthetic DNA/RNA

<400> SEQUENCE: 31
acgugacacg uucggagaat t                                              21

<210> SEQ ID NO 32
<211> LENGTH: 558
<212> TYPE: DNA
<213> ORGANISM: Artificial sequence
<220> FEATURE:
<223> OTHER INFORMATION: synthetic DNA

<400> SEQUENCE: 32
atgggagtca agttctgtt tgccctgatc tgcatcgctg tggccgaggc caagcccacc      60
gagaacaacg aagacttcaa catcgtggcc gtggccagca acttcgcgac cacggatctc    120
gatgctgacc gcgggaagtt gcccggcaag aagctgccgc tggaggtgct caaagagatg    180
gaagccaatg cccggaaagc tggctgcacc aggggctgtc tgatctgcct gtcccacatc    240
aagtgcacgc ccaagatgaa gaagttcatc ccaggacgct gccacaccta cgaaggcgac    300
aaagagtccg cacagggcgg catagccgag gcgatcgtcg acattcctga gattcctggg    360
ttcaaggact tggagcccat ggagcagttc atcgcacagg tcgatctgtg tgtggactgc    420
acaactggct gcctcaaagg gcttgccaac gtgcagtgtt ctgacctgct caagaagtgg    480
ctgccgcaac gctgtgcgac cttttgccagc aagatccagg gccaggtgga caagatcaag    540
ggggccggtg gtgactaa                                                 558
```

<210> SEQ ID NO 33
<211> LENGTH: 1653
<212> TYPE: RNA
<213> ORGANISM: Artificial sequence
<220> FEATURE:
<223> OTHER INFORMATION: synthetic RNA

<400> SEQUENCE: 33

| | | | | | |
|---|---|---|---|---|---|
| auggaagacg | ccaaaaacau | aaagaaaggc | ccggcgccau | ucuauccgcu | ggaagaugga | 60 |
| accgcuggag | agcaacugca | uaaggcuaug | aagagauacg | cccugguucc | uggaacaauu | 120 |
| gcuuuuacag | augcacauau | cgaggugggac | aucacuuacg | cugaguacuu | cgaaaugucc | 180 |
| guucgguugg | cagaagcuau | gaaacgauau | gggcugaaua | caaaucacag | aaucgucgua | 240 |
| ugcagugaaa | acucucuuca | auucuuuaug | ccggucuugg | gcgcguuauu | uaucggaguu | 300 |
| gcaguugcgc | ccgcgaacga | cauuuauaau | gaacgugaau | ugcucaacag | uaugggcauu | 360 |
| ucgcagccua | ccgugugguu | cguuccaaa | aaggggguugc | aaaaaauuuu | gaacgugcaa | 420 |
| aaaaagcucc | caaucaucca | aaaaauuauu | aucauggauu | cuaaaacgga | uuaccaggga | 480 |
| uuucagucga | uguacacguu | cgucacaucu | caucuaccuc | ccgguuuuaa | ugaauacgau | 540 |
| uuugugccag | aguccuucga | uagggacaag | acaauugcac | ugaucaugaa | cuccucugga | 600 |
| ucuacugguc | ugccuaaagg | ugucgcucug | ccucauagaa | cugccugcgu | gagauucucg | 660 |
| caugccagag | auccuauuuu | uggcaaucaa | aucauuccgg | auacugcgau | uuaagugguu | 720 |
| guuccauucc | aucacgguuu | ggaauguuu | acuacacucg | gauauuugau | auguggauuu | 780 |
| cgagucgucu | uaauguauag | auuugaagaa | gagcuguuuc | ugaggagccu | ucaggauuac | 840 |
| aagauucaaa | gugcgcugcu | ggugccaacc | cuauucuccu | ucuuccgccaa | aagcacucug | 900 |
| auugacaaau | acgauuuauc | uaauuuacac | gaaauugcuu | cuggugggcgc | uccccucucu | 960 |
| aaggaagucg | gggaagcggu | ugccaagagg | uuccaucugc | cagguaucag | gcaaggauau | 1020 |
| gggcucacug | agacuacauc | agcuauucug | auuacacccg | aggggggauga | uaaaccgggc | 1080 |
| gcggucggua | aaguuguucc | auuuuugaa | gcgaagguug | uggaucugga | uaccggggaaa | 1140 |
| acgcugggcg | uuaaucaaag | aggcgaacug | ugugugagag | guccuaugau | uaugucccggu | 1200 |
| uauguaaaca | auccggaagc | gaccaacgcc | uugauugaca | aggauggaug | gcuacauucu | 1260 |
| ggagacauag | cuuacuggga | cgaagacgaa | cacuucuuca | ucguugaccg | ccugaagucu | 1320 |
| cugauuaagu | acaaaggcua | ucagguggcu | cccgcugaau | uggaauccau | cuugcuccaa | 1380 |
| caccccaaca | ucuucgacgc | aggugucgca | ggucuucccg | acgaugacgc | cggugaacuu | 1440 |
| cccgccgccg | uuguuguuuu | ggagcacgga | aagacgauga | cggaaaaaga | gaucguggau | 1500 |
| uacgucgcca | gucaaguaac | aaccgcgaaa | aaguugcgcg | gaggaguugu | guuuguggac | 1560 |
| gaaguaccga | aaggucuuac | cggaaaacuc | gacgcaagaa | aaaucagaga | gauccucaua | 1620 |
| aaggccaaga | agggcggaaa | gaucgccgug | uaa | | | 1653 |

<210> SEQ ID NO 34
<211> LENGTH: 17
<212> TYPE: RNA
<213> ORGANISM: Artificial sequence
<220> FEATURE:
<223> OTHER INFORMATION: synthetic RNA

<400> SEQUENCE: 34
acucuuuguc gccuucg                                                17

<210> SEQ ID NO 35
<211> LENGTH: 17
<212> TYPE: RNA
<213> ORGANISM: Artificial sequence
<220> FEATURE:
<223> OTHER INFORMATION: synthetic RNA

<400> SEQUENCE: 35
cucggccaca gcgaugc                                                    17

<210> SEQ ID NO 36
<211> LENGTH: 17
<212> TYPE: RNA
<213> ORGANISM: Artificial sequence
<220> FEATURE:
<223> OTHER INFORMATION: synthetic RNA

<400> SEQUENCE: 36
ucuuugagca ccuccag                                                    17

<210> SEQ ID NO 37
<211> LENGTH: 17
<212> TYPE: RNA
<213> ORGANISM: Artificial sequence
<220> FEATURE:
<223> OTHER INFORMATION: synthetic RNA

<400> SEQUENCE: 37
cucuagaugc augcucg                                                    17

<210> SEQ ID NO 38
<211> LENGTH: 17
<212> TYPE: RNA
<213> ORGANISM: Artificial sequence
<220> FEATURE:
<223> OTHER INFORMATION: synthetic RNA

<400> SEQUENCE: 38
gcggcagcca cuucuug                                                    17

<210> SEQ ID NO 39
<211> LENGTH: 17
<212> TYPE: RNA
<213> ORGANISM: Artificial sequence
<220> FEATURE:
<223> OTHER INFORMATION: synthetic RNA

<400> SEQUENCE: 39
aucucaggaa ugucgac                                                    17

<210> SEQ ID NO 40
<211> LENGTH: 17
<212> TYPE: RNA
<213> ORGANISM: Artificial sequence
<220> FEATURE:
<223> OTHER INFORMATION: synthetic RNA

<400> SEQUENCE: 40
gcagccagcu uuccggg                                                    17

<210> SEQ ID NO 41
<211> LENGTH: 17
<212> TYPE: RNA
<213> ORGANISM: Artificial sequence
<220> FEATURE:
<223> OTHER INFORMATION: synthetic RNA

```
<400> SEQUENCE: 41
uugaggcagc caguugu                                                    17

<210> SEQ ID NO 42
<211> LENGTH: 17
<212> TYPE: RNA
<213> ORGANISM: Artificial sequence
<220> FEATURE:
<223> OTHER INFORMATION: synthetic RNA

<400> SEQUENCE: 42
ugaucuuguc caccugg                                                    17

<210> SEQ ID NO 43
<211> LENGTH: 17
<212> TYPE: RNA
<213> ORGANISM: Artificial sequence
<220> FEATURE:
<223> OTHER INFORMATION: synthetic RNA

<400> SEQUENCE: 43
gaugaacuuc uucaucu                                                    17

<210> SEQ ID NO 44
<211> LENGTH: 17
<212> TYPE: RNA
<213> ORGANISM: Artificial sequence
<220> FEATURE:
<223> OTHER INFORMATION: synthetic RNA

<400> SEQUENCE: 44
gugggacagg cagauca                                                    17

<210> SEQ ID NO 45
<211> LENGTH: 17
<212> TYPE: RNA
<213> ORGANISM: Artificial sequence
<220> FEATURE:
<223> OTHER INFORMATION: synthetic RNA

<400> SEQUENCE: 45
uugaagucuu cguuguu                                                    17

<210> SEQ ID NO 46
<211> LENGTH: 17
<212> TYPE: RNA
<213> ORGANISM: Artificial sequence
<220> FEATURE:
<223> OTHER INFORMATION: synthetic RNA

<400> SEQUENCE: 46
gggcaacuuc ccgcggu                                                    17

<210> SEQ ID NO 47
<211> LENGTH: 17
<212> TYPE: RNA
<213> ORGANISM: Artificial sequence
<220> FEATURE:
<223> OTHER INFORMATION: synthetic RNA

<400> SEQUENCE: 47
cugcuccaug ggcucca                                                    17
```

```
<210> SEQ ID NO 48
<211> LENGTH: 17
<212> TYPE: RNA
<213> ORGANISM: Artificial sequence
<220> FEATURE:
<223> OTHER INFORMATION: synthetic RNA

<400> SEQUENCE: 48
cuugcuggca aaggucg                                                  17

<210> SEQ ID NO 49
<211> LENGTH: 20
<212> TYPE: DNA
<213> ORGANISM: Artificial sequence
<220> FEATURE:
<223> OTHER INFORMATION: synthetic DNA

<400> SEQUENCE: 49
tgagattcct gggttcaagg                                               20

<210> SEQ ID NO 50
<211> LENGTH: 20
<212> TYPE: DNA
<213> ORGANISM: Artificial sequence
<220> FEATURE:
<223> OTHER INFORMATION: synthetic DNA

<400> SEQUENCE: 50
gtcagaacac tgcacgttgg                                               20

<210> SEQ ID NO 51
<211> LENGTH: 783
<212> TYPE: RNA
<213> ORGANISM: Artificial sequence
<220> FEATURE:
<223> OTHER INFORMATION: synthetic RNA

<400> SEQUENCE: 51
gggagaccgg ccucgagcag cugaagcuug guaccgagcu cggauccagc caccauggga   60
gucaaaguuc uguuugcccu gaucugcauc gcuguggccg aggccaagcc caccgagaac  120
aacgaagacu ucaacaucgu ggccguggcc agcaacuucg cgaccacgga ucucgaugcu  180
gaccgcggga aguugcccgg caagaagcug ccgcuggagg ugcucaaaga gauggaagcc  240
aaugcccgga agcugguucaa ccaggggc ugucugaucu gccugcccca caucaagugc  300
acgcccaaga ugaagaaguu caucccagga cgcugccaca ccuacgaagg cgacaaagag  360
uccgcacagg gcggcauagg cgaggcgauc gucgacauuc cugagauucc ugggguucaag  420 gacuuggagc ccauggagca guucaucgca caggucgauc ugugugugga cugcacaacu  480
ggcugccuca aagggcuugc caacgugcag uguucugacc ugcucaagaa guggcugccg  540
caacgcugug cgaccuuugc cagcaagauc cagggccagg uggacaagau caagggggcc  600 ggugguigacu aagcggccgc ucgagcaugc aucuagagga uccccgggua ccgagcucga  660
auucaaaaaa aaaaaaaaaa aaaaaaaaaa aaaaaaaaaa aaaaaaaaaa aaaaaaaaaa  720
aaaaaaaaaa aaaaaaaaaa aaaaaaaaaa aaaaaaaaaa aaaaaaaaaa aaaaaaaaaa  780
aaa                                                                783

<210> SEQ ID NO 52
<211> LENGTH: 777
<212> TYPE: RNA
<213> ORGANISM: Artificial sequence
```

<220> FEATURE:
<223> OTHER INFORMATION: synthetic RNA

<400> SEQUENCE: 52

```
gaaccagauc ucgucucuuu uuuuuuuuuu uuuuuuuuuu uuuuuuuuuu uuuuuuuuuu        60
uuuuuuuuuu uuuuuuuuuu uuuuuuuuuu uuuuuuuuuu uuuuuuuuuu uuuuuuuuuu       120
uuuuuuuuuu uuuuuuugaa uucgagcucg guacccgggg auccucuaga ugcaugcucg       180
agcggccgcu uagucaccac cggccccuu gaucuuguc accuggccu ggaucuugcu          240
ggcaaagguc gcacagcguu gcggcagcca cuucuugagc aggucagaac acugcacguu       300
ggcaagcccu uugaggcagc caguugugca guccacacac agaucgaccu gugcgaugaa       360
cugcuccaug ggcuccaagu ccuugaaccc aggaaucuca ggaaugucga cgaucgccuc       420
gccuaugccg cccugugcgg acucuuuguc gccuucguag guguggcagc guccugggau       480
gaacuucuuc aucuugggcg ugcacuugau ugggacagg cagaucagac agccccuggu       540
gcagccagcu uuccgggcau uggcuuccau cucuuugagc accuccagcg gcagcuucuu       600
gccgggcaac uucccgcggu cagcaucgag auccggguc gcgaaguugc uggcacggc        660
cacgauguug aagucuucgu uguucucggu gggcuuggcc ucggcacag cgaugcagau       720
cagggcaaac agaacuuuga cucccauggu ggcuggaucc gagcucggua ccaagcu         777
```

<210> SEQ ID NO 53
<211> LENGTH: 663
<212> TYPE: RNA
<213> ORGANISM: Artificial sequence
<220> FEATURE:
<223> OTHER INFORMATION: synthetic RNA

<400> SEQUENCE: 53

```
gaaccagauc ugauaucauc gaugaauucg agcucgguac ccggggaucc ucuagaugca        60
ugcucgagcg gccgcuuagu caccaccggc ccccuugauc uuguccaccu ggcccuggau       120
cuugcuggca aaggucgcac agcguugcgg cagccacuuc uugagcaggu cagaacacug       180
cacguuggca agcccuuuga ggcagccagu ugugcagucc acacagau cgaccugugc         240
gaugaacugc uccaugggcu ccaagucuu gaacccagga aucuaggaa ugucgacgau         300
cgccucgccu augccgcccu gugcggacuc uuugucgccu ucguaggugu ggcagcguc        360
ugggaugaac uucuucaucu ugggcgugca cuugaugugg acaggcaga ucagacagcc       420
ccugguqcag ccagcuuucc gggcauuggc uuccaucucu uugagcaccu ccagcggcag       480
cuucuugccg ggcaacuucc cgcggucagc aucgagaucc guggucgcga aguugcuggc       540
cacggccacg auguugaagu cuucguuguu cucggugggc uuggcucgg ccacagcgau        600
gcagaucagg gcaaacagaa cuuugacucc cauggugcu ggauccgagc ucgguaccaa        660
gcu                                                                    663
```

<210> SEQ ID NO 54
<211> LENGTH: 156
<212> TYPE: RNA
<213> ORGANISM: Artificial sequence
<220> FEATURE:
<223> OTHER INFORMATION: synthetic RNA

<400> SEQUENCE: 54

```
gaaccagauc ucgucucuuu uuuuuuuuuu uuuuuuuuuu uuuuuuuuuu uuuuuuuuuu      60
uuuuuuuuuu uuuuuuuuuu uuuuuuuuuu uuuuuuuuuu uuuuuuuuuu uuuuuuuuuu     120
uuuuuuuuuu uuuuuugaa uucgagcucg guaccc                                156
```

<210> SEQ ID NO 55
<211> LENGTH: 1303
<212> TYPE: RNA
<213> ORGANISM: Artificial sequence
<220> FEATURE:
<223> OTHER INFORMATION: synthetic RNA

<400> SEQUENCE: 55

```
gggagaccgg ccucgagaug ggcagcaucg gggcagcaag cauggaguuu uguuuugacg      60
uguuuaagga acugaaagug caucacgcua augagaauau cuucuacugc cccaucgcca     120
uuaugucugc ccuggcuaug uguuaucugg gagcuaagga caguaccaga acacagauca     180
acaagguggu ccgcuucgac aaacugcccg gguuggcga cagcauugag gcucagugug     240
gcacuuccgu gaauguccac agcucccuga gggacauccu gaaccagauu accaagccua     300
augacgugua ucccuucucu cuggccuccc ggcugacgc ugaggaaagg uaucccaucc     360
ugccugagua ccugcagugc gugaaagaac uguauagggg cggacuggag ccaaucaacu     420
uucagacagc cgcugaccag gccagagaac ugauuaauuc ugggguggag agucagacua     480
acgguaucau ucgcaaugug cugcagcccu cuagugucga uagccagacc gcuauggugc     540
uggucaacgc aaucuguuuc aagggccugu gggagaagac cuucaaggac gaagauacuc     600
aggcaaugcc auuccgagug acagagcagg aaagcaaacc cguccagaug auguaucaga     660
ucggccuguu cagaguggcu agcauggcau ccgagaagau gaaaauucug gaacugccuu     720
uugccucagg aaccaugagc augcgggugc ugcugccaga cgaggucagu gggcuggagc     780
agcuggaauc aaucauuaac uucgagaagc ugacugaaug gaccucaagc aaugugaugg     840
aggaacgaaa gaucaaaguc uaccugccuc ggaugaagau ggaggaaaaa uauaaccuga     900
ccuccgugcu gauggcuaug gguauuacag augucuuuc cucuagugcc aaucugucug     960
gcaucucaag cgccgagucc cugaagauuu ucaggcagu gcacgcagcc caugcagaga    1020
ucaaugaagc cggccgcgag guggucggau cugcagaagc cggggugac gcugcaagug    1080
ucucagagga guuccgggcc gaucauccau ucuguucug uaucaaacau auugccacaa    1140
augccgugcu guucuucggu agaugcgugu caccaugaga auucaaaaaa aaaaaaaaaa    1200
aaaaaaaaaa aaaaaaaaaa aaaaaaaaaa aaaaaaaaaa aaaaaaaaaa aaaaaaaaaa    1260
aaaaaaaaaa aaaaaaaaaa aaaaaaaaaa aaaaaaaaaa aaa                      1303
```

<210> SEQ ID NO 56
<211> LENGTH: 142
<212> TYPE: RNA
<213> ORGANISM: Artificial sequence
<220> FEATURE:
<223> OTHER INFORMATION: synthetic RNA

<400> SEQUENCE: 56

```
gaaccagauc ucgucucuuu uuuuuuuuuu uuuuuuuuuu uuuuuuuuuu uuuuuuuuuu      60
uuuuuuuuuu uuuuuuuuuu uuuuuuuuuu uuuuuuuuuu uuuuuuuuuu uuuuuuuuuu     120
uuuuuuuuuu uuuuuugaa uu                                               142
```

<210> SEQ ID NO 57
<211> LENGTH: 558
<212> TYPE: DNA
<213> ORGANISM: Artificial sequence
<220> FEATURE:
<223> OTHER INFORMATION: synthetic DNA

<400> SEQUENCE: 57

```
atgggagtca aagttctgtt tgccctgatc tgcatcgctg tggccgaggc caagcccacc        60
gagaacaacg aagacttcaa catcgtggcc gtggccagca acttcgcgac cacggatctc       120
gatgctgacc gcgggaagtt gcccggcaag aagctgccgc tggaggtgct caaagagatg       180
gaagccaatg cccggaaagc tggctgcacc aggggctgtc tgatctgcct gtcccacatc       240
aagtgcacgc ccaagatgaa gaagttcatc ccaggacgct gccacaccta cgaaggcgac       300
aaagagtccg cacagggcgg cataggcgag gcgatcgtcg acattcctga gattcctggg       360
ttcaaggact ggagcccat ggagcagttc atcgcacagg tcgatctgtg tgtggactgc        420
acaactggct gcctcaaagg gcttgccaac gtgcagtgtt ctgacctgct caagaagtgg       480
ctgccgcaac gctgtgcgac cttttgccagc aagatccagg ccaggtgga caagatcaag       540 ggggccggtg gtgactaa                                                    558
```

<210> SEQ ID NO 58
<211> LENGTH: 1161
<212> TYPE: DNA
<213> ORGANISM: Artificial sequence
<220> FEATURE:
<223> OTHER INFORMATION: synthetic DNA

<400> SEQUENCE: 58

```
atgggcagca tcggggcagc aagcatggag ttttgttttg acgtgtttaa ggaactgaaa        60
gtgcatcacg ctaatgagaa tatcttctac tgccccatcg ccattatgtc tgccctggct       120
atggtgtatc tgggagctaa ggacagtacc agaacacaga tcaacaaggt ggtccgcttc       180
gacaaactgc ccgggtttgg cgacagcatt gaggctcagt gtggcacttc cgtgaatgtc       240
cacagctccc tgagggacat cctgaaccag attaccaagc ctaatgacgt gtactccttc       300
tctctggcct cccggctgta cgctgaggaa aggtatccca tcctgcctga gtacctgcag       360
tgcgtgaaag aactgtatag gggcggactg gagccaatca actttcagac agccgctgac       420
caggccagag aactgattaa ttcttgggtg gagagtcaga ctaacggtat cattcgcaat       480
gtgctgcagc cctctagtgt cgatagccag accgctatgg tgctggtcaa cgcaatcgtg       540
ttcaagggcc tgtgggagaa gaccttcaag gacgaagata tcaggcaat gccattccga       600 gtgacagagc aggaaagcaa acccgtccag atgatgtatc agatcggcct gttcagagtg       660
gctagcatgg catccgagaa gatgaaaatt ctggaactgc cttttgcctc aggaaccatg       720
agcatgctgg tgctgctgcc agacgaggtc agtgggctgg agcagctgga atcaatcatt       780
aacttcgaga agctgactga atggaccctca agcaatgtga tggaggaacg aaagatcaaa       840
gtctacctgc ctcggatgaa gatggaggaa aaatataacc tgacctccgt gctgatggct       900
atgggtatta cagatgtctt ttcctctagt gccaatctgt ctggcatctc aagcgccgag       960
tccctgaaga tttctcaggc agtgcacgca gcccatgcag agatcaatga agccggccgc      1020
gaggtggtcg gatctgcaga agccggggtg gacgctgcaa gtgtctcaga ggagttccgg      1080
gccgatcatc catttctgtt ctgtatcaaa catattgcca caaatgccgt gctgttcttc      1140
ggtagatgcg tgtcaccatg a                                               1161
```

```
<210> SEQ ID NO 59
<211> LENGTH: 187
<212> TYPE: RNA
<213> ORGANISM: Artificial sequence
<220> FEATURE:
<223> OTHER INFORMATION: synthetic RNA

<400> SEQUENCE: 59
gaaccagauc ucgucucuuu uuuuuuuuuu uuuuuuuuuu uuuuuuuuuu uuuuuuuuuu      60
uuuuuuuuuu uuuuuuuuuu uuuuuuuuuu uuuuuuuuuu uuuuuuuuuu uuuuuuuuuu     120
uuuuuuuuuu uuuuuuugaa uucgagcucg guacccgggg auccucuaga ugcaugcucg     180
agcggcc                                                               187

<210> SEQ ID NO 60
<211> LENGTH: 43
<212> TYPE: RNA
<213> ORGANISM: Artificial sequence
<220> FEATURE:
<223> OTHER INFORMATION: synthetic RNA

<400> SEQUENCE: 60
cagccagcuu uccgggcuac acacacacac acacacacac acc                        43

<210> SEQ ID NO 61
<211> LENGTH: 43
<212> TYPE: RNA
<213> ORGANISM: Artificial sequence
<220> FEATURE:
<223> OTHER INFORMATION: synthetic RNA

<400> SEQUENCE: 61
acucuuuguc gccuucgauc acacacacac acacacacac acc                        43

<210> SEQ ID NO 62
<211> LENGTH: 43
<212> TYPE: RNA
<213> ORGANISM: Artificial sequence
<220> FEATURE:
<223> OTHER INFORMATION: synthetic RNA

<400> SEQUENCE: 62
gcggcagcca cuucuuguac acacacacac acacacacac acc                        43

<210> SEQ ID NO 63
<211> LENGTH: 31
<212> TYPE: DNA
<213> ORGANISM: Artificial sequence
<220> FEATURE:
<223> OTHER INFORMATION: synthetic DNA

<400> SEQUENCE: 63
taggtgtgtg tgtgtgtgtg tgtgtgggcc c                                     31

<210> SEQ ID NO 64
<211> LENGTH: 31
<212> TYPE: DNA
<213> ORGANISM: Artificial sequence
<220> FEATURE:
<223> OTHER INFORMATION: synthetic DNA

<400> SEQUENCE: 64
aaacgggccc acacacacac acacacacac a                                     31
```

<210> SEQ ID NO 65
<211> LENGTH: 2153
<212> TYPE: DNA
<213> ORGANISM: Artificial sequence
<220> FEATURE:
<223> OTHER INFORMATION: synthetic DNA

<400> SEQUENCE: 65

```
tgggcctttc ttcggtagaa aatcaaagga tcttcttgag atccttttt  tctgcgcgta    60
atctgctgct tgcaaacaaa aaaaccaccg ctaccagcgg tggtttgttt gccggatcaa   120
gagctaccaa ctcttttcc gaggtaactg gcttcagcag agcgcagata ccaaatactg   180
ttcttctagt gtagccgtag ttaggccacc acttcaagaa ctctgtagca ccgcctacat   240
acctcgctct gctaatcctg ttaccagtgg ctgctgccag tggcgataag tcgtgtctta   300
ccgggttgga ctcaagacga tagttaccgg ataaggcgca gcggtcgggc tgaacggggg   360
gttcgtgcac acagcccagc ttggagcgaa cgacctacac cgaactgaga tacctacagc   420
gtgagctatg agaaagcgcc acgcttcccg aagggagaaa ggcggacagg tatccggtaa   480
gcggcagggt cggaacagga gagcgcacga gggagcttcc agggggaaac gcctggtatc   540
tttatagtcc tgtcgggttt cgccacctct gacttgagca tcgattttg  tgatgctcgt   600
caggggggcg gagcctatgg aaaaacgcca gcaacgcaga aaggcccacc cgaaggtgag   660
ccaggtgatt acatttaggt cctcattaga aaaactcatc gagcatcaag tgaaactgca   720
atttattcat atcaggatta tcaataccat attttgaaa  aagccgtttc tgtaatgaag   780
gagaaaactc accgaggcag ttccatagga tggcaagatc ctggtatcgg tctgcgattc   840
cgactcgtcc aacatcaata caacctatta atttcccctc gtcaaaaata aggttatcaa   900
gtgagaaatc accatgagtg acgactgaat ccggtgagaa tggcaagagt ttatgcattt   960
ctttccagac ttgttcaaca ggccagccat tacgctcgtc atcaaaatca ctcgcaccaa  1020
ccaaaccgtt attcattcgt gattgcgcct gagcgagacg aaatacgcga tcgccgttaa  1080
aaggacaatt acaaacagga atcgaatgca accggcgcag gaacactgcc agcgcatcaa  1140
caatattttc acctgaatca ggatattctt ctaatacctg gaatgctgtt ttccctggga  1200
tcgcagtggt gagtaaccat gcatcatcag gagtacggat aaaatgcttg atggtcggaa  1260
gaggcataaa ttccgtcagc cagtttagcc tgaccatctc atctgtaaca tcattggcaa  1320
cgctaccttt gccatgtttc agaaacaact ctggcgcatc gggcttccca tacaatcgat  1380
agattgtcgc acctgattgc ccgacattat cgcgagccca tttataccca tataaatcag  1440
catccatgtt ggaatttaat cgcggcttca agcaagacgt ttcccgttga atatggctca  1500
ttttagcttc cttagctcct gaaaatctcg ataactcaaa aaatacgccc ggtagtgatc  1560
ttatttcatt atggtgaaag ttggaacctc ttacgtgccg atcaagtcaa aagcctccgg  1620
tcggaggctt ttgactttct gctatggagg tcaggtatga tttaaatggt cagtattgag  1680
cctcaggaaa cagctatgac atcaagctga ctagataatc tagctgatcg tggaccgatc  1740
atacgtataa tgccgtaaga tcacgggtcg cagcacagct cgcggtccag tagtgatcga  1800
cactgctcga tccgctcgca ccgctagcta atacgactca ctataggtgt gtgtgtgtgt  1860
gtgtgtgtgg gcccgtttta gagctagaaa tagcaagtta aaataaggct agtccgttat  1920
caacttgaaa aagtggcacc gagtcggtgc ttttaaaaag cttggatcga cgagagcagc  1980
gcgactggat ctgtcgcccg tctcaaacgc aaccctccgg cggtcgcata tcattcagga  2040
```

```
cgagcctcag actccagcgt aactggactg caatcaactc actggctcac cttccggtcc    2100
acgatcagct agaatcaagc tgactagata aactggccgt cgttttacac ggg           2153

<210> SEQ ID NO 66
<211> LENGTH: 24
<212> TYPE: RNA
<213> ORGANISM: Artificial sequence
<220> FEATURE:
<223> OTHER INFORMATION: synthetic RNA

<400> SEQUENCE: 66
ggugugugug ugugugugug ugug                                             24

<210> SEQ ID NO 67
<211> LENGTH: 10
<212> TYPE: RNA
<213> ORGANISM: Artificial sequence
<220> FEATURE:
<223> OTHER INFORMATION: synthetic RNA

<400> SEQUENCE: 67
gugugugugu                                                             10

<210> SEQ ID NO 68
<211> LENGTH: 10
<212> TYPE: RNA
<213> ORGANISM: Artificial sequence
<220> FEATURE:
<223> OTHER INFORMATION: synthetic RNA

<400> SEQUENCE: 68
acacacacac                                                             10
```

MRNA FUNCTIONALIZATION METHOD

TECHNICAL FIELD

The present invention relates to a method for functionalizing mRNA. More specifically, the present invention relates to a method for stabilizing an mRNA carrier, an mRNA vaccine, and the like.

BACKGROUND ART mRNA delivery has attracted attention as a method of supplying a therapeutic protein into a body safely and continuously. On the other hand, such mRNA delivery is greatly problematic in that enzymatic degradation of mRNA promptly occurs in a living body. To solve this issue, a method of protecting mRNA from degradation by using an mRNA carrier and a method of improving an mRNA molecule itself have been studied. However, since the action of RNA-degrading enzyme is extremely strong in a living body, further technical innovation has been desired.

Regarding the method of improving an mRNA molecule itself, a method of replacing some mRNA nucleotides with chemically modified nucleotides has been studied (for example, Non Patent Literature 1). To date, various chemically modified nucleotides have been comprehensively studied. However, chemically modified nucleotides capable of significantly improving the enzyme resistance of mRNA have not yet been reported. Moreover, since the efficiency of translating a protein from mRNA is often largely decreased by performing modification on the nucleotides, it has been difficult to perform chemical modification, as desired.

Patent Literature 1 discloses a polyion complex consisting of a polycationic polymer and an mRNA, and the use of the polyion complex in mRNA delivery. In addition, Non Patent Literature 2 discloses the stability of a polymeric micelle-type mRNA carrier, evaluation of enzymatic degradation, and the effect of performing cholesterol modification on the polymer. However, these publications do not disclose a method for stabilizing an mRNA carrier, by which the enzyme resistance of an mRNA can be improved in a living body, without largely decreasing the efficiency of translating a protein from the mRNA.

The conventional live vaccine, in which the pathogenicity of a pathogen has been attenuated, is likely to cause side effects as a result of the reactivation of the pathogenicity. The conventional inactivated vaccine, in which the pathogenicity of a pathogen has been lost, is problematic in that cellular immunity is hardly induced because infected cells do not appear.

In the case of a nucleic acid vaccine such as a DNA vaccine or an mRNA vaccine, a nucleic acid is used to present an antigenic protein. That is to say, in the case of such a nucleic acid vaccine, the administered nucleic acid is transferred into the nucleus or cytoplasm of an antigen-presenting cell and an antigenic protein is then allowed to express and to be present therein, so as to activate immunity. Since the nucleic acid vaccine does not have a problem regarding the reactivation of the pathogenicity, the nucleic acid vaccine is considered to have higher safety, in comparison to the live vaccine. Moreover, since the antigen-presenting cell presents an antigenic protein in the nucleic acid vaccine, it is possible to induce cellular immunity. Thus, the nucleic acid vaccine can be applied to cancer or chronic infection. Furthermore, in the case of the nucleic acid vaccine, it is possible to relatively freely design a nucleic acid only by changing the sequence, and thus, the nucleic acid vaccine is advantageous in that it can be used in the personalized treatment of cancer, and in that it can quickly respond to virus mutation, so that it can quickly cope with pandemic, and the like.

Among these vaccines, the DNA vaccine is considered to have the risk of causing mutagenesis due to random insertion into the host genome. In contrast, the mRNA vaccine, which uses an mRNA for antigenic protein presentation, is considered not to have the risk of causing mutagenesis to the host genome, and thus, the mRNA vaccine has attracted attention in recent years.

In order to obtain immune induction effects by using an mRNA vaccine, it is necessary to allow an antigenic protein to express, and at the same time, to provoke an inflammatory response. However, since the mRNA itself has low immunogenicity, it hardly provokes the inflammatory response. Hence, it has conventionally been necessary to simultaneously administer an adjuvant for provoking the inflammatory response, as well as the mRNA (for example, Patent Literature 2).

Such a conventional mRNA vaccine has the following three problems. The first problem is that when a foreign matter is used as an adjuvant, considerable attention should be paid to the safety of the foreign matter. The second problem is that if the administered mRNA is different from the adjuvant in terms of histological distribution, it is likely that a sufficient inflammatory response is not provoked in a cell that expresses an antigenic protein. The third problem is that upon administration of the mRNA into a living body, a carrier is often necessary to protect the mRNA from enzymatic degradation, but the adjuvant is likely to affect the function of the carrier.

Non Patent Literature 3 discloses, as an mRNA vaccine, an mRNA that is integrated with protamine as an adjuvant component.

CITATION LIST

Patent Literature

Patent Literature 1: WO 2015/121924 A
Patent Literature 2: JP-2012-502074-A

Non Patent Literature

Non Patent Literature 1: Meis, J. E. and Chen, F. (2002) EPICENTRE Forum 9(1), 10
Non Patent Literature 2: Uchida, S., et al., *Biomaterials* (2016) 82, pp. 221-228.
Non Patent Literature 3: Karl-Josef Kallen et al., Human Vaccines & Immunotherapeutics (2013) 9: 10, pp. 2263-2276

SUMMARY OF INVENTION

Technical Problem

Under such circumstances, it has been desired to develop a functionalized mRNA.

In a first aspect, it is an object of the present invention to provide a novel method for stabilizing an mRNA carrier.

In second and third aspects, it is an object of the present invention to provide a novel mRNA vaccine enabling efficient protein expression and immune induction.

Solution to Problem

As a result of intensive studies, the present inventors have found that an mRNA can be functionalized by allowing an RNA oligomer having a sequence complementary to an mRNA to hybridize with the mRNA, thereby completing the present invention.

In addition, the present inventors have found that an mRNA can be chemically modified by chemically modifying an RNA oligomer having a sequence complementary to the mRNA, and then allowing the RNA oligomer to hybridize with the mRNA, so that the mRNA can be stabilized, or the mRNA is incorporated into a carrier, so that the carrier can be stabilized, thereby completing a first aspect of the present invention.

Moreover, the present inventors have found that both efficient protein expression from mRNA and immune induction can be achieved by allowing an RNA oligomer having a sequence complementary to the poly A sequence of an mRNA encoding an antigen to hybridize with the mRNA, thereby completing a second aspect of the present invention.

Furthermore, the present inventors have found that both efficient protein expression from mRNA and immune induction can be achieved by allowing a first RNA oligomer having a sequence complementary to the sequence of an mRNA encoding an antigen to hybridize with the mRNA, and also by allowing a second RNA oligomer having a sequence complementary to the first RNA oligomer to hybridize with the first RNA oligomer, thereby completing a third aspect of the present invention.

The present invention is as follows.

A functionalized mRNA, which comprises a double-stranded RNA comprising an mRNA and at least one modified RNA oligomer hybridizing with the mRNA.

The first aspect of the present invention is as follows.

[1-1] An mRNA carrier, which loads therein an mRNA encoding a target gene and at least one RNA oligomer hybridizing with the mRNA, wherein
the RNA oligomer comprises:
(a) an RNA sequence consisting of a sequence of 12 to 40 nucleotides complementary to the sequence of the mRNA, or
(b) an RNA sequence having an identity of 90% or more to a sequence of 12 to 40 nucleotides complementary to the sequence of the mRNA, and hybridizing with the mRNA, and the RNA oligomer is chemically modified.

[1-1A] An mRNA carrier, which loads therein an mRNA encoding a target gene and at least one RNA oligomer hybridizing with the mRNA, wherein
the RNA oligomer comprises:
(a) an RNA sequence consisting of a sequence of 12 to 40 nucleotides complementary to the sequence of the mRNA, or
(b) an RNA sequence having an identity of 90% or more to a sequence of 12 to 40 nucleotides complementary to the sequence of the mRNA, and hybridizing with the mRNA, and the RNA oligomer is chemically unmodified or is chemically modified.

[1-2] The carrier according to the above [1-1] or [1-1A], wherein the RNA sequence consists of a sequence of 15 to 23 nucleotides.

[1-3] The carrier according to the above [1-2], wherein the RNA sequence consists of a sequence of 17 nucleotides.

[1-4] The carrier according to any one of the above [1-1] to [1-3], wherein the chemical modification is performed on the 5'-terminus or 3'-terminus of the sequence of the RNA oligomer via an overhang sequence consisting of 1 to 5 nucleotides.

[1-5] The carrier according to the above [1-4], wherein the overhang sequence is a sequence consisting of 2 nucleotides.

[1-6] The carrier according to any one of the above [1-1] to [1-5], wherein the chemical modification is modification with a hydrophobic group.

[1-7] The carrier according to the above [1-6], wherein the modification with a hydrophobic group is cholesterol modification.

[1-8] The carrier according to any one of the above [1-1] to [1-5], wherein the chemical modification is polyethylene glycol modification.

[1-9] The carrier according to any one of the above [1-1] to [1-8], wherein the carrier is a polymeric micelle or a lipidic mRNA carrier.

[1-10] A pharmaceutical composition comprising the carrier according to any one of the above [1-1] to [1-9].

[1-11] A method for stabilizing a carrier, which comprises techniques allowing a carrier to load therein an mRNA encoding a target gene and at least one RNA oligomer hybridizing with the mRNA, wherein
the RNA oligomer comprises:
(a) an RNA sequence consisting of a sequence of 12 to 40 nucleotides complementary to the sequence of the mRNA, or
(b) an RNA sequence having an identity of 90% or more to a sequence of 12 to 40 nucleotides complementary to the sequence of the mRNA, and hybridizing with the mRNA, and the RNA oligomer is chemically modified.

[1-11A] A method for stabilizing a carrier, which comprises techniques allowing a carrier to load therein an mRNA encoding a target gene and at least one RNA oligomer hybridizing with the mRNA, wherein
the RNA oligomer comprises:
(a) an RNA sequence consisting of a sequence of 12 to 40 nucleotides complementary to the sequence of the mRNA, or
(b) an RNA sequence having an identity of 90% or more to a sequence of 12 to 40 nucleotides complementary to the sequence of the mRNA, and hybridizing with the mRNA, and the RNA oligomer is chemically unmodified or is chemically modified.

[1-12] A double-stranded RNA comprising an mRNA encoding a target gene and at least one RNA oligomer hybridizing with the mRNA, wherein
the RNA oligomer comprises:
(a) an RNA sequence consisting of a sequence of 12 to 40 nucleotides complementary to the sequence of the mRNA, or
(b) an RNA sequence having an identity of 90% or more to a sequence of 12 to 40 nucleotides complementary to the sequence of the mRNA, and hybridizing with the mRNA, and the RNA oligomer is chemically unmodified or is chemically modified.

[1-13] The double-stranded RNA according to the above [1-12], wherein the RNA sequence consists of a sequence of 15 to 23 nucleotides.

[1-14] The double-stranded RNA according to the above [1-13], wherein the RNA sequence consists of a sequence of 17 nucleotides.

[1-15] The double-stranded RNA according to any one of the above [1-12] to [1-14], wherein the chemical modification is performed on the 5'-terminus or 3'-terminus of the sequence of the RNA oligomer via an overhang sequence consisting of 1 to 5 nucleotides.

[1-16] The double-stranded RNA according to the above [1-15], wherein the overhang sequence is a sequence consisting of 2 nucleotides.

[1-1.7] The double-stranded RNA according to any one of the above [1-12] to [1-16], wherein the chemical modification is modification with a hydrophobic group.

[1-18] The double-stranded RNA according to the above [1-17], wherein the modification with a hydrophobic group is cholesterol modification.

[1-19] The double-stranded RNA according to any one of the above [1-12] to [1-16], wherein the chemical modification is polyethylene glycol modification.

[1-20] An mRNA carrier loading therein the double-stranded RNA according to any one of the above [1-12] to [1-19].

[1-21] The carrier according to the above [1-20], which is a polymeric micelle or a lipidic mRNA carrier.

[1-22] A pharmaceutical composition comprising the carrier according to the above [1-20] or [1-21].

The second aspect of the present invention is as follows.

[2-1] An mRNA vaccine, which comprises a double-stranded RNA consisting of an mRNA encoding an antigen and at least one RNA oligomer hybridizing with at least the poly A sequence of the mRNA, wherein the at least one RNA oligomer is chemically unmodified.

[2-1A] An mRNA vaccine, which comprises a double-stranded RNA consisting of an mRNA encoding an antigen and at least one RNA oligomer hybridizing with at least the poly A sequence of the mRNA, wherein the at least one RNA oligomer is chemically unmodified or is chemically modified.

[2-2] The mRNA vaccine according to the above [2-1] or [2-1A], wherein the RNA oligomer consists of a nucleotide sequence of 10 to 500 nucleotides.

[2-3] The mRNA vaccine according to the above [2-1] or [2-2], wherein the RNA oligomer has a triphosphoric acid structure at the 5'-terminus thereof.

[2-4] The mRNA vaccine according to any one of the above [2-1] to [2-3], wherein the double-stranded RNA is formed by allowing one RNA oligomer to hybridize with at least the poly A sequence of the mRNA.

[2-5] The mRNA vaccine according to any one of the above [2-1] to [2-4], wherein the double-stranded RNA is in a naked form.

[2-6] The mRNA vaccine according to any one of the above [2-1] to [2-5], which is not used together with an adjuvant.

[2-7] The mRNA vaccine according to any one of the above [2-1] to [2-6], which is for use in the prevention or treatment of a disease in a subject in need thereof.

[2-8] A method for preventing or treating a disease, comprising administering the mRNA vaccine according to any one of the above [2-1] to [2-6] to a subject in need of the prevention or treatment of the disease.

The third aspect of the present invention is as follows.

[3-1] An mRNA vaccine, which comprises a double-stranded RNA consisting of an mRNA encoding an antigen, at least one first RNA oligomer hybridizing with the mRNA, and a second RNA oligomer hybridizing with the first RNA oligomer, wherein the first RNA oligomer comprises:

(a) an RNA sequence comprising a first RNA sequence consisting of a sequence of 12 to 40 nucleotides complementary to the sequence of the mRNA, and a second RNA sequence consisting of a sequence of 10 to 200 nucleotides complementary to the sequence of the second RNA oligomer, in this order from the 5'-terminus thereof, (b) an RNA sequence comprising a first RNA sequence having an identity of 90% or more to a sequence of 12 to 40 nucleotides complementary to the sequence of the mRNA and hybridizing with the mRNA, and a second RNA sequence having an identity of 90% or more to a sequence of 10 to 200 nucleotides complementary to the sequence of the second RNA oligomer and hybridizing with the second RNA oligomer, in this order from the 5'-terminus thereof, (c) an RNA sequence comprising a second RNA sequence consisting of a sequence of 10 to 200 nucleotides complementary to the second RNA oligomer, and a first RNA sequence consisting of a sequence of 12 to 40 nucleotides complementary to the sequence of the mRNA, in this order from the 5'-terminus thereof, or (d) an RNA sequence comprising a second RNA sequence having an identity of 90% or more to a sequence of 10 to 200 nucleotides complementary to the sequence of the second RNA oligomer and hybridizing with the second RNA oligomer, and a first RNA sequence having an identity of 90% or more to a sequence of 12 to 40 nucleotides complementary to the sequence of the mRNA and hybridizing with the mRNA, in this order from the 5'-terminus thereof.

[3-2] The mRNA vaccine according to the above [3-1], wherein the first RNA oligomer consists of a sequence of 22 to 240 nucleotides.

[3-3] The mRNA vaccine according to the above [3-1] or [3-2], wherein the number of the first RNA oligomers to be allowed to hybridize with one mRNA is 1 to 50.

[3-4] The mRNA vaccine according to any one of the above [3-1] to [3-3], wherein the first RNA oligomer comprises the RNA sequence (a) or the RNA sequence (b), and the second RNA oligomer has a triphosphoric acid structure at the 5'-terminus thereof.

[3-5] The mRNA vaccine according to any one of the above [3-1] to [3-3], wherein the first RNA oligomer comprises the RNA sequence (c) or the RNA sequence (d), and the first RNA oligomer has a triphosphoric acid structure at the 5'-terminus thereof.

[3-6] The mRNA vaccine according to any one of the above [3-1] to [3-5], wherein the terminus of the double-stranded RNA on the side at which the second RNA oligomer hybridizes with the first RNA oligomer is a blunt end.

[3-7] The mRNA vaccine according to any one of the above [3-1] to [3-6], wherein the second RNA oligomer comprises a sequence of 10 to 200 nucleotides.

[3-8] The mRNA vaccine according to any one of the above [3-1] to [3-7], wherein the double-stranded RNA is in a naked form.

[3-9] The mRNA vaccine according to any one of the above [3-1] to [3-8], which is not used together with an adjuvant.

[3-10] The mRNA vaccine according to any one of the above [3-1] to [3-9], which is for use in the prevention or treatment of a disease in a subject in need thereof.

Advantageous Effects of Invention

The present invention can provide a functionalized mRNA.

The first aspect of the present invention provides a novel method for stabilizing an mRNA or an mRNA carrier. Preferably, the first aspect of the present invention can realize relatively flexible mRNA modification, while maintaining the efficiency of translating a protein from the mRNA in a living body. More preferably, the first aspect of the present invention can suppress enzymatic degradation of the mRNA in a living body.

The second and third aspects of the present invention provide a novel mRNA vaccine capable of efficient protein expression and immune induction. Preferably, the mRNA vaccine according to the second and third aspects of the present invention enables antigen presentation and immune induction, without simultaneous administration of an adjuvant. More preferably, the mRNA vaccine according to the second and third aspects of the present invention can induce stronger cellular immunity. Further preferably, the mRNA vaccine according to the second and third aspects of the present invention can induce stronger humoral immunity than in the case of single administration of the mRNA.

BRIEF DESCRIPTION OF DRAWINGS

FIG. 4-1 is a view showing the influence of hybridization of a Chol modified RNA oligomer with an mRNA on stability. (A) PEG-PAsp(DET)-Chol; (B) PEG-PAsp(DET); (C) PEG-PAsp(DET)-Chol; (D) PEG-PAsp(DET); and (E) PEG-PAsp(DET)-Chol.

FIG. 4-2 is as described above.

FIG. 11 is a view showing hybridization of a Chol modified RNA oligomer with an mRNA on stability. (A) Gel electrophoresis (PEG-PLys+oligo(-)); (B) gel electrophoresis (PEG-PLys+Chol oligo); and (C) translation efficiency.

FIG. 14 shows the sequence of the mRNA of Gaussia luciferase (Glue) produced in the Examples (SEQ ID NO: 1). The underlined portion indicates an open reading frame.

FIG. 15 shows the coding sequence of Gaussia luciferase (Glue) used in the Examples (SEQ ID NO: 32).

FIG. 16 shows the sequence of the mRNA of Luc used in the Examples (SEQ IDI NO: 33). The underlined portion indicates an open reading frame.

FIG. 27 is the sequence of the Glue sense strand produced in the Examples (SEQ ID NO: 51). The underlined portion indicates an open reading frame.

FIG. 28 is the sequence of the Gluc antisense strand (with poly U) produced in the Examples (SEQ ID NO: 52).

FIG. 29 is the sequence of the Glue antisense strand (without poly U) produced in the Examples (SEQ ID NO: 53).

FIG. 30 is the sequence of the poly U produced in the Examples (SEQ ID NO: 54).

FIG. 31 is the sequence of the OVA sense strand produced in the Examples (SEQ IDI NO: 55). The underlined portion indicates an open reading frame.

FIG. 32 is the sequence of the poly U produced in the Examples (SEQ ID NO: 56).

FIG. 33 is the coding sequence of Gaussia luciferase (Glue) used in the Examples (SEQ ID NO: 57).

FIG. 34 is the coding sequence of ovalbumin (OVA) used in the Examples (SEQ ID NO: 58).

FIG. 36 shows three poly U sequences produced in the Examples. (A) A method for producing each poly U, and (B) The sequence of each poly U (SEQ ID NOS: 56, 54 and 59, respectively).

FIG. 41 is the sequence of the vector used in the Examples (SEQ ID NO: 65).

DESCRIPTION OF EMBODIMENTS

Hereinafter, the present invention will be described in detail. The following embodiments are provided only for illustrative purpose of explaining the present invention. Thus, the present invention can be carried out in various forms unless it is deviated from the gist thereof. In addition, all publications cited in the present description, for example, prior art documents and patent documents such as published publications and patent publications, are incorporated herein by reference in their entirety. Moreover, the present description includes part or all of the contents as disclosed in the claims, description and drawings of Japanese Patent Application No. 2016-252487 (filed on Dec. 27, 2016) and Japanese Patent Application No. 2016-252488 (filed on Dec. 27, 2016), which are priority documents of the present application.

Herein, provided is a functionalized mRNA, which comprises a double-stranded RNA comprising an mRNA and at least one modified RNA oligomer hybridizing with the mRNA. Hereafter, individual aspects of the functionalized mRNA will be described.

1. First Aspect of the Present Invention

1.1. Summary of First Aspect of the Present Invention

Figure 1:
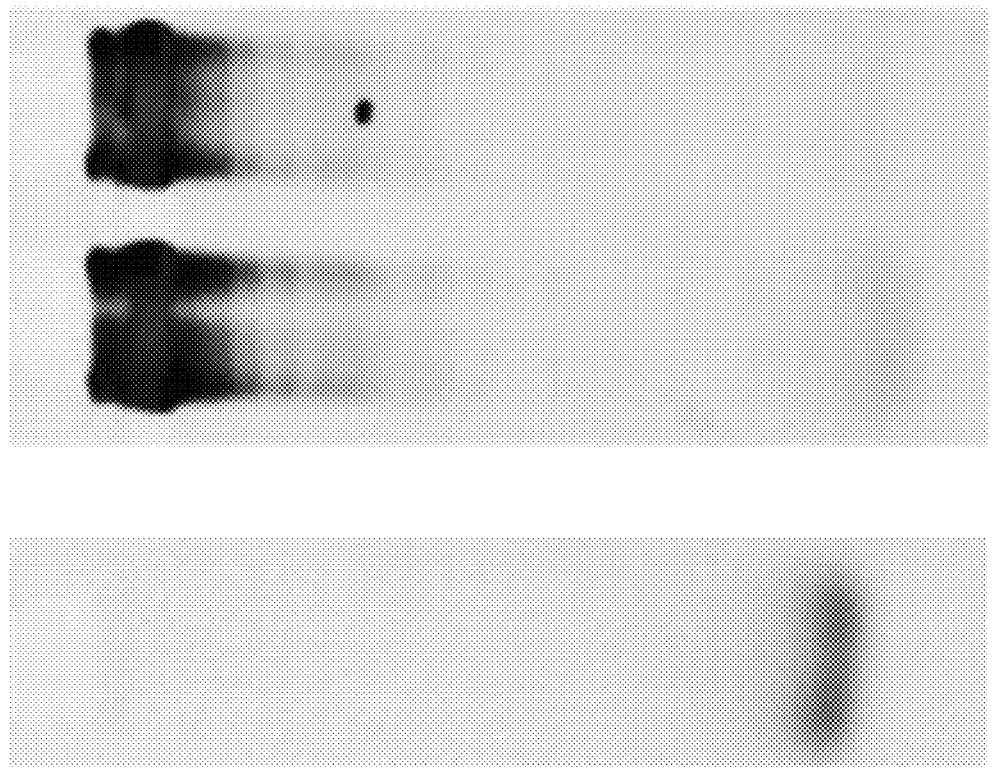
FIG. 1 is an electrophoretic profile showing hybridization of an RNA oligomer with an mRNA. (1) Overhang 2base (1) alone; (2) an mRNA hybridizing with the overhang 2base (1); and (3) an mRNA not hybridizing with the overhang 2base (1).
Figure 2:
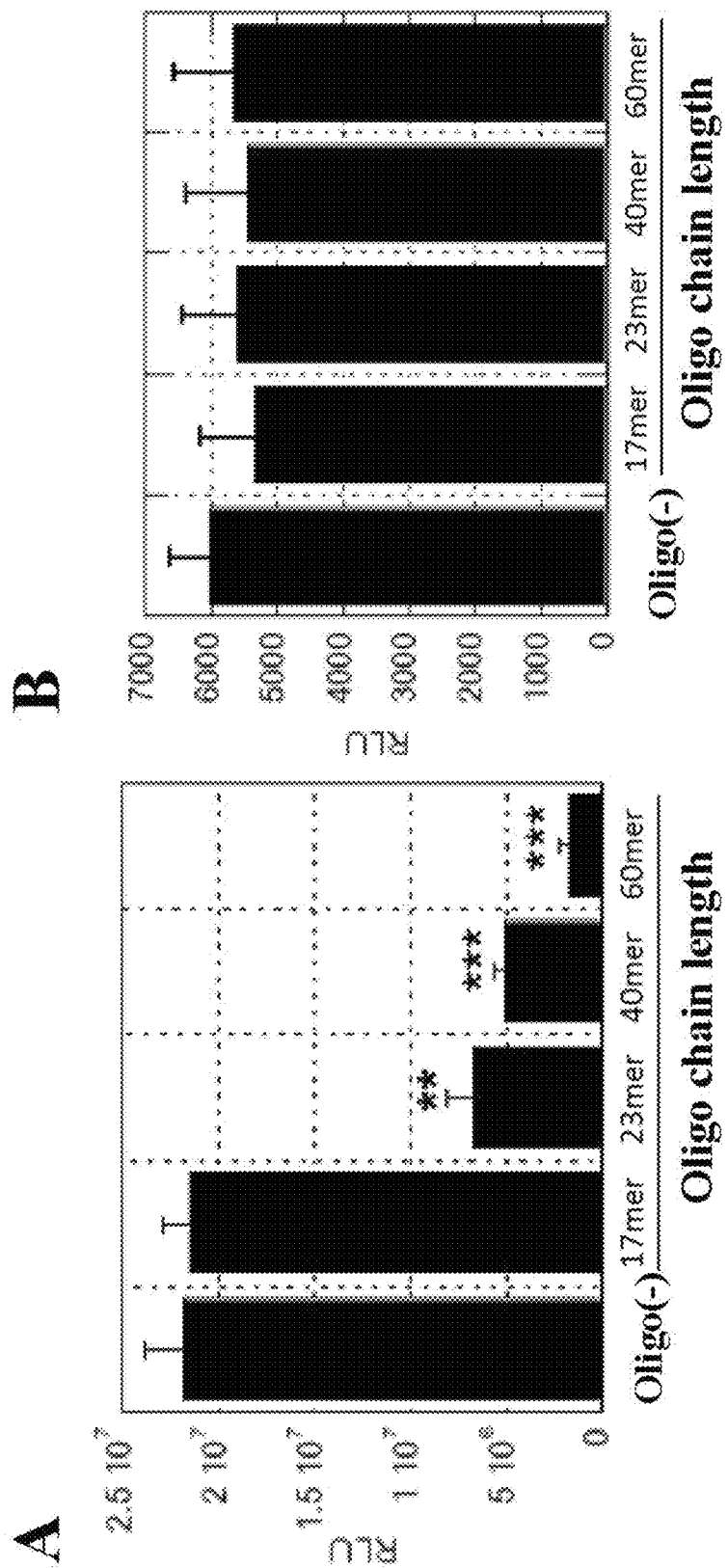
FIG. 2 is a view showing the influence of hybridization of an RNA oligomer with an mRNA. (A) The efficiency of introduction of an mRNA into cultured cells; and (B) protein translation efficiency in a cell-free system.

Regarding a base modification of mRNA, it has been conventionally difficult to design a flexible chemical modification. Hence, the present inventors have considered performing chemical modification on an RNA oligomer having a sequence complementary to an mRNA, and then allowing the RNA oligomer to hybridize with the mRNA, so as to chemically modify the mRNA (FIG. 1). In this case, since the mRNA used here is almost the same as endogenous mRNA, it has been expected that flexible chemical modification can be performed without impairing the translation process. On the other hand, it has been concerned that the translation process would be impaired by performing hybridization. Thus, first, RNA oligomers having various chain lengths were allowed to hybridize with an mRNA, and the influence thereof on translation efficiency was examined. As a result, it was revealed that, as the chain length of the RNA oligomer becomes longer, translation efficiency tends to be decreased. On the other hand, it was found that an RNA oligomer with a length of 17 to 40 nucleotides can sufficiently prevent a decrease in the expression caused by hybridization (FIG. 2). In particular, a decrease in the expression caused by hybridization was hardly found in the case of an oligomer with a length of 17 nucleotides (FIG. 2). From these results, it was found that translation efficiency can be sufficiently maintained by using an RNA oligomer with a length of 12 to 40 nucleotides.

Figure 3:
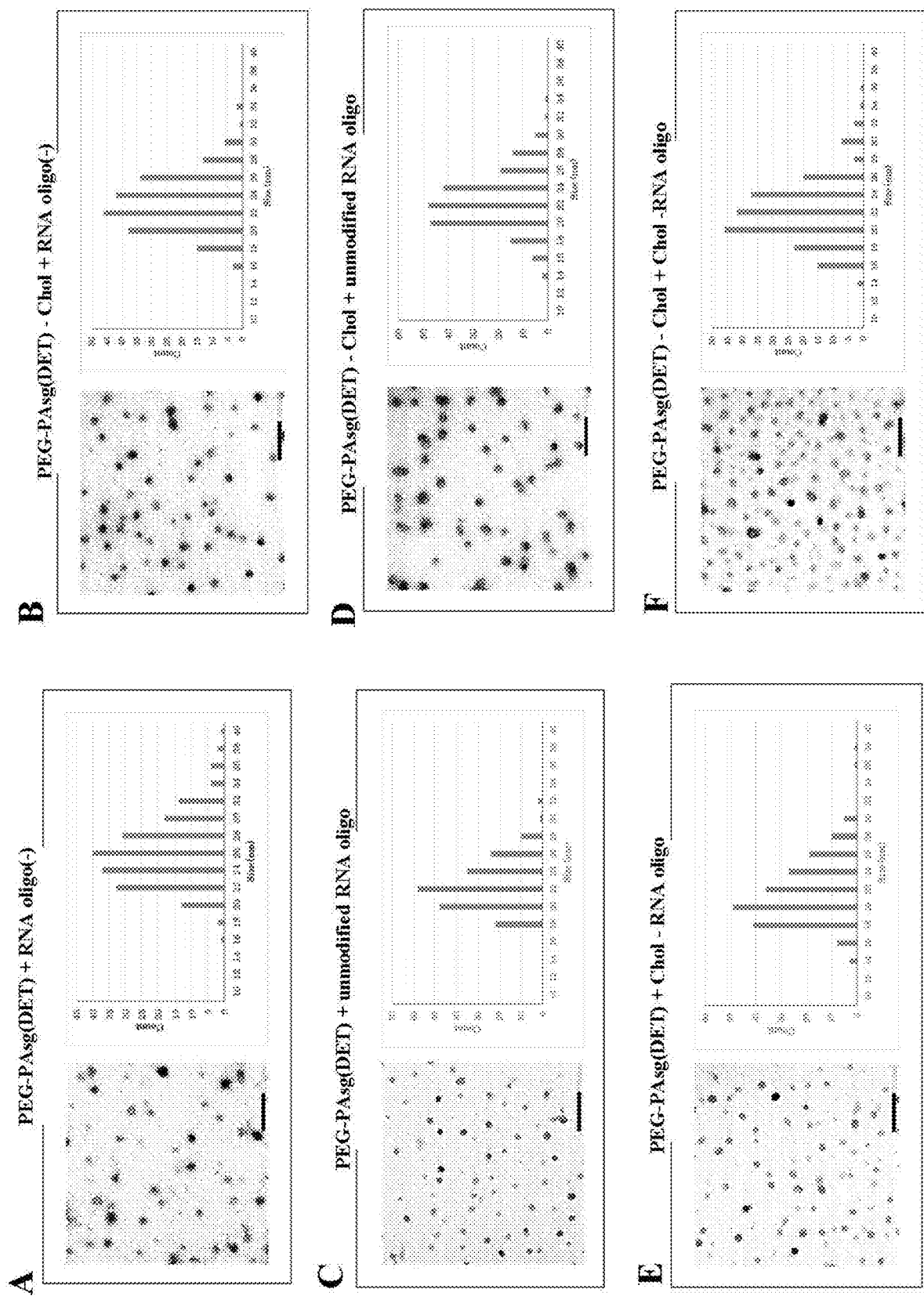
FIG. 3 is a view showing the physicochemical properties of a polymeric micelle loading therein an mRNA hybridizing with an RNA oligomer. (A) PEG-PAsp(DET)+RNA oligo(-); (B) PEG-PAsp(DET)-Chol+RNA oligo(-); (C) PEG-PAsp(DET)+unmodified RNA oligo; (D) PEG-PAsp(DET)-Chol+unmodified RNA oligo; (E) PEG-PAsp(DET)+Chol-RNA oligo; and (F) PEG-PAsp(DET)-Chol+Chol-RNA oligo.
Figure 17:
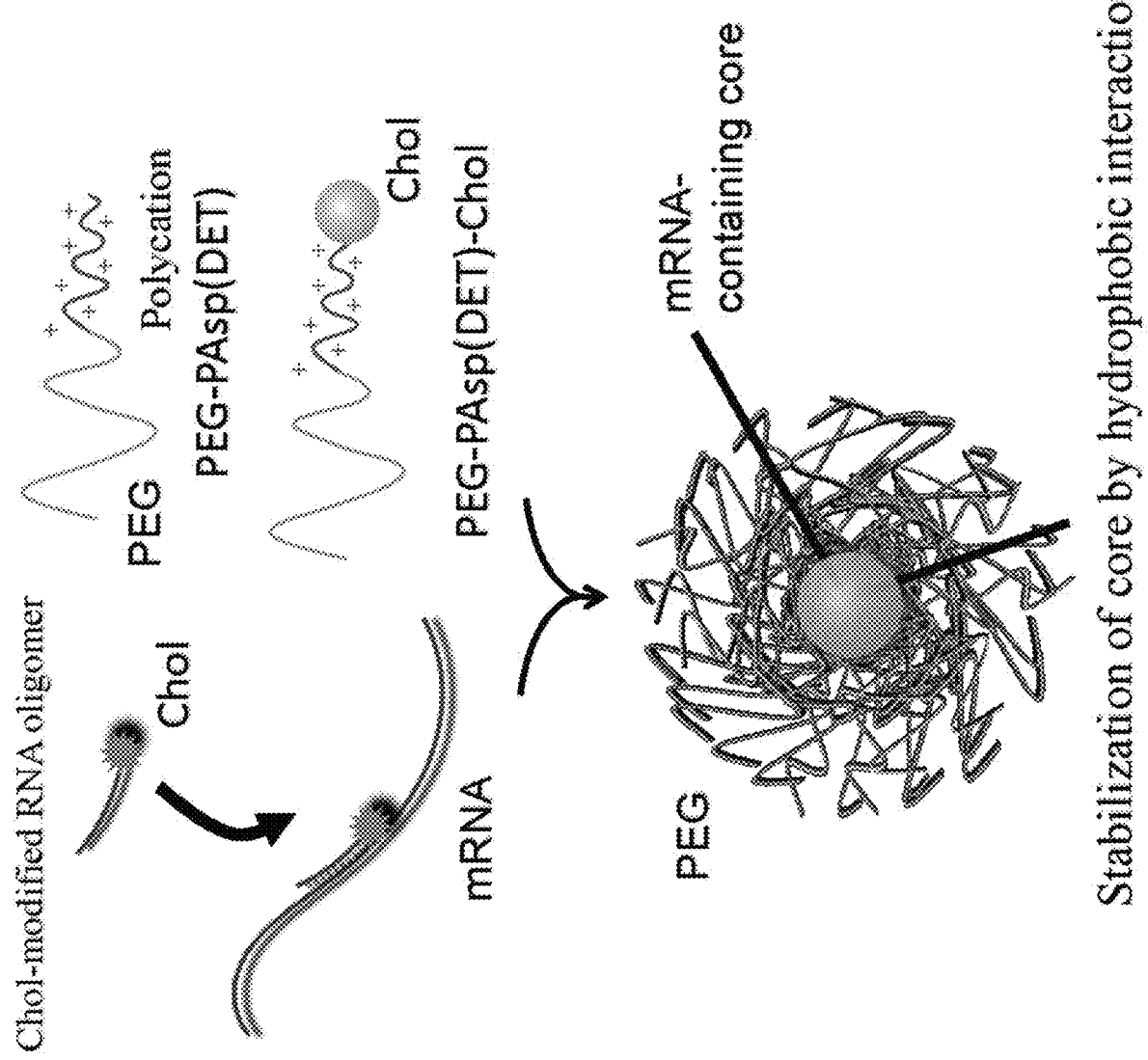
FIG. 17 is a conceptual diagram showing stabilization of an mRNA carrier.

Next, as an example of chemical modification, hybridization of a cholesterol (Chol) modified RNA oligomer was analyzed (FIG. 17). It has been expected that, if Chol modification is performed, an mRNA carrier is stabilized by a hydrophobic interaction when an mRNA is carried on the mRNA carrier, and as a result, enzymatic degradation of the mRNA can be prevented (FIG. 17). As an mRNA carrier, a polymeric micelle coated with a biocompatible polymer, polyethylene glycol (PEG), was used (FIG. 3 and FIG. 17). It was revealed that this polymeric micelle exhibits high safety and high mRNA introduction efficiency, in particular, under in vivo environment.

Figures 1, 4:
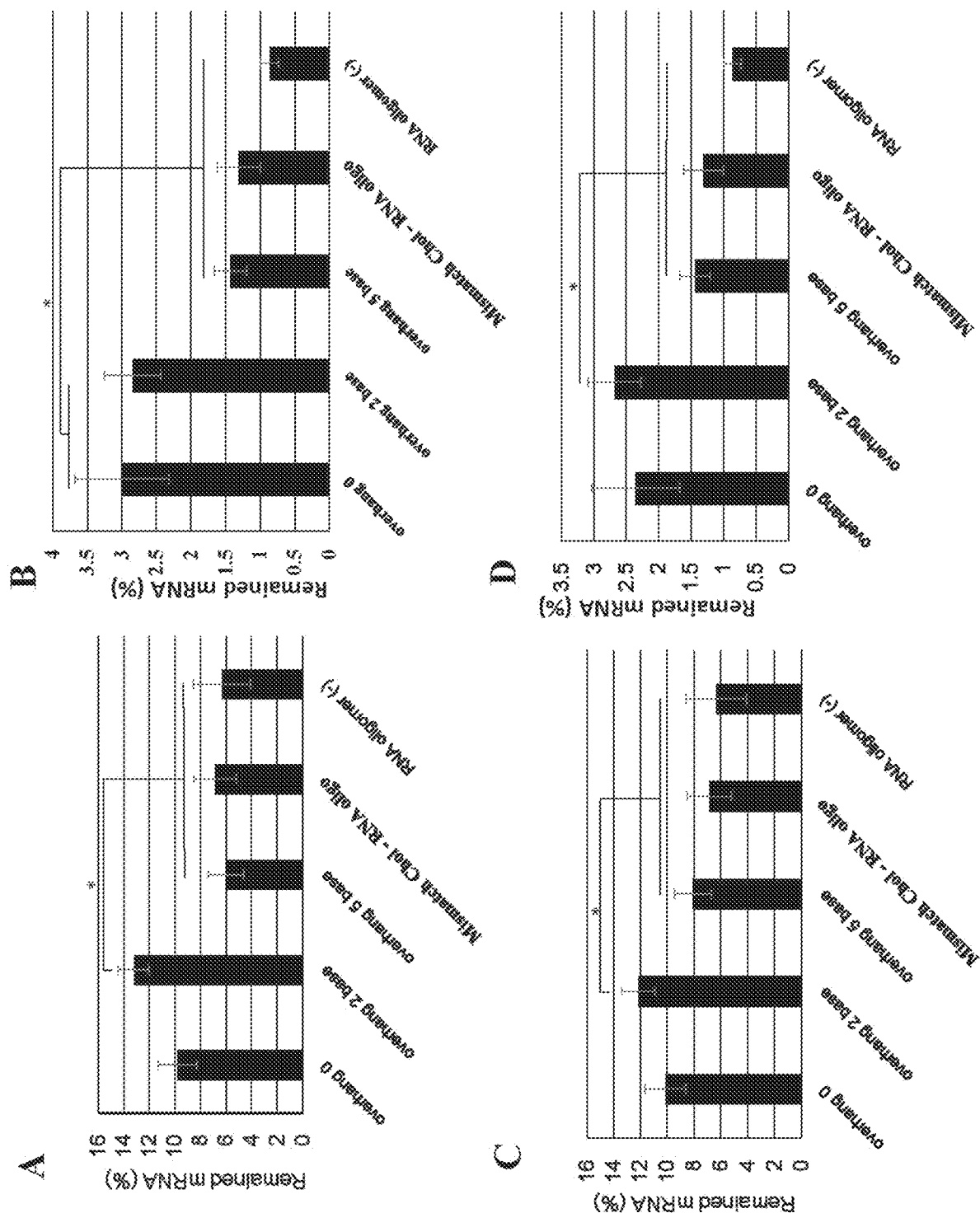
Figures 2, 4:
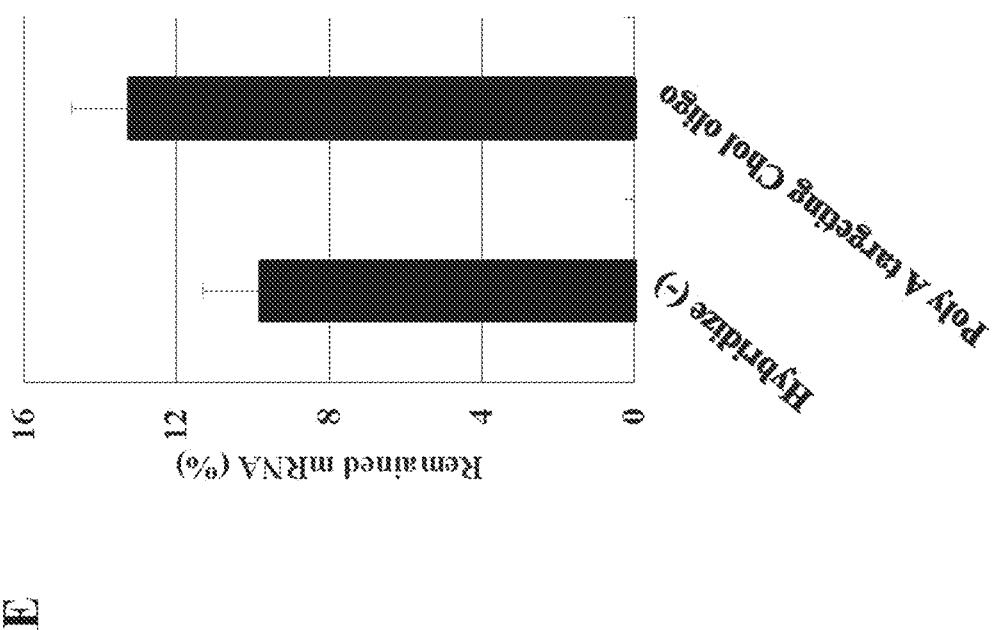
Figure 5:
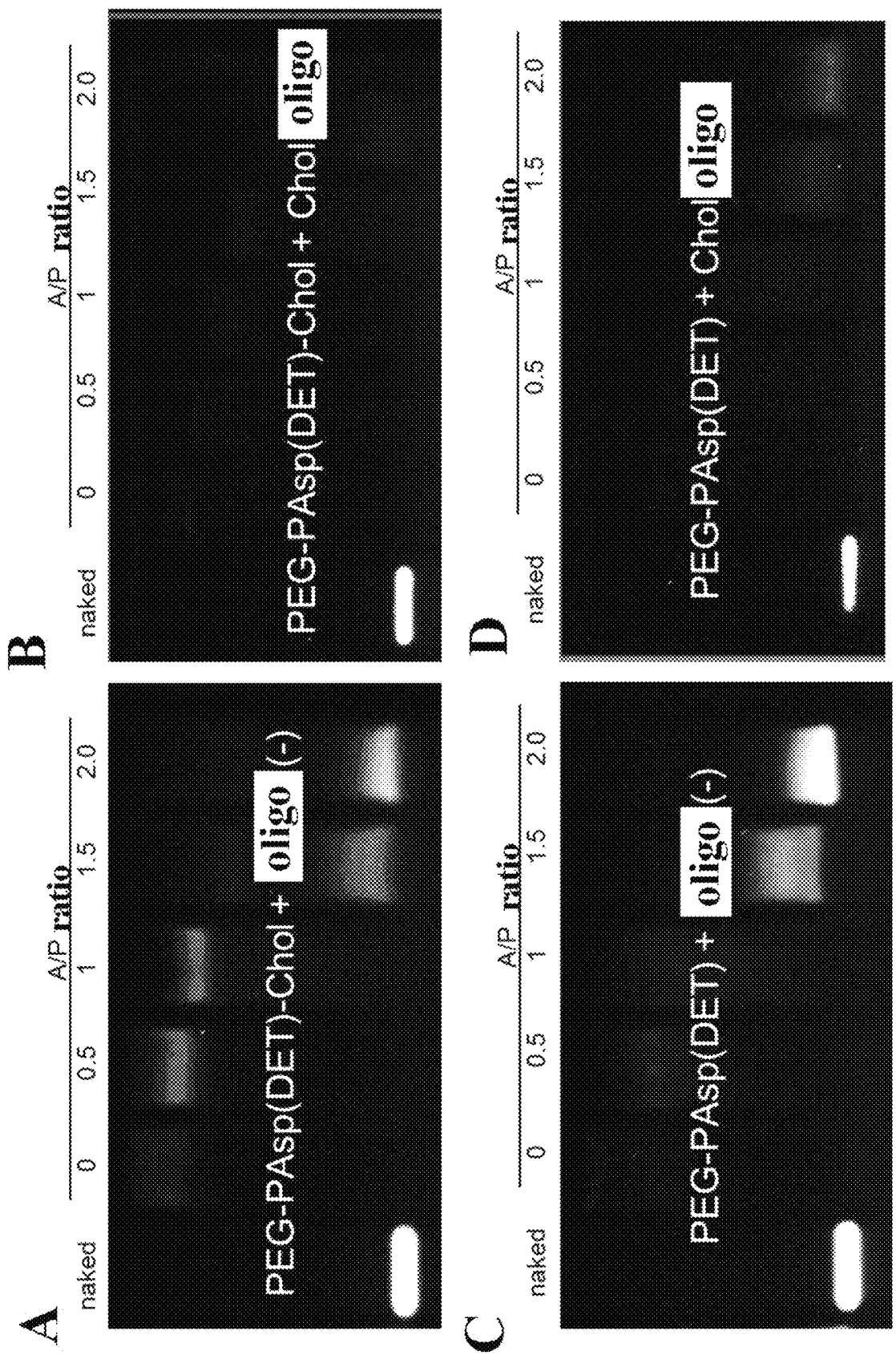
FIG. 5 is a view showing the influence of hybridization of a Chol modified RNA oligomer with an mRNA on stability. (A) PEG-PAsp(DET)-Chol+oligo(-); (B) PEG-PAsp(DET)-Chol+Chol oligo; (C) PEG-PAsp(DET)+oligo(-); and (D) PEG-PAsp(DET)+Chol oligo.
Figure 7:
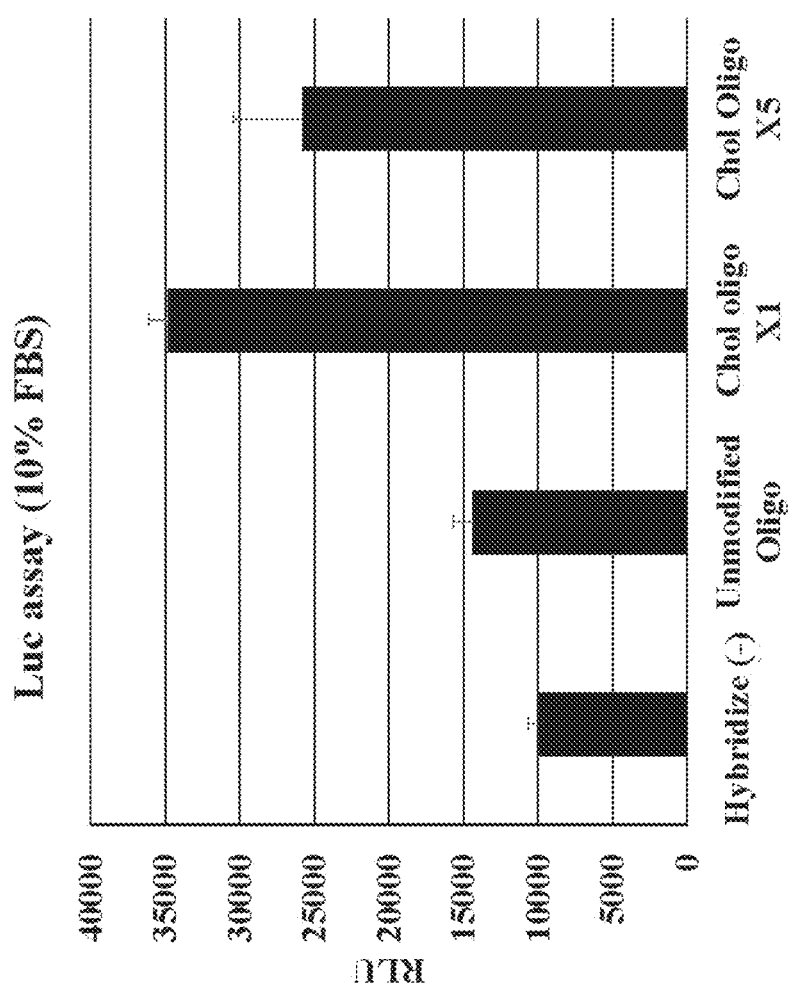
FIG. 7 is a view showing the influence of hybridization of a plurality of Chol modified RNA oligomers with an mRNA on protein translation efficiency upon introduction thereof into cells. Under conditions of 10% (v/v) FBS.
Figure 13:
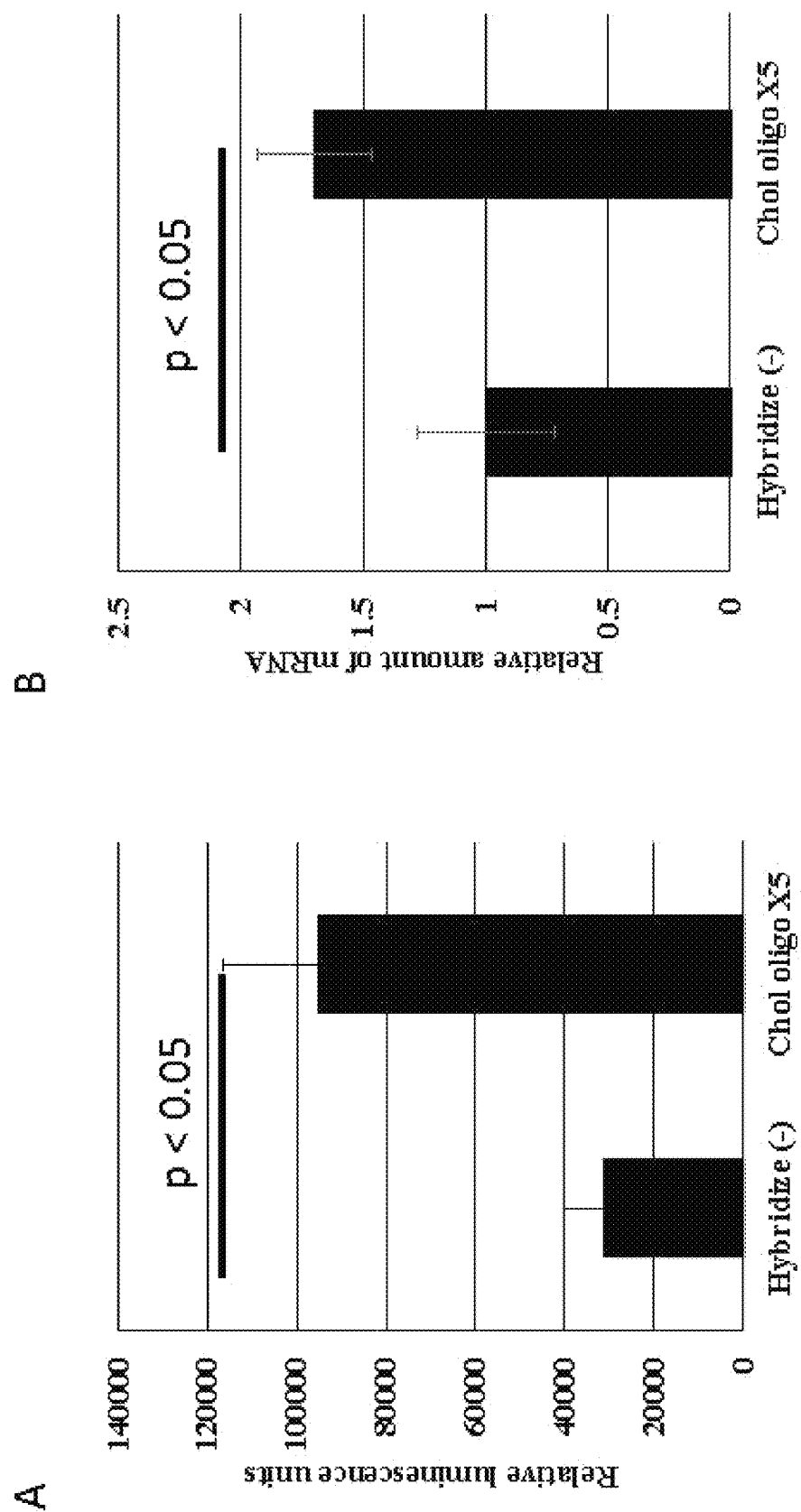
FIG. 13 is a view showing the results of administration of a Chol modified RNA oligomer into the lung. (A) Protein expression efficiency; and (B) the amount of mRNA.

The enzyme resistance of a polymeric micelle comprising an mRNA hybridizing with a Chol modified RNA oligomer in the serum was examined. As a result, it became clear that its enzyme resistance is significantly improved by the hybridization (FIG. 4). Consequently, the present inventors have succeeded in significantly improving the efficiency of introducing the mRNA into cultured cells (FIG. 7). In addition, since polyanions are abundantly present in a living body, the stability of the polymeric micelle in the presence of such polyanions is important. According to the present technique, disintegration of the micelle was actually suppressed (FIG. 5). Moreover, a comparison was made in terms of mRNA introduction efficiency regarding intratracheal administration to mouse lung. In this case also, the effect of improving introduction efficiency was obtained by hybridization (FIG. 13). From these results, it became clear that, according to the first aspect of the present invention, an mRNA-carrying carrier (for example, a polymeric micelle) can be stabilized, and as a result, enzymatic degradation of the mRNA can be suppressed under various environments. Furthermore, the stabilizing effects of such a Chol modified oligomer were obtained in compositions of a plurality of polymeric micelles (FIG. 11), and thus, it can be said that the Chol modified oligomer is a highly versatile platform for improving the enzyme resistance of the mRNA.

Figure 8:
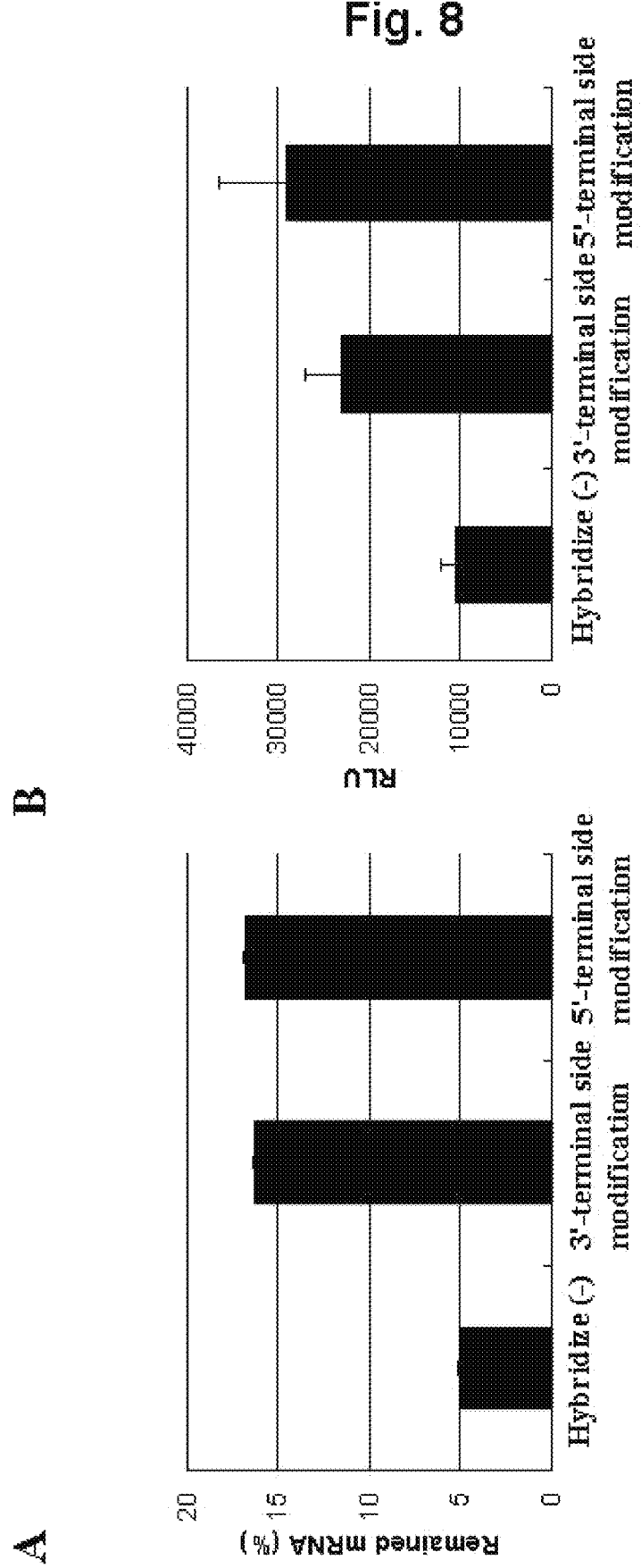
FIG. 8 is a view showing a comparison made between the case of performing Chol modification on the 3'-terminal side of an oligomer, and the case of performing Chol modification on the 5'-terminal side thereof (A) Influence on stability, and (B) protein translation efficiency upon introduction thereof into cells.

Regarding the RNA oligomer, even if either the 5'- or 3'-terminus of the RNA oligomer was modified with a Chol group, it did not largely influence on stability and the efficiency of the expression of a protein from the mRNA (FIG. 8). Moreover, it is also possible to insert a non-hybridizing overhang sequence between the complementary sequence of the RNA oligomer and the Chol group. For example, when a Chol modified block copolymer was used, higher stabilizing effects tended to be obtained in the case of using an overhang sequence consisting of 2 nucleotides, than in the case of not using such an overhang sequence (FIGS. 4(A) and (C)). On the other hand, when a block copolymer that was not modified with Chol was used, more excellent stabilizing effects were obtained without such overhang sequences (FIGS. 4(B) and (D)).

Figure 6:
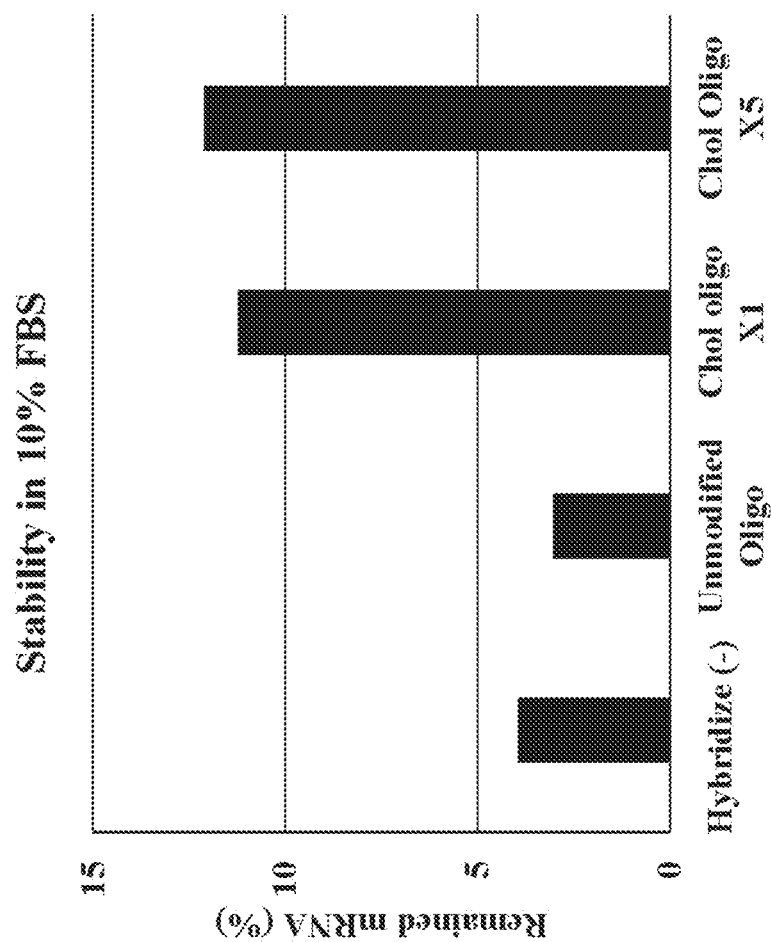
FIG. 6 is a view showing the influence of hybridization of a plurality of Chol modified RNA oligomers with an mRNA on stability. Under conditions of 10% (v/v) FBS.
Figure 9:
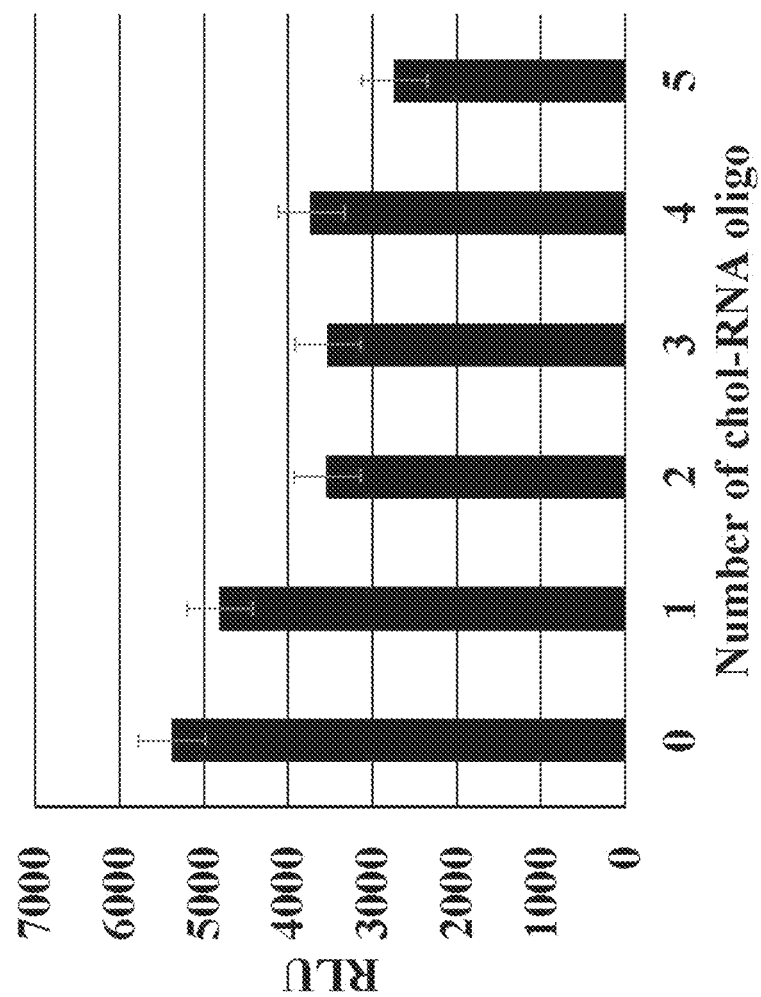
FIG. 9 is a view showing the influence of hybridization of a Chol modified RNA oligomer with an mRNA on protein translation efficiency in a cell-free system.

With regard to the number of Chol modified RNA oligomers hybridizing with the mRNA, even though the number of the RNA oligomers is only one, extremely high stability-improving effects could be obtained. Moreover, as the number of the RNA oligomers was increased, the stability was further improved (FIGS. 6 and 11). On the other hand, as the number of the RNA oligomer was increased, inhibition of mRNA translation was observed by excessive stabilization (FIG. 9). Since the stability required for efficient mRNA delivery is different depending on administration routes, it is considered that the optimal number of Chol modified oligomers is also different depending thereon.

It is considered that chemical modification is performed on the RNA oligomer, and the chemically modified RNA oligomer is then allowed to hybridize with the mRNA, so that the mRNA can be arbitrarily chemically modified. However, since it is concerned that translation efficiency from the mRNA is decreased as a result of the hybridization, no studies have been conducted, so far, regarding that enzymatic degradation of the mRNA is suppressed by hybridization of chemically modified mRNA.

The present inventors have allowed RNA oligomers having various chain lengths to hybridize with an mRNA, and have conducted studies regarding the hybridization. As a result, the inventors have found that an RNA oligomer having a complementary sequence consisting of 12 to 40 nucleotides is favorable as a composition having a chain length capable of forming stable hybridization and not affecting translation efficiency. Moreover, the inventors have also found that, in stabilization of a polymeric micelle by using hybridization of a chemically modified RNA oligomer, the position of the chemical modification is either the 5'-terminus or the 3'-terminus (FIG. 8). Furthermore, the inventors have also found that an overhand sequence may not be between the complementary sequence of the RNA oligomer and a Chol group, or that an overhang sequence consisting of 1 to 5 nucleotides may be between them. By using a chemically modified RNA oligomer having the aforementioned characteristics, relatively high enzymatic degradation-suppressing effects can be obtained. These results are unpredictable from the conventional biological findings.

Further, the first aspect of the present invention relates to a versatile technique capable of suppressing enzymatic degradation of an mRNA in the mRNA itself, or in various carriers (for example, a polymeric micelle).

1.2. Double-Stranded RNA and Carrier

The first aspect of the present invention provides a double-stranded RNA comprising an mRNA encoding a target gene and at least one RNA oligomer hybridizing with the mRNA, wherein the RNA oligomer comprises:

(a) an RNA sequence consisting of a sequence of 12 to 40 nucleotides complementary to the sequence of the mRNA, or (b) an RNA sequence having an identity of 90% or more to a sequence of 12 to 40 nucleotides complementary to the sequence of the mRNA, and hybridizing with the mRNA, and the RNA oligomer is chemically unmodified or is chemically modified.

The double-stranded RNA may be loaded in the carrier. Otherwise, the double-stranded RNA may not be loaded in the carrier, namely, it may be in a naked form. The former first aspect of the present invention provides an mRNA carrier loading therein an mRNA encoding a target gene and at least one RNA oligomer hybridizing with the mRNA, wherein the RNA oligomer comprises:

(a) an RNA sequence consisting of a sequence of 12 to 40 nucleotides complementary to the sequence of the mRNA, or (b) an RNA sequence having an identity of 90% or more to a sequence of 12 to 40 nucleotides complementary to the sequence of the mRNA, and hybridizing with the mRNA, and the RNA oligomer is chemically unmodified or is chemically modified.

The carrier is not particularly limited, as long as it can load a nucleic acid and can deliver it to a preferred site in the body of a subject. The carrier is, for example, a polymeric micelle, a lipidic mRNA carrier, or a cationic polymer complex, and is more preferably a polymeric micelle or a lipidic mRNA carrier.

The polymeric micelle has a two-layer structure consisting of an inner core formed with a condensed nucleic acid and a cationic polymer, and an outer shell formed with a hydrophilic polymer. The cationic polymer is, for example, a polyamino acid derivative. The hydrophilic polymer is, for example, polyethylene glycol ("PEG"). The inner core physically or chemically encapsulates the mRNA therein. The outer shell delivers the mRNA encapsulated in the inner core to predetermined tissues by its physicochemical properties. The polymeric micelle can enter the cells by endocytosis. The polymeric micelle can utilize, for example, the interaction of a polycation with a nucleic acid on a block polymer (polyion complex ("PIC")), and can also utilize a hybrid micelle of the polyion complex with an inorganic molecule. Examples of the PIC-type polymeric micelle may include PIC micelles formed by association of mRNA with PEG-PAsp (DET)-Chol, PEG-PAsp (DET), or PEG-PLys (see the Examples as described later), or other polycations such as PAsp(TET) or PAsp(TEP) used in block copolymers (Uchida, S., et al., Biomaterials (2016) 82, pp. 221-228), and those used in triblock copolymers (Osawa, S., et al., Biomacromolecules 17, pp. 354-361 (2016)). Examples of the hybrid micelle with an inorganic molecule may include PEGylated calcium phosphate (CaP) particles (Pittela, et al., Biomaterials (2011) 32, pp. 3106-3114) and PEGylated silica particles (Miyata, K., et al. Biomaterials (2010) 31, pp. 4764-4770).

The lipidic mRNA carrier is formed using a lipid or a cationic lipid as a carrier, and an mRNA is loaded in or bound to the carrier. The lipidic mRNA carrier is obtained by mixing an mRNA with one or more selected from the group consisting of: for example, cationic lipids such as N-[1-(2, 3-dioleyloxy) propyl]-N,N,N-trimethylammonium chloride (DOTMA), 2,3-dioleyloxy-N-[2-(spermine carboxamido) ethyl]-N, N-dimethyl-1-propanaminium trifluoroacetic acid (DOSPA), 1,2-dioleoyl-3-(trimethylammonium)propane (DOTAP), N-[1-(2,3-dimyristyloxy)propyl]-N,N-dimethyl-N-(2-hydroxyethyl) ammonium bromide (DMRIE), or DC-Cholesterol; neutral phospholipids such as distearoylphosphatidylcholine (DSPC) or dioleoyl phosphatidylethanolamine (DOPE); PEGylated lipids; and cholesterols.

The cationic polymer complex is a mixture of an mRNA and, for example, linear or branched polyethylenimine, polylysine, polyarginine, a chitosan derivative, or a polymethacrylic acid derivative.

These carriers can be prepared by a known method or a method equivalent thereto.

In some aspects, the amount of an mRNA loaded in the carrier is, for example, 0.5 to 200, preferably 1 to 50, and more preferably 1 to 10, in terms of the ratio between the cationic charge (+) in the carrier and the anionic charge (−) of the mRNA (+/−ratio).

A person skilled in the art could appropriately select a target gene, depending on purpose. Examples of the target gene may include a reporter gene, a growth factor gene, a cell growth factor gene, a cell growth suppressor gene, a cell death promoting factor gene, a cell death suppressor gene, a tumor suppressor gene, a transcription factor gene, a genome editing gene, and a vaccine antigen gene. For example, to a subject in need of proliferation of specific cells, a carrier loading an mRNA encoding a growth factor gene for the specific cells is administered, so that the disease or condition of the subject can be treated.

Examples of the reporter may include a luminescent protein and a fluorescent protein.

Examples of the growth factor may include an epidermal growth factor (EGF), an insulin-like growth factor (IGF), a nerve growth factor (NGF), a brain-derived neurotrophic factor (BDNF), a vascular endothelial growth factor (VEGF), a granulocyte colony stimulating factor (G-CSF), a granulocyte-macrophage colony stimulating factor (GM-CSF), a platelet-derived growth factor (PDGF), erythropoietin (EPO), thrombopoietin (TPO), a basic fibroblast growth factor (bFGF or FGF-2), and a hepatocyte growth factor (HGF).

Examples of the cell growth suppressor may include p21, p17, p16, and p53.

Examples of the cell death promoting factor may include Smac/Diablo, an apoptosis inducing factor (AIF), HtrA2, Bad, Bim, Bax, p53, caspase 1, 2, 3, 4, 5, 6, 7, 8, 9 and 10 (e.g., caspases 2, 3, 6, 7, 8, 9 and 10, preferably caspase 3, 6 and 7), Fas ligand (FasL), tumor necrosis factor related apoptosis-inducing ligand (TRAIL), and FoxO1

Examples of the cell death suppressor may include anti-apoptotic factors (e.g., FLIP, Mcl-1, Xiap, crmA, Bcl-2, and Bcl-xL).

Examples of the tumor suppressor gene may include p53, a retinoblastoma gene (Rb), an adenomatous polyposis coli gene (APC), a neurofibromatosis type 1 gene (NF1), a neurofibromatosis type 2 gene (NF2), WT1, VHL, BRCA1, BRCA2, CHEK2, maspin, p73, Smad4, MSH2, MLH1, PMS2, DCC, phosphatase tensin homolog (PTEN), SDHD, p16, p57$^{Kip2}$, PTC, TSC1, TSC2, EXT1, and EXT2.

Examples of the transcription factor may include Runt-related transcription factor 1 (Runx1), p53, c-fos, c-Jun, CREB, C/EBP, MyoD, c-Myc, c-Myb, Oct3/4, NF-κB, NF-AT, Mef-2, and an extracellular signal response factor (SRF).

Examples of the genome editing gene may include zinc finger nuclease (ZNF), transcription activator like effector nuclease (TALEN), and a clustered, regularly interspaced, short palindromic repeat (CRISPR)/CRISPR-associated (Cas) 9 gene.

Examples of the vaccine antigen gene may include a pathogen antigen and a tumor specific antigen.

The term "mRNA" means a messenger RNA, and the mRNA generally comprises a 5' untranslated region (5' UTR), a coding region, and a 3' untranslated region (3' UTR). In general, the mRNA further comprises a cap structure at the 5'-terminus (5' Cap) and a poly A sequence at the 3'-terminus.

The mRNA used herein may be any one of the following mRNAs.

(1) mRNA comprising 5' Cap, 5' UTR, a coding region, 3' UTR, and poly A in this order.

(2) mRNA comprising 5' Cap, 5' UTR, coding region, and poly A in this order.

(3) mRNA comprising 5' UTR, a coding region, 3' UTR, and poly A in this order.

(4) mRNA comprising 5' UTR, a coding region, and poly A in this order.

(5) mRNA comprising 5' Cap, 5' UTR, a coding region, and 3' UTR in this order.

(6) mRNA comprising 5' Cap, 5' UTR, and a coding region in this order.

(7) mRNA comprising 5' UTR, a coding region, and 3' UTR in this order.

(8) mRNA comprising 5' UTR and a coding region in this order.

The mRNA encoding a target gene can be produced by transcribing a template DNA encoding the target gene under in vitro environment according to a known method. For example, the mRNA encoding a target gene can be produced according to the method described in Blood 108 (13) (2006) 4009-17. Specifically, a template DNA, in which a poly A/T strand is incorporated downstream of a protein coding sequence, is cleaved immediately downstream of the poly A/T strand, and is then subjected to in vitro transcription in a buffer solution containing translation enzymes, nucleosides and 5' Cap analogs. Thereafter, the mRNA is purified, so as to produce an mRNA encoding a target gene. A more specific method of preparing an mRNA is as described in the after-mentioned Examples.

In some aspects, chemical modification is not performed on the nucleotides of the mRNA itself. In this case, since the mRNA used here is almost the same as endogenous mRNA, it can be expected that the translation process is hardly impaired. In some other aspects, chemical modification is performed on the nucleotides of the mRNA itself. It has been known that chemical modification performed on the nucleotides of the mRNA itself, for example, can improve the enzyme resistance of the mRNA or can reduce immunogenicity. Examples of the chemically modified nucleotides of the mRNA itself may include methylated nucleotides (e.g., 5-methylcytosine), sulfur modified nucleotides (e.g., 2-thiouridine), pseudouridine, Nl methyl pseudouridine, and 5-methoxy-uridine.

The RNA oligomer is an RNA strand comprising:

(a) an RNA sequence consisting of a sequence of 12 to 40 nucleotides complementary to the sequence of the mRNA, or (b) an RNA sequence having an identity of 90% or more to a sequence of 12 to 40 nucleotides complementary to the sequence of the mRNA, and hybridizing with the mRNA.

The range of "90% or more" in the "RNA sequence having an identity of 90% or more" is, for example, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more. In general, the numerical value of the above-described identity is preferable, as the numerical value increases. Besides, the identity of RNA sequences can be determined using analysis software such as BLAST (see, for example, Altzshul S. F. et al., J. Mol. Biol. 215, 403(1990)). In the case of using BLAST, the default parameters of each program are used.

The phrase "hybridize with the mRNA" means that the RNA oligomer hybridizes with the mRNA under the after-mentioned hybridization conditions.

The RNA oligomer is designed to hybridize with the sequence of the mRNA consisting of consecutive 12 to 40 nucleotides. In some aspects, the sequence of the RNA oligomer consists of a sequence of 12 to 30 nucleotides that is complementary to the sequence of the mRNA. More preferably, the sequence of the RNA oligomer consists of a sequence of 15 to 23 nucleotides that is complementary to the sequence of the mRNA. Further preferably, the sequence of the RNA oligomer consists of a sequence of 17 nucleotides that is complementary to the sequence of the mRNA.

The position in the mRNA, with which the RNA oligomer is allowed to hybridize, is any position of 5' UTR, a coding region, 3' UTR, and a poly A sequence. The RNA oligomer is desirably designed, such that it predicts the secondary structure of the mRNA, and hybridizes with a portion of the mRNA strand that does not have the secondary structure. That is to say, the RNA oligomer is preferably designed to hybridize with a portion not having the secondary structure in the entire mRNA sequence. The software that predicts the secondary structure of the mRNA is, for example, the one described in the Examples later.

In some aspects, the RNA oligomer is designed to hybridize with the poly A sequence of the mRNA.

Chemical modification of an oligo RNA may be carried out without mediation of an overhang sequence, or may also be carried out with mediation of an overhang sequence. Herein, the term "overhang sequence" means a sequence that does not hybridize with the mRNA.

When chemical modification is performed without mediation of an overhang sequence, an oligo RNA preferably consists of only the above-described RNA sequence (a) or (b). In this case, chemical modification is performed, for example, on the 5'-terminus or 3'-terminus of the sequence of the RNA oligomer. In some aspects, when the carrier is not modified with a hydrophobic group (e.g., a block copolymer that is not modified with a hydrophobic group), chemical modification of an oligo RNA is performed without mediation of an overhang sequence.

On the other hand, when chemical modification is performed with mediation of an overhang sequence, an oligo RNA preferably consists of the above-described RNA sequence (a) or (b) and an overhang sequence. In this case, chemical modification is performed on the 5'-terminus or 3'-terminus of the above-described RNA sequence (a) or (b) of the RNA oligomer, with mediation of an overhang sequence consisting of 1 to 5 nucleotides. When chemical modification is performed with mediation of an overhang sequence, the chain length of the overhang sequence is preferably 1 to 4 nucleotides, more preferably 1 to 3 nucleotides, and further preferably 2 nucleotides. If the chain length of the overhang sequence is 1 to 5 nucleotides, relatively high mRNA stabilizing effects can be expected. In some aspects, when the carrier is modified with a hydrophobic group (e.g., a block copolymer modified with a hydrophobic group), chemical modification of an oligo RNA is performed on the 5'-terminus or 3'-terminus of the above-described RNA sequence (a) or (b) of the RNA oligomer, with mediation of an overhang sequence consisting of 1 to 5 nucleotides.

Regarding the RNA oligomer, chemical modification may be performed on either the 5'-terminus or the 3'-terminus of the above-described RNA sequence (a) or (b), with mediation of the overhang sequence. Herein, the RNA oligomer chemically modified with mediation of the overhang sequence may also be referred to as a "chemically modified oligomer" at times.

Chemical modification is, for example, modification capable of stabilizing a naked double-stranded RNA or mRNA carrier. Examples of such chemical modification may include modification with a hydrophobic group and modification with polyethylene glycol. Examples of the modification with a hydrophobic group may include cholesterol modification and tocopherol modification. If the modification with a hydrophobic group is performed, when an mRNA is carried on an mRNA carrier, the carrier is stabilized by hydrophobic interaction, and as a result, it can be expected that enzymatic degradation of the mRNA can be prevented. In some aspects, the modification with a hydrophobic group is cholesterol modification. The modification with a hydrophobic group can be carried out, for example, by the phosphoroamidite method described in S. L. Beaucage, et al., Tetrahedron Letters (1981) 22, pp. 1859-1862, or a method equivalent thereto. For example, the modification with a hydrophobic group can be carried out as follows. After the synthesis of an RNA oligomer, an amidited hydrophobic group is allowed to react with the 5'-terminal OH group of the RNA oligomer, so as to obtain an RNA oligomer, into the 5'-terminus of which the hydrophobic group has been introduced. Alternatively, an RNA is synthesized from the hydrophobic group of the terminal OH group according to the phosphoroamidite method, so as to obtain an RNA oligomer, into the 3'-terminus of which the hydrophobic group has been introduced.

It is to be noted that the definition of "chemical modification" does not include the triphosphoric acid structure at the 5'-terminus.

If the modification with polyethylene glycol (PEG) is performed, when an mRNA is carried on an mRNA carrier, the carrier is coated with a polyethylene glycol chain, and is stabilized by the stealth properties. In addition, the surface potential is reduced by the shielding effects of the polyethylene glycol chain, and recognition of the mRNA by an RNA-degrading enzyme that is a cationic protein can be suppressed. Consequently, it can be expected that enzymatic degradation of the mRNA can be prevented. The modification with polyethylene glycol can be carried out, for example, by the method described in the publication M. Oishi, et al., Chem Bio Chem 6(4), 2005, 718-725, or a method equivalent thereto. More specifically, an RNA oligomer is synthesized using an initiator such as DMS(O)MT-AMINO-MODIFIER (GLENRESERCH), and is then deprotected to obtain an RNA oligomer with an aminated 5'-terminus. This RNA oligo with an aminated 5'-terminus is allowed to react, for example, with PEG-N-hydroxysuccinimide to obtain a PEGylated RNA oligomer. Examples of the polyethylene glycol used herein may include linear PEG having a weight average molecular weight of 1,000 to 80,000, and branched PEG having the same weight average molecular weight as above, such as 2-branched, 4-branched, or 8-branched PEG.

The number of chemically unmodified RNA oligomers or chemically modified RNA oligomers to be allowed to hybridize with the mRNA is at least one, preferably 1 to 50, more preferably 1 to 15, and further preferably 1 to 5. As the number of the RNA oligomers is increased, the stability of the mRNA is further improved. When the number of the RNA oligomers is 1 to 50, the translation efficiency of the mRNA can be maintained at a relatively high level.

When a plurality of chemically unmodified RNA oligomers or chemically modified RNA oligomers are allowed to hybridize with the mRNA, in some aspects, the chemically unmodified RNA oligomers or chemically modified RNA oligomers are designed not to be overlapped with one another on the mRNA.

Hybridization of the RNA oligomer(s) with the mRNA can be carried out by applying a known method and known conditions. In the hybridization, the reaction mixture is heated and is then left at rest for a certain period of time, and thereafter, the temperature is gradually decreased. The heating is carried out for the purpose of dissociating complementary bonds previously existing in the molecules of the mRNA or the oligomer(s), or among the molecules thereof, and thereby more efficiently binding the mRNA with the oligomer(s). The temperature and the time can be adjusted, as appropriate, as long as suitable hybridization can be guaranteed. Moderate temperature decrease brings on an increase in the hybridization specificity. In addition, the chain length of the oligomer does not largely influence on determination of hybridization conditions. Hybridization conditions should be determined, as appropriate, while evaluating hybridization efficiency. For example, the methods and conditions described in the Examples later are applied.

Moreover, the first aspect of the present invention provides a method for stabilizing an mRNA, comprising allowing an mRNA encoding a target gene to hybridize with at least one RNA oligomer to obtain a double-stranded RNA, wherein the RNA oligomer comprises:

(a) an RNA sequence consisting of a sequence of 12 to 40 nucleotides complementary to the sequence of the mRNA, or (b) an RNA sequence having an identity of 90% or more to a sequence of 12 to 40 nucleotides complementary to the sequence of the mRNA, and hybridizing with the mRNA, and the RNA oligomer is chemically unmodified or is chemically modified.

In the stabilization method, the mRNA that has hybridized with the chemically unmodified RNA oligomer(s) or the chemically modified RNA oligomer(s) may be loaded in a carrier. Otherwise, the mRNA that has hybridized with the chemically unmodified RNA oligomer(s) or the chemically modified RNA oligomer(s) may not be loaded in a carrier, namely, the mRNA may be in a naked form. Preferably, the mRNA that has hybridized with the chemically unmodified RNA oligomer(s) or the chemically modified RNA oligomer(s) may be loaded in a carrier. The former first aspect of the present invention also provides a method for stabilizing a carrier, comprising allowing a carrier to load therein an mRNA encoding a target gene and at least one RNA oligomer hybridizing with the mRNA, wherein the RNA oligomer comprises:

(a) an RNA sequence consisting of a sequence of 12 to 40 nucleotides complementary to the sequence of the mRNA, or (b) an RNA sequence having an identity of 90% or more to a sequence of 12 to 40 nucleotides complementary to the sequence of the mRNA, and hybridizing with the mRNA, and the RNA oligomer is chemically unmodified or is chemically modified.

The mRNA, RNA oligomer, carrier, chemical modification, and the like, which are used in the stabilization method, are as those described in the explanation regarding the above-described carrier.

1.3. Pharmaceutical Composition

The first aspect of the present invention provides a pharmaceutical composition comprising the above-described double-stranded RNA or carrier. The pharmaceutical composition is used to deliver an mRNA or a carrier loading the mRNA therein into the body of a subject.

The "subject" is a human, or an organism other than the human, such as, for example, birds and non-human mammals (e.g., bovines, monkeys, cats, mice, rats, Guinea pigs, hamsters, pigs, dogs, rabbits, sheep and horses).

The pharmaceutical composition can be administered to the subject via intravenous administration, intraarterial administration, oral administration, intratissue administration (e.g., intravesical administration, intrathoracic administration, intraperitoneal administration, intraocular administration, and intracerebral administration), transdermal administration, transmucosal administration, transpulmonary administration, or transrectal administration. In particular, intravenous administration, transdermal administration, and transmucosal administration are desirable. Dosage forms suitable for these administrations are, for example, various injections, oral agents, infusions, inhalants, eye drops, ointments, lotions, and suppositories. Administration conditions, such as applied dose, the number of administrations and administration period, can be determined, as appropriate, by a person skilled in the art, while taking into consideration the type of the mRNA, dosage form, the conditions of the subject, such as age or bodyweight, administration route, and the properties or degree of the disease.

The pharmaceutical composition can be used in a treatment of introducing an mRNA encoding a desired gene into cells causing various types of diseases. Accordingly, the first aspect of the present invention can also provide a method for treating various types of diseases, comprising administering the pharmaceutical composition to a subject in need of the treatment of various types of diseases. It is to be noted that various conditions such as applied dose, the number of administrations and administration period are the same as those described above.

Examples of various diseases to be treated with the pharmaceutical composition may include cancers, viral diseases, metabolic diseases, circulatory diseases, neurological diseases, renal urinary diseases, hematologic malignancies, diseases desiring promotion or suppression of apoptosis, collagen diseases, respiratory diseases, and gastrointestinal diseases.

For the pharmaceutical composition, agents that are commonly used in drug manufacturing, such as excipients, fillers, thickeners, binders, wetting agents, disintegrators, lubricants, surfactants, dispersants, buffers, preservatives, solubilizing agents, antiseptics, flavoring agents, soothing agents, stabilizers, and isotonic agents, may be appropriately selected and used, and the pharmaceutical composition can be prepared according to a conventional method, using these agents. When an intravenous injection (including infusion) is produced for example, it is provided in the state of a unit dose ampule, a multi-dose container, or the like.

In some aspects, while taking into consideration the type of the mRNA, dosage form, the conditions of the subject, such as age or bodyweight, administration route, and the properties or degree of the disease, in general, the applied dose of the mRNA is, for example, in the range of 0.1 mg to 5 g/human adult per day, and preferably in the range of 1 mg to 2 g/human adult per day. The applied dose may be different depending on the type of a target disease, administration form, and a target molecule in some cases. Accordingly, the applied dose is sufficient, even if it is less than the aforementioned dose in some cases. In contrary, the dose that is greater than the aforementioned range is necessary in some other cases. In addition, the pharmaceutical composition can be administered once or divided over several administrations per day, or with intervals of one to several days.

1.4. Kit for mRNA Delivery

The kit for mRNA delivery according to the first aspect of the present invention is characterized in that it includes the above-described mRNA hybridizing with the chemically unmodified RNA oligomer or chemically modified RNA oligomer. The mRNA hybridizing with the chemically unmodified RNA oligomer or chemically modified RNA oligomer may be loaded in a carrier. Alternatively, the mRNA hybridizing with the chemically unmodified RNA oligomer or chemically modified RNA oligomer may not be loaded in a carrier, namely, the mRNA may be in a naked form. Preferably, the mRNA hybridizing with the chemically unmodified RNA oligomer or chemically modified RNA oligomer is loaded in a carrier. The former kit for mRNA delivery of the first aspect of the present invention is characterized in that it includes a carrier. The present kit can be preferably used, for example, in a method for treating various diseases, in which the above-described mRNA hybridizing with the chemically unmodified RNA oligomer or chemically modified RNA oligomer, or carrier is used.

In the kit, the storage state of the mRNA hybridizing with the chemically unmodified RNA oligomer or chemically modified RNA oligomer, or the carrier is not limited. Taking into consideration stability (storability), the ease of use, etc., the state of a solution, powder or the like can be selected.

The kit may include other components, as well as the above-described mRNA hybridizing with the chemically unmodified RNA oligomer or chemically modified RNA oligomer, or carrier. Examples of such other components may include various types of buffers and an instruction manual (use manual).

2. Second Aspect of the Present Invention 2.1. Summary of Second Aspect of the Present Invention Since the mRNA itself has low immunogenicity, it hardly provokes an inflammatory response. As such, the conventional vaccine using a single-stranded mRNA has been inevitably used together with an adjuvant for effectively provoking an inflammatory response.

Herein, it has been known that a double-stranded RNA induces a stronger inflammatory response. Hence, the present inventors have considered allowing a single-stranded mRNA encoding an antigenic protein to hybridize with an RNA strand having a sequence complementary to the mRNA ("complementary strand RNA"), so that the mRNA is administered to a subject in the form of a double-stranded RNA. By controlling the complementary strand RNA and suppressing the expression of a protein therefrom, it can be expected that both the expression of a protein of interest from the double-stranded RNA and sufficient immune induction can be simultaneously achieved. Moreover, since the RNA molecule itself is present in a living body and a foreign matter is not used, it is considered that relatively high safety is guaranteed when such a double-stranded RNA is used.

When a complementary strand RNA was allowed to hybridize with the full length of mRNA, an extremely strong inflammatory response was observed, in comparison to a non-hybridizing mRNA (FIG. 23(A)), but the efficiency of the expression of a protein from the mRNA was reduced to 1/100 or lower (FIG. 23(B)). Hence, the present inventors have considered partial hybridization of a shorter complementary strand. When a complementary strand RNA was allowed to hybridize with a coding sequence as a site at which a double strand is to be formed, protein expression efficiency was decreased. However, when a complementary strand (poly U) was allowed to mainly hybridize with a poly A sequence added at the 3'-terminus, it was found that protein expression efficiency was hardly decreased (FIG. 23(B)), and a strong inflammatory response was provoked (FIG. 23(A)).

Hence, the second aspect of the present invention provides an mRNA vaccine, which comprises a double-stranded RNA consisting of an mRNA encoding an antigen and at least one RNA oligomer hybridizing with at least the poly A sequence of the mRNA, wherein the at least one RNA oligomer is chemically unmodified or is chemically modified. The mRNA vaccine of the second aspect of the present invention can achieve both highly efficient protein expression and immune induction ability.

Figure 25:
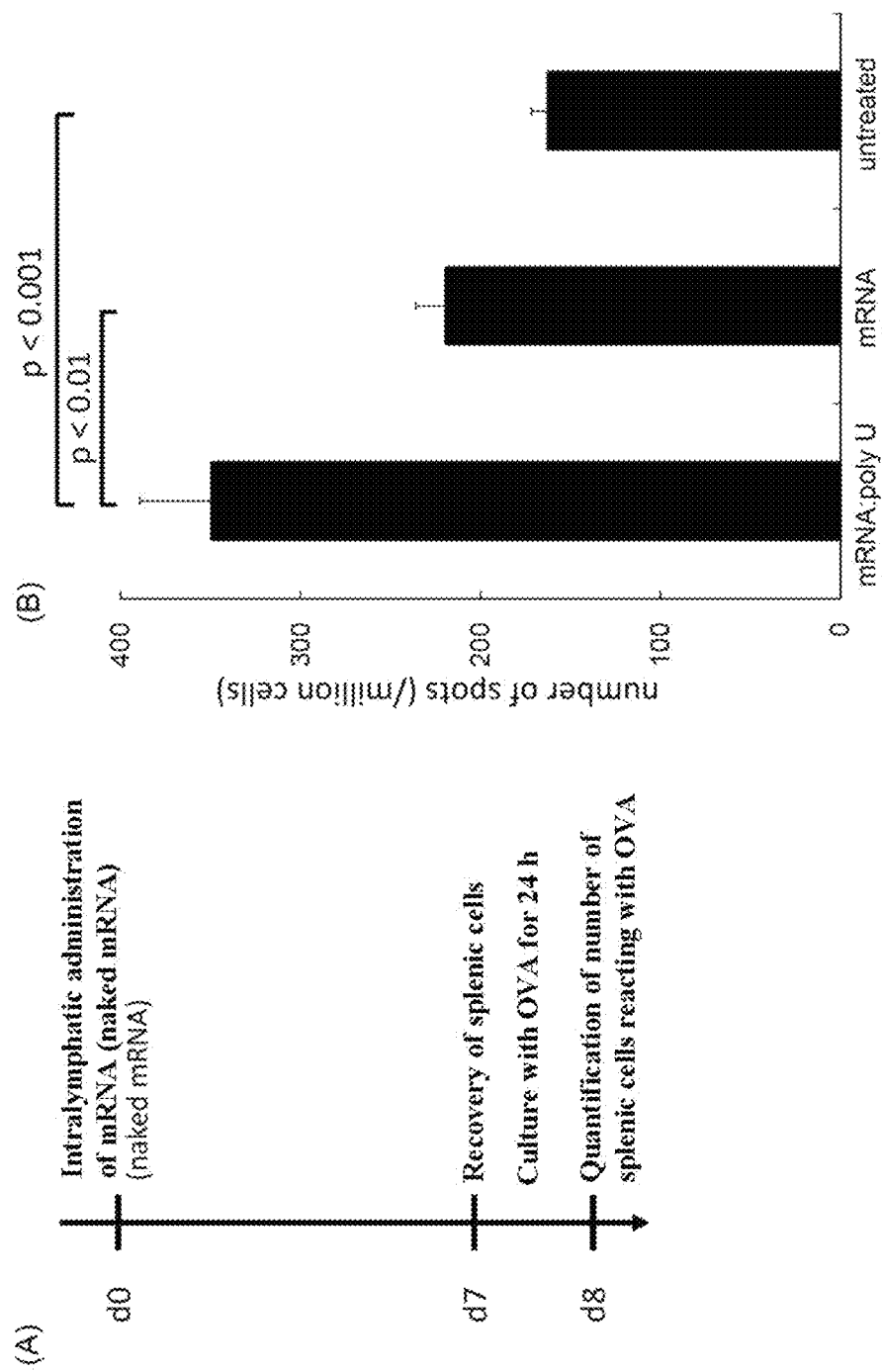
FIG. 25 is a view showing the results of administration of a double-stranded RNA to mice. (A) Procedures from administration to quantification of the number of cells, and (B) the number of IFN-γ-producing cells.

With regard to whether the effects of a vaccine can be actually improved by using the mRNA vaccine of the second aspect of the present invention, immune induction ability in mice was evaluated, focusing on cellular immunity (FIG. 25(A)). Herein, ovalbumin (OVA) was used as a model antigen, and an OVA expression mRNA was administered into the inguinal lymph nodes of mice. Subsequently, the spleen cells were recovered one week after the administration of the mRNA, and the number of cells specifically reacting with OVA was evaluated according to an ELISPOT assay. As a result, it became clear that when the mRNA was administered into the lymph nodes, an mRNA having a poly A sequence hybridizing with a complementary strand RNA (poly U) significantly strongly induced antigen-specific cellular immunity, in comparison to a non-hybridizing mRNA (FIG. 25(B)). Thus, it was demonstrated that cellular immune induction effects are improved by using the mRNA vaccine of the second aspect of the present invention.

Figure 26:
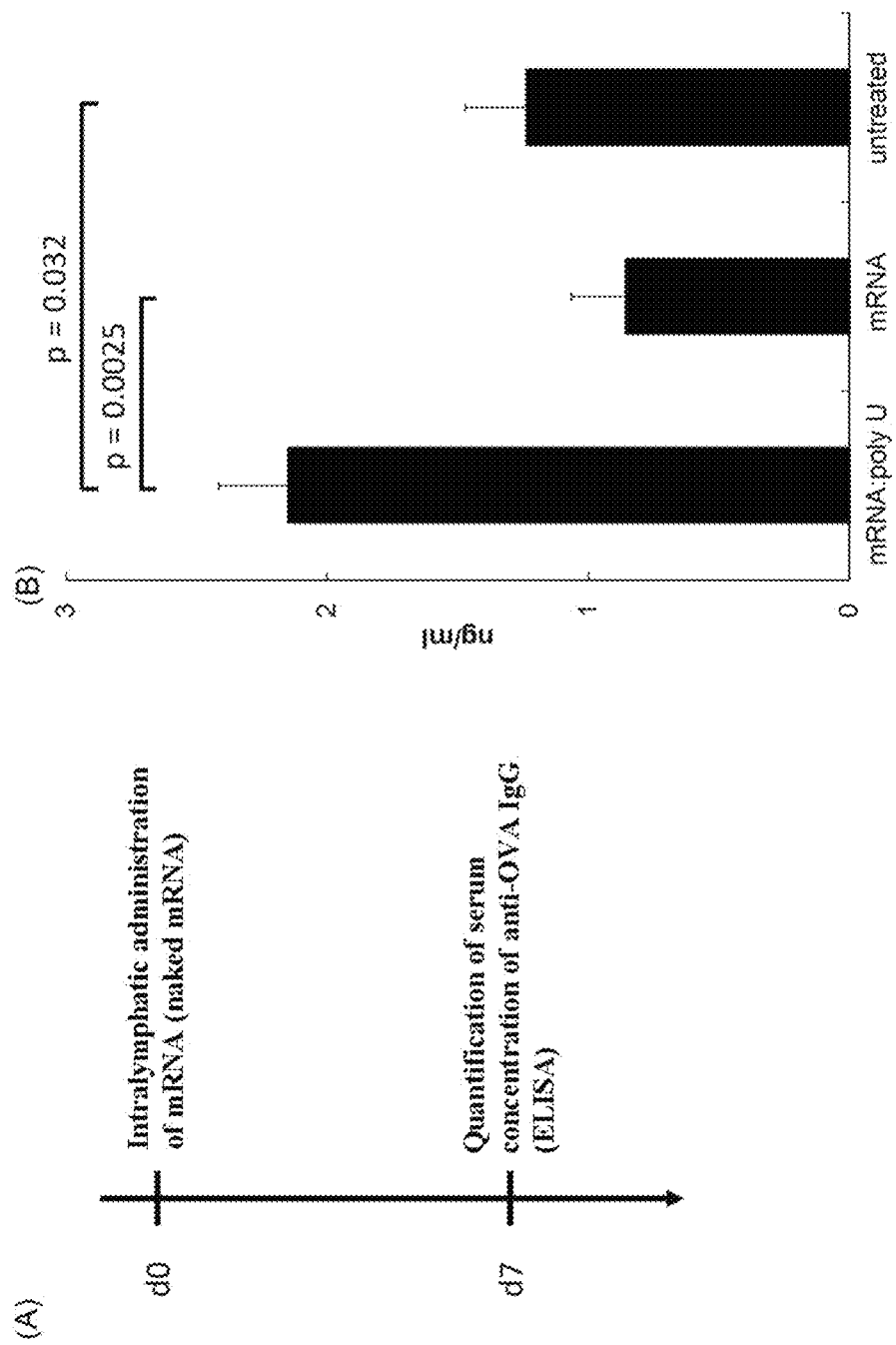
FIG. 26 is a view showing the results of administration of a double-stranded RNA to mice. (A) Procedures from administration to quantification of the serum concentration of anti-OVA IgG, and (B) the serum concentration of anti-OVA IgG.

Furthermore, the mRNA vaccine of the second aspect of the present invention was used to evaluate immune induction ability in mice, in terms of humoral immunity (FIG. 26(A)). As a result, it became clear that an mRNA having a poly A sequence hybridizing with a complementary strand RNA (poly U) significantly strongly induced antigen-specific humoral immunity, in comparison to a non-hybridizing mRNA (FIG. 26(B)).

Further, a mechanism whereby such an mRNA having a poly A sequence hybridizing with poly U provokes an inflammatory response was also examined. It has been known that RIG-I as an intracellular receptor plays an important role in recognition of a double-stranded RNA. Also, it has been reported that triphosphorylation of the 5'-terminus of either one RNA strand is important for the binding of RIG-I with a double-stranded RNA. It was found that, in the case of using an mRNA having a poly A sequence hybridizing with a complementary strand RNA (poly U) having a triphosphorylated 5'-terminus, a stronger inflammatory response is provoked than in the case of using an mRNA having a poly A sequence hybridizing with a complementary strand RNA (RNA ppp(-)) having a non-triphosphorylated 5'-terminus (FIG. 23(A)). Accordingly, it was suggested that RIG-I be strongly associated with an inflammatory response to the mRNA having a hybridized poly A sequence.

Herein, when poly U was allowed to hybridized with the mRNA, an inflammatory response was provoked, but when a complementary strand to a protein coding sequence was allowed to hybridized with the mRNA, such an inflammatory response was not provoked so much (FIG. 23(A)). It was strongly suggested that recognition of triphosphoric acid by RIG-I be different depending on the type of the used complementary strand. In the case of poly U, it is considered: that its 5'-terminus is exposed to the terminus of the mRNA, and thus, triphosphoric acid is likely to become three-dimensionally easily recognizable by RIG-I; and also that the sequence around triphosphoric acid contains many U, but since AU bonds are weak, the motility of triphosphoric acid is increased and thus is likely to become easily recognizable. Hence, it was strongly suggested that selection of the complementary strand be important for innate immune response via RIG-I.

It has been generally known that a double-stranded RNA introduced into cells provokes a strong inflammatory response. However, it was found that if a full-length complementary strand is allowed to bind to the mRNA, the expression of a protein from the mRNA is inhibited. In the second aspect of the present invention, a complementary strand is allowed to site-specifically hybridize with, mainly, a poly A sequence of the mRNA, so that an inflammatory response can be provoked, while maintaining the protein expression from the mRNA.

2.2. mRNA Vaccine

The second aspect of the present invention provides an mRNA vaccine, which comprises a double-stranded RNA consisting of an mRNA encoding an antigen and at least one RNA oligomer hybridizing with at least the poly A sequence of the mRNA, wherein the at least one RNA oligomer is chemically unmodified or is chemically modified.

2.2.1. mRNA

The term "mRNA" means a messenger RNA, and the mRNA generally comprises a 5' untranslated region (5' UTR), a coding region, and a 3' untranslated region (3' UTR). In general, the mRNA further comprises a cap structure at the 5'-terminus (5' Cap) and a poly A sequence at the 3'-terminus.

The mRNA used in the mRNA vaccine may be any one of the following mRNAs.

(1) mRNA comprising 5' Cap, 5' UTR, a coding region, 3' UTR, and poly A in this order.

(2) mRNA comprising 5' Cap, 5' UTR, coding region, and poly A in this order.

(3) mRNA comprising 5' UTR, a coding region, 3' UTR, and poly A in this order.

(4) mRNA comprising 5' UTR, a coding region, and poly A in this order.

The mRNA used in the mRNA vaccine can be produced by transcribing a template DNA encoding the target gene under in vitro environment according to a known method. For example, the mRNA encoding a target gene can be produced according to the method described in Blood 108 (13) (2006) 4009-17. Specifically, a template DNA, in which a poly A/T strand is incorporated downstream of a protein coding sequence, is cleaved immediately downstream of the poly A/T strand, and is then subjected to in vitro transcription in a buffer solution containing translation enzymes, nucleosides and 5' Cap analogs. Thereafter, the mRNA is purified, so as to produce an mRNA encoding a target gene. A more specific method of preparing an mRNA is as described in the after-mentioned Examples.

The antigen encoded by the coding region of the mRNA can be arbitrarily selected from known antigens preferably used in induction of an immune response. More specific examples of the antigen may include tumor antigens, virus-derived antigens, bacteria-derived antigens, fungus-derived antigens, protist-derived antigens, animal-derived antigens, plant-derived antigens, and autoantigens of autoimmune diseases. The antigen encoded by the mRNA may be a single antigen, or two or more (e.g., two, three, four, five or more) antigens of the same or different type. In some embodiments of the second aspect of the present invention, the antigen encoded by the mRNA is a single antigen.

The length of the poly A sequence of the mRNA is, for example, 10 to 500 nucleotides, preferably 30 to 300 nucleotides, and more preferably 60 to 250 nucleotides.

The 5' UTR and 3' UTR sequences of the mRNA may have a sequence identity of 100% to naturally occurring sequences. Otherwise, the 5' UTR and 3' UTR sequences of the mRNA may be partially or entirely substituted with other 5' UTR and/or 3' UTR sequences. Examples of such other 5' UTR and/or 3' UTR sequences may include the sequences of the 5' UTR and/or 3' UTR of an mRNA encoding globin, hydroxysteroid (17-β) dehydrogenase 4, or albumin.

In some aspects, the mRNA is not modified. In this case, since the mRNA itself is a natural product, it can be expected that the translation process is hardly impaired.

In some other aspects, in order to further stability the mRNA, the mRNA is modified. Examples of the modification of the mRNA may include chemical modification of the nucleotides of the mRNA, modification of the G/C content in the coding region of the mRNA, and modification of the Cap structure of the mRNA.

It has been known that the chemical modification of the nucleotides of the mRNA is, for example, the improvement of the enzyme resistance of the mRNA. Examples of the chemically modified nucleotides of the mRNA itself may include methylated nucleotides (e.g., 5-methylcytosine), sulfur modified nucleotides (e.g., 2-thiouridine), pseudouridine, Ni methyl pseudouridine, and 5-methoxy-uridine.

Modification of the G/C content in the coding region of the mRNA means that the mRNA is modified so that the content of G (guanine)/C (cytosine) is increased. Thereby, a more stable mRNA can be obtained.

Modification of the Cap structure of the mRNA means that the position 2 of the first or second ribose on the 5'-terminal side is set to be a methoxy group. It has been known that expression efficiency is thereby improved.

Preparation and modification of the mRNA can be carried out according to a known method or a method equivalent thereto.

2.2.2. RNA Oligomer

In the second aspect of the present invention, at least one RNA oligomer hybridizes with, at least, the poly A sequence of the mRNA. Moreover, said RNA oligomer is chemically unmodified.

The sequence of the mRNA, with which one RNA oligomer hybridizes, is any one of the following sequences, for example.

(1) A consecutive sequence in the poly A sequence of the mRNA.

(2) A consecutive sequence in the 3' UTR and poly A sequence of the mRNA.

(3) A consecutive sequence in the coding region and poly A sequence of the mRNA.

In the case of the consecutive sequence in the poly A sequence of the mRNA described in the above (1), the RNA oligomer is designed, such that one RNA oligomer hybridizes with the entire poly A sequence (100%) or a part thereof but it does not hybridize with the sequence immediately before it (i.e., 3' UTR or a coding region). Herein, a part of the poly A sequence means a sequence having a nucleotide length of greater than 0% and less than 100% of the full-length poly A sequence, for example, a nucleotide length of 10 or more nucleotides (preferably, a nucleotide length of 17 or more nucleotides). The poly A sequence portion of the mRNA preferably comprises a complementary sequence of 17 or more nucleotides, with which the RNA oligomer hybridizes.

In a case where the mRNA is designed to comprise a 3' UTR sequence immediately before the poly A sequence thereof, the sequence with which one RNA oligomer hybridizes may be a consecutive sequence in the 3' UTR and poly A sequence of the mRNA described in the above (2). In this case, the RNA oligomer is designed, such that one RNA oligomer hybridizes with a consecutive sequence in the entire poly A sequence (100%) or a part thereof, and in a part of the 3' UTR sequence immediately before it. In this case, one RNA oligomer is designed, such that it hybridizes, for example, with a sequence having a nucleotide length of greater than 0% and less than 100% of the full-length poly A sequence, for example, a nucleotide length of 10 or more nucleotides (i.e., a nucleotide length of 10, 11, 12, 13, 14, 15, 16, 17 or more nucleotides, preferably, a nucleotide length of 17 or more nucleotides) and a sequence having a nucleotide length of greater than 0% and less than 100% of the full-length 3' UTR sequence immediately before the poly A sequence. The poly A sequence portion and 3' UTR sequence portion of the mRNA preferably comprise a complementary sequence of a total of 17 or more nucleotides, with which the RNA oligomer hybridizes. The shorter the 3' UTR sequence portion of the mRNA, with which the RNA oligomer hybridizes, the more preferable it is. The length of the 3' UTR sequence portion is, for example, 1 to 30 nucleotides, preferably 1 to 25 nucleotides, and more preferably 1 to 2 nucleotides.

In a case where the mRNA is designed to comprise a coding sequence immediately before the poly A sequence thereof, the sequence with which one RNA oligomer hybridizes may be a consecutive sequence in the coding sequence and poly A sequence of the mRNA described in the above (3). In this case, the RNA oligomer is designed, such that one RNA oligomer hybridizes with a consecutive sequence in the entire poly A sequence (100%) or a part thereof, and in a part of the coding sequence immediately before it. In this case, one RNA oligomer is designed, such that it hybridizes, for example, with a sequence having a nucleotide length of greater than 0% and less than 100% of the full-length poly A sequence, for example, a nucleotide length of 10 or more nucleotides (i.e., a nucleotide length of 10, 11, 12, 13, 14, 15, 16, 17 or more nucleotides, preferably, a nucleotide length of 17 or more nucleotides) and a sequence having a nucleotide length of greater than 0% and less than 100% of the full-length coding sequence immediately before the poly A sequence. The poly A sequence portion and coding sequence portion of the mRNA preferably comprise a complementary sequence of a total of 17 or more nucleotides, with which the RNA oligomer hybridizes. The shorter the coding sequence portion of the mRNA, with which the RNA oligomer hybridizes, the more preferable it is. The length of the coding sequence portion is, for example, 1 to 30 nucleotides, preferably 1 to 25 nucleotides, and more preferably 1 to 2 nucleotides.

Specific examples of the RNA oligomer may include the following RNA oligomers:

(a) an RNA oligomer having a sequence complementary to any one of the above-described consecutive sequences (1) to (3), or (b) an RNA oligomer having an RNA sequence having an identity of 90% or more to a sequence complementary to any one of the above-described consecutive sequences (1) to (3), and hybridizing with the mRNA.

The range of "90% or more" in the "RNA sequence having an identity of 90% or more" is, for example, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more. In general, the numerical value of the above-described identity is preferable, as the numerical value increases. Besides, the identity of RNA sequences can be determined using analysis software such as BLAST (see, for example, Altzshul S. F. et al., J. Mol. Biol. 215, 403(1990)). In the case of using BLAST, the default parameters of each program are used.

The phrase "hybridize with the mRNA" means that the RNA oligomer hybridizes with the mRNA under the after-mentioned hybridization conditions.

The RNA oligomer may further comprise another sequence, or may not comprise another sequence. Examples of such "another sequence" may include a promoter sequence and a restriction enzyme sequence, which remain upon production of the RNA oligomer, and a sequence inevitably remaining upon the designing of the RNA oligomer, or a part thereof. When the RNA oligomer comprises "another sequence," the nucleotide length of "another sequence" is, for example, 1 to 30 nucleotides, preferably 1 to 25 nucleotides, and more preferably 1 to 2 nucleotides.

The RNA oligomer consists of preferably a sequence of at least 10 nucleotides, more preferably a sequence of at least 17 nucleotides, further preferably a sequence of at least 30 nucleotides, and particularly preferably a sequence of at least 60 nucleotides. In addition, in some aspects, the RNA oligomer consists of preferably a sequence of 10 to 500 nucleotides, more preferably a sequence of 17 nucleotides to 500 nucleotides, further preferably a sequence of 30 to 300 nucleotides, and particularly preferably a sequence of 60 to 250 nucleotides. The nucleotide length of the RNA oligomer can be designed, as appropriate, taking into consideration the length of the poly A sequence of the mRNA, etc.

The RNA oligomer in some aspects does not comprise chemical modification. In some other aspects, the RNA oligomer comprises chemical modification. The chemical modification may be, for example, modification with a hydrophobic group. Examples of the modification with a hydrophobic group may include cholesterol modification and tocopherol modification. Moreover, the chemical modification may also be, for example, polyethylene glycol modification.

It is to be noted that the definition of "chemical modification" does not include the triphosphoric acid structure at the 5'-terminus.

The RNA oligomer can be prepared according to a known method or a method equivalent thereto. The RNA oligomer is produced from a template DNA by in vitro transcription. In principle, the RNA oligomer can be prepared in almost the same manner as the aforementioned production of the mRNA. However, although a 5' Cap analog is added to the mRNA upon the transcription thereof, such Cap analog is not added upon the production of the RNA oligomer. Thus, when the RNA oligomer is biologically prepared, it can have a triphosphoric acid structure at the 5'-terminus thereof. The method of removing triphosphoric acid is as described later.

2.2.3. Double-Stranded RNA

Double-stranded RNA is formed by allowing the aforementioned mRNA to hybridize with at least one of the aforementioned RNA oligomers.

The double-stranded RNA can be prepared by hybridization of the mRNA with the RNA oligomer. More specifically, the hybridization can be carried out under the conditions described in the after-mentioned Examples, or conditions equivalent thereto. The number of the RNA oligomers hybridizing with a single mRNA is at least one, preferably 1 to 5, more preferably 1 to 3, further preferably 1 or 2, and particularly preferably 1.

Hybridization of the RNA oligomer(s) with the mRNA can be carried out by applying a known method and known conditions. More specifically, in the hybridization, the reaction mixture is heated and is then left at rest for a certain period of time, and thereafter, the temperature is gradually decreased. The heating is carried out for the purpose of dissociating complementary bonds previously existing in the molecules of the mRNA or the oligomer(s), or among the molecules thereof, and thereby more efficiently binding the mRNA with the oligomer(s). The temperature and the time can be adjusted, as appropriate, as long as suitable hybridization can be guaranteed. In particular, since poly A or poly U is unlikely to bind to another sequence in advance, more moderate heating conditions can be determined. Moreover, moderate temperature decrease brings on an increase in the hybridization specificity. In addition, the chain length of the oligomer does not largely influence on determination of hybridization conditions. Hybridization conditions should be determined, as appropriate, while evaluating hybridization efficiency. For example, the methods and conditions described in the Examples later are applied.

In some aspects, the double-stranded RNA has a triphosphoric acid structure at the 5'-terminus of the RNA oligomer. Since the double-stranded RNA has such a triphosphoric acid structure at the 5'-terminus of the RNA oligomer, it can provoke a stronger inflammatory response.

In some other aspects, the double-stranded RNA does not have a triphosphoric acid structure at the 5'-terminus of the RNA oligomer. Triphosphorylation can be eliminated according to a known method or a method equivalent thereto. The method of eliminating triphosphorylation may be, for example, a method of using Antarctic phosphatase (New England Biolabs, cat. no. M0289S), as in the aftermentioned Examples.

In some aspects, the double-stranded RNA is in a naked form. That is, the double-stranded RNA is not loaded into carriers.

In some other aspects, the double-stranded RNA is in a form in which it is loaded in a carrier. The type of such a carrier is not particularly limited, as long as it can load the double-stranded mRNA therein and can deliver it to a preferred site in the body of a subject. The carrier is a lipidic mRNA carrier or a cationic polymer complex, and more preferably a polymeric micelle or a lipidic mRNA carrier.

The polymeric micelle has a two-layer structure consisting of an inner core formed with a condensed nucleic acid and a cationic polymer, and an outer shell formed with a hydrophilic polymer. The cationic polymer is, for example, a polyamino acid derivative. The hydrophilic polymer is, for example, polyethylene glycol ("PEG"). The inner core physically or chemically encapsulates the mRNA therein. The outer shell delivers the mRNA encapsulated in the inner core to predetermined tissues by its physicochemical properties. The polymeric micelle can enter the cells by endocytosis. The polymeric micelle can utilize, for example, the interaction of a polycation with a nucleic acid on a block polymer (polyion complex ("PIC")), and can also utilize a hybrid micelle of the polyion complex with an inorganic molecule. Examples of the PIC-type polymeric micelle may include PIC micelles formed by association of mRNA with PEG-PAsp (DET)-Chol, PEG-PAsp (DET), or PEG-PLys (see the Examples as described later), or other polycations such as PAsp(TET) or PAsp(TEP) used in block copolymers (Uchida, S., et al., Biomaterials (2016) 82, pp. 221-228), and those used in triblock copolymers (Osawa, S., et al., Biomacromolecules 17, pp. 354-361 (2016)). Examples of the hybrid micelle with an inorganic molecule may include PEGylated calcium phosphate (CaP) particles (Pittela, et al., Biomaterials (2011) 32, pp. 3106-3114) and PEGylated silica particles (Miyata, K., et al. Biomaterials (2010) 31, pp. 4764-4770).

The lipidic mRNA carrier is formed using a lipid or a cationic lipid as a carrier, and an mRNA is loaded in or bound to the carrier. The lipidic mRNA carrier is obtained by mixing an mRNA with one or more selected from the group consisting of: for example, cationic lipids such as N-[1-(2, 3-dioleyloxy) propyl]-N,N,N-trimethylammonium chloride (DOTMA), 2,3-dioleyloxy-N-[2-(spermine carboxamido) ethyl]-N, N-dimethyl-1-propanaminium trifluoroacetic acid (DOSPA), 1,2-dioleoyl-3-(trimethylammonium)propane (DOTAP), N-[1-(2,3-dimyristyloxy)propyl]-N,N-dimethyl-N-(2-hydroxyethyl) ammonium bromide (DMRIE), or DC-Cholesterol; neutral phospholipids such as distearoylphosphatidylcholine (DSPC) or dioleoyl phosphatidylethanolamine (DOPE); PEGylated lipids; and cholesterols.

The cationic polymer complex is a mixture of an mRNA and, for example, linear or branched polyethylenimine, polylysine, polyarginine, a chitosan derivative, or a polymethacrylic acid derivative.

These carriers can be prepared by a known method or a method equivalent thereto.

2.2.4. Adjuvant

In some preferred aspects, the RNA vaccine is not used together with an adjuvant.

In some other aspects, the RNA vaccine is used together with an adjuvant. When the RNA vaccine is used together with an adjuvant, it may be formulated together with the adjuvant. The adjuvant is any given compound that is preferable for enhancing an immune response. Such an adjuvant is known, and a person skilled in the art can select a suitable adjuvant from any given adjuvants.

2.3. Prevention or Treatment of Disease

The mRNA vaccine can be used to prevent or treat a disease in a subject in need of the prevention or treatment of the disease.

Examples of the disease to be prevented or treated may include cancers, viral infections, bacterial infections, fungal infections, protozoal infections, and autoimmune diseases. These diseases can be prevented or treated by appropriately selecting the antigen encoded by the coding region of the aforementioned mRNA, depending on the disease to be prevented or treated.

The "subject" is a human, or an organism other than the human, such as, for example, birds and non-human mammals (e.g., bovines, monkeys, cats, mice, rats, Guinea pigs, hamsters, pigs, dogs, rabbits, sheep and horses).

The mRNA vaccine can be formulated according to an ordinary method. In some aspects, the mRNA vaccine comprises a pharmaceutically acceptable additive. Examples of the pharmaceutically acceptable additive may include water, a pharmaceutically acceptable organic solvent, collagen, polyvinyl alcohol, polyvinyl pyrrolidone, a carboxyvinyl polymer, sodium carboxymethyl cellulose, sodium polyacrylate, sodium alginate, water-soluble dextran, sodium carboxymethyl starch, pectin, methyl cellulose, ethyl cellulose, xanthan gum, gum Arabic, casein, agar, polyethylene glycol, diglycerin, glycerin, propylene glycol, Vaseline, paraffin, stearyl alcohol, stearic acid, human serum albumin, mannitol, sorbitol, lactose, and a pharmaceutically acceptable surfactant.

The additives are selected from the above-described additives depending on the dosage form of the mRNA vaccine, and are used alone or by appropriately being combined with one another. For example, when the mRNA vaccine is used as an injection preparation, the purified double-stranded RNA is dissolved in a solvent (e.g. a normal saline, a buffer, a dextrose solution, etc.), and Tween 80, Tween20, gelatin, human serum albumin, etc. are then added to the solution, and the obtained solution can be used as an injection preparation. Alternatively, in order to prepare a dosage form that is dissolved before use, the mRNA vaccine may be freeze-dried. Examples of an excipient for freeze-drying may include: sugars, such as mannitol, dextrose, lactose, sucrose, mannitol, or sorbitol; starches derived from corn, wheat, rice, potato, or other plants; celluloses, such as methyl cellulose, hydroxypropylmethyl cellulose, or carboxymethyl cellulose sodium; rubbers, such as gum Arabic or gum tragacanth; gelatin; and collagen.

The applied dose of the mRNA vaccine can be selected, as appropriate, depending on the age, sex and symptoms of a subject, administration route, the number of administrations, dosage form, etc. The effective dose of the mRNA vaccine means the amount of the vaccine that reduces the symptoms or conditions of the disease. The therapeutic effects and toxicity of such an mRNA vaccine can be determined by standard pharmaceutical procedures applied to cell cultures or experimental animals, for example, based on ED50 (the dose that is therapeutically effective for 50% of a population) and LD50 (the dose that is lethal to 50% of a population). In some aspects, the dose of the mRNA vaccine can be set at an mRNA dose range of 10 ng to 1 g, 100 ng to 100 mg, 1 µg to 10 µg, or 30 µg to 300 µg per adult per day.

The administration route of the mRNA vaccine can be selected, as appropriate. Examples of the administration route may include transdermal, intranasal, transbronchial, intramuscular, intraperitoneal, intravenous, subcutaneous, intrarectal, and intravaginal administrations, but are not limited thereto.

The number of administrations of the mRNA vaccine can be set at once or several times, as long as side effects are within a clinically acceptable range.

In some aspects, an antibody titer or cellular immunity activity in the administration of the mRNA vaccine is measured. For example, then antibody titer can be evaluated by collecting blood from a living body and then quantifying IgG in the serum. The cellular immunity activity can be evaluated by separating lymphocytes from a living body, then culturing them, and then measuring incorporation of $^3$H-thymidine.

2.4. Kit

The kit of the second aspect of the present invention is characterized in that it includes the above-described mRNA vaccine. The present kit can be preferably used, for example, in a method for treating various types of diseases using the above-described mRNA vaccine.

In the kit, the storage state of the above-described mRNA vaccine is not limited. Taking into consideration stability (storability), the ease of use, etc., the state of a solution, powder or the like can be selected.

The kit may include other components, as well as the above-described mRNA vaccine. Examples of such other components may include various types of buffers and an instruction manual (use manual). The kit may include or may not include an adjuvant. Preferably, the kit does not include an adjuvant.

3. Third Aspect of the Present Invention

3.1. Summary of Third Aspect of the Present Invention

Figure 37:
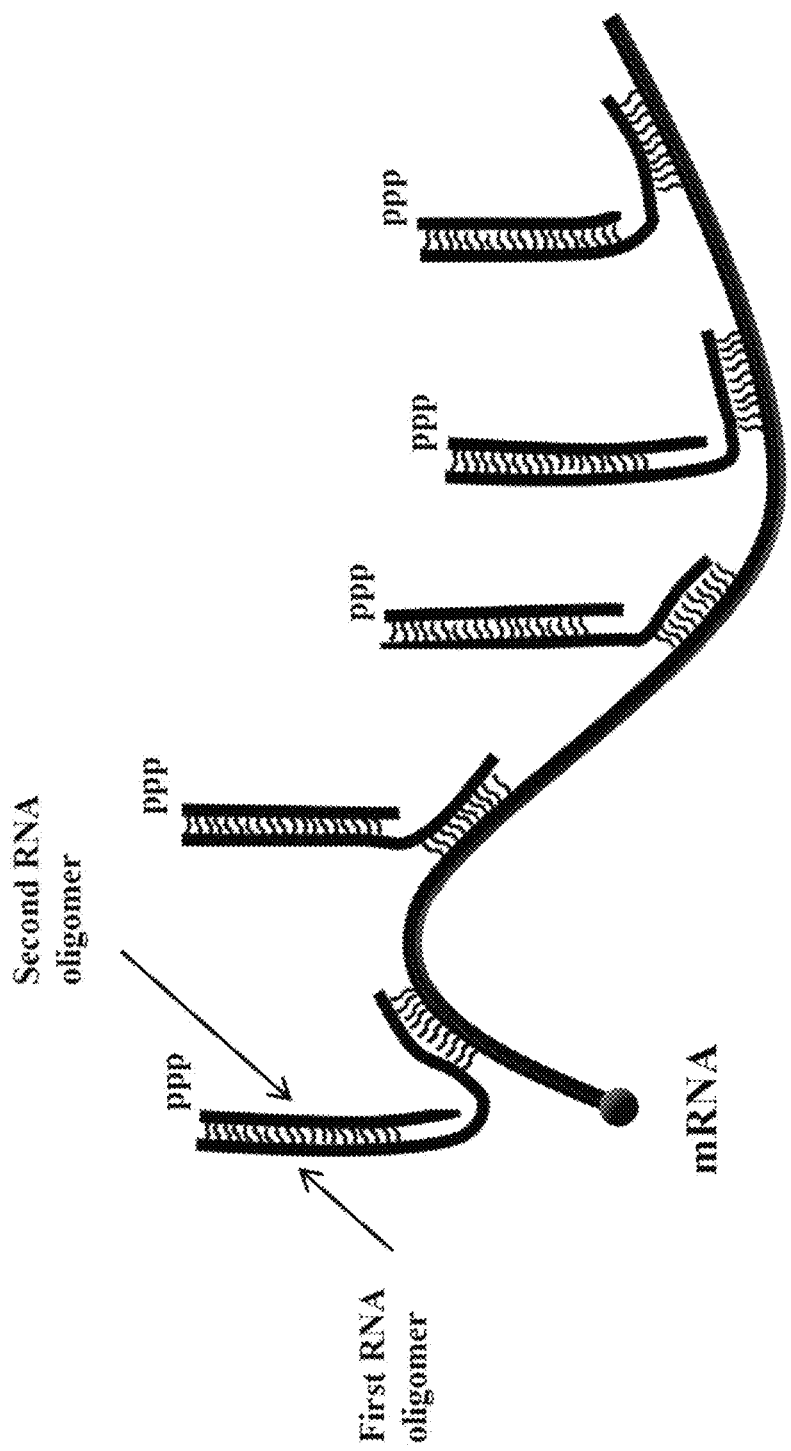
FIG. 37 is a view showing a double-stranded RNA.
Figure 38:
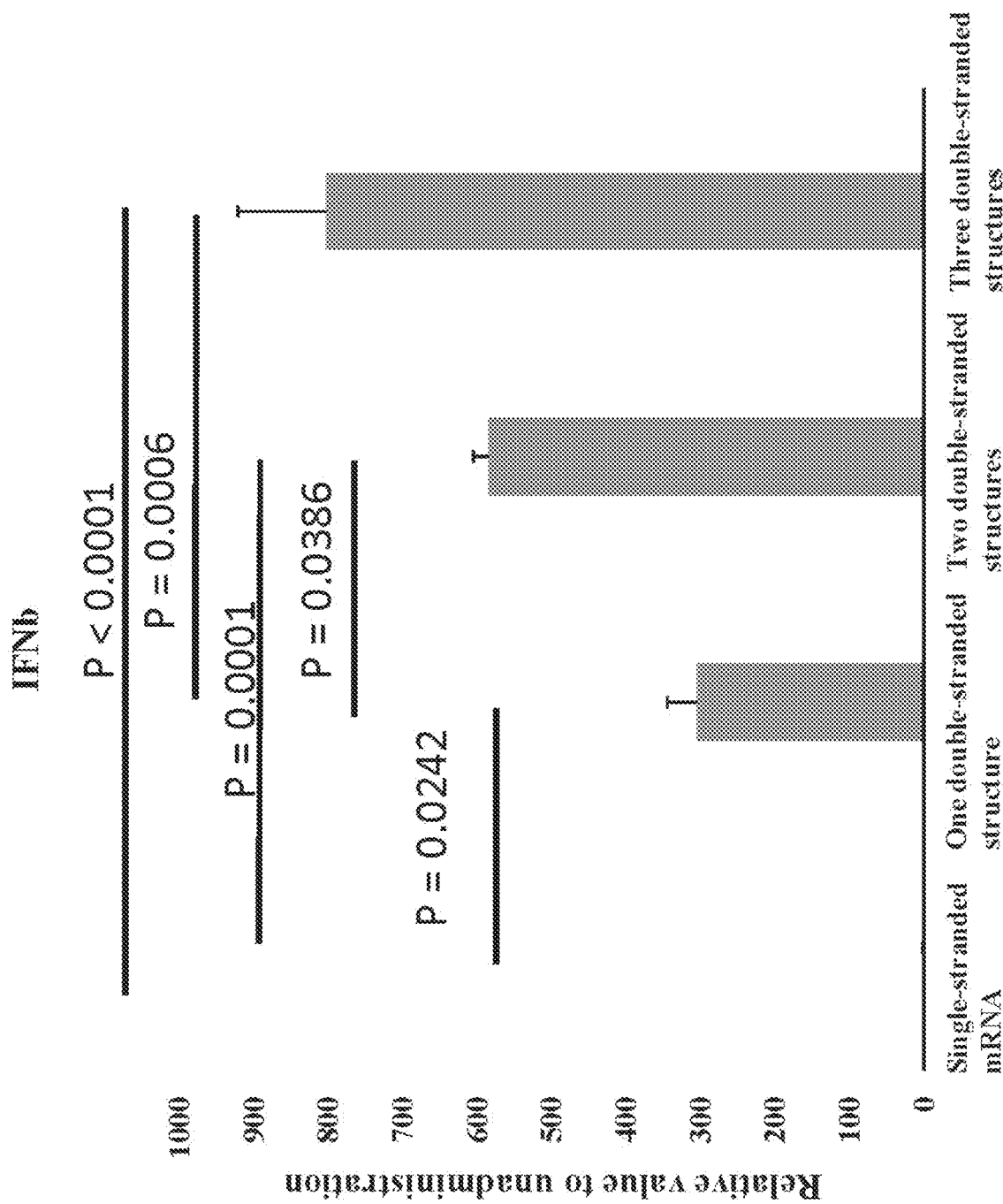
FIG. 38 is a view showing the results of introduction of a double-stranded RNA into a dendritic cell line (DC2.4). The figure shows the relative expression level of interferon β to untreated control.
Figure 39:
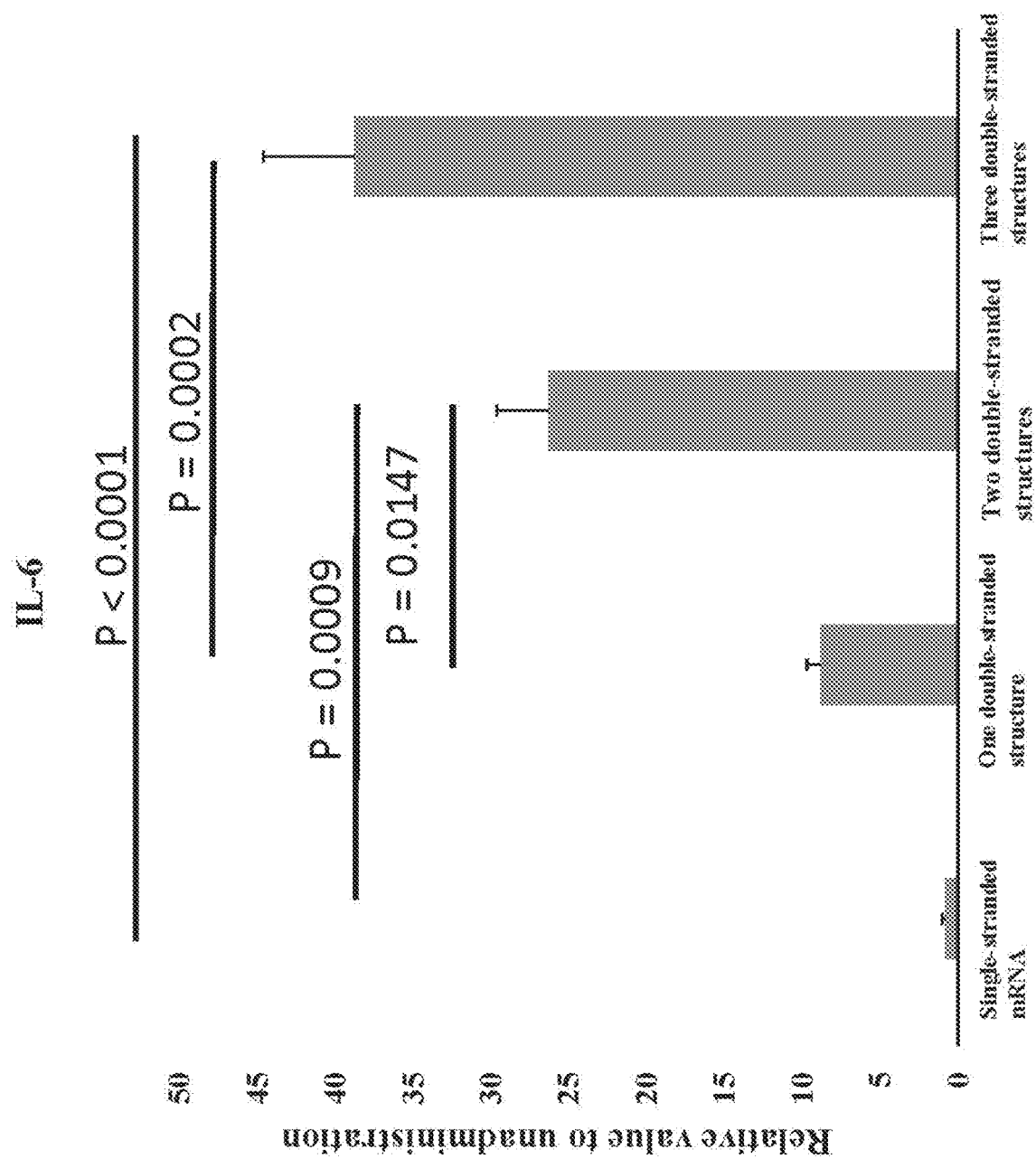
FIG. 39 is a view showing the results of introduction of a double-stranded RNA into a dendritic cell line (DC2.4). The figure shows the relative expression level of interleukin 6 to untreated control.
Figure 40:
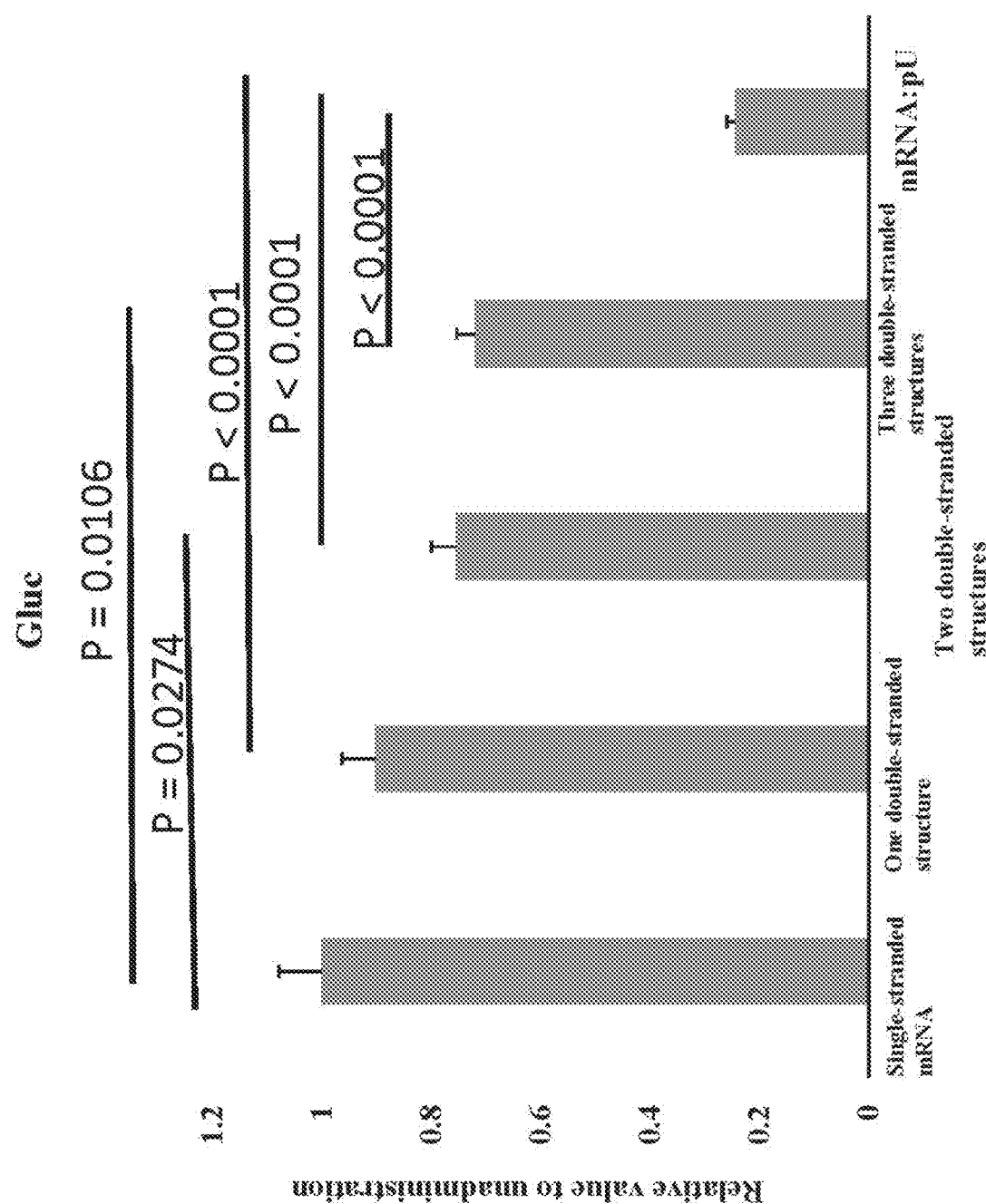
FIG. 40 is a view showing the results of introduction of a double-stranded RNA into a dendritic cell line (DC2.4). The figure shows the relative expression level of Luc to a single-stranded RNA.

It has been known that RIG-I as an intracellular receptor plays an important role in recognition of a double-stranded RNA. Also, it has been reported that triphosphorylation of the 5'-terminus of either one RNA strand is important for the binding of RIG-I with a double-stranded RNA. A second RNA oligomer having a triphosphorylated 5'-terminus was allowed to hybridize with a first RNA oligomer, and the resultant was then allowed to hybridize with the mRNA to produce a double-stranded mRNA. The double-stranded mRNA of FIG. 37 shows a double-stranded mRNA, in which 5 RNA oligomers are allowed to hybridize with a single mRNA. On the other hand, in the after-mentioned Examples, a double-stranded mRNA, in which 1 to 3 RNA oligomers were allowed to hybridize with a single mRNA, was used. In the case of using these double-stranded mRNAs, immunostimulation action was improved in comparison to a non-hybridizing mRNA (FIGS. 38 and 39), and further, the efficiency of mRNA expression was maintained (FIG. 40). At this time, the immunostimulation action was improved, as the number of double-stranded RNA oligomers hybridizing with the mRNA increased (FIGS. 38 and 39). Accordingly, it was suggested that RIG-I be strongly associated with an inflammatory response to the mRNA hybridizing with the RNA oligomer(s).

The specific mRNA vaccine of the second aspect of the present invention exhibited slightly decreased protein expression efficiency ("mRNA:pU" in FIG. 40), but in the case of using the above-described double-stranded mRNA, translation activity was sufficiently maintained ("One double-stranded structure," "Two double-stranded structures," and "Three double-stranded structures" in FIG. 40). Moreover, by adjusting the number of hybridizing RNA oligomers, the degree of immune response could be adjusted ("One double-stranded structure," "Two double-stranded structures," and "Three double-stranded structures" in in FIGS. 38 and 39). Excessive inflammation causes side effects and also, it is likely to be unfavorable for obtaining vaccine effects. The point that the intensity of immune response could be adjusted by changing the number of the RNA oligomers in the present study is extremely important to obtain an inflammatory response having a suitable intensity for obtaining vaccine effects.

Furthermore, in the case of the mRNA vaccine according to the third aspect of the present invention, it is easy to construct a blunt 5'-terminal triphosphorylated structure necessary for the recognition by RIG-I, in comparison to the mRNA vaccine of the second aspect.

Further, in the case of the mRNA vaccine according to the third aspect of the present invention, upon preparation of the second RNA strand by in vitro transcription, a complementary strand RNA of an RNA of interest is transcribed as a by-product. However, in comparison to the specific mRNA vaccine of the second aspect, generation of such a by-product can be easily avoided.

3.2. mRNA Vaccine

The third aspect of the present invention provides an mRNA vaccine, which comprises a double-stranded RNA consisting of an mRNA encoding an antigen, at least one first RNA oligomer hybridizing with the mRNA, and a second RNA oligomer hybridizing with the first RNA oligomer, wherein the first RNA oligomer comprises:

(a) an RNA sequence comprising a first RNA sequence consisting of a sequence of 12 to 40 nucleotides complementary to the sequence of the mRNA, and a second RNA sequence consisting of a sequence of 10 to 200 nucleotides complementary to the sequence of the second RNA oligomer, in this order from the 5'-terminus thereof, (b) an RNA sequence comprising a first RNA sequence having an identity of 90% or more to a sequence of 12 to 40 nucleotides complementary to the sequence of the mRNA and hybridizing with the mRNA, and a second RNA sequence having an identity of 90% or more to a sequence of 10 to 200 nucleotides complementary to the sequence of the second RNA oligomer and hybridizing with the second RNA oligomer, in this order from the 5'-terminus thereof, (c) an RNA sequence comprising a second RNA sequence consisting of a sequence of 10 to 200 nucleotides complementary to the second RNA oligomer, and a first RNA sequence consisting of a sequence of 12 to 40 nucleotides complementary to the sequence of the mRNA, in this order from the 5'-terminus thereof, or (d) an RNA sequence comprising a second RNA sequence having an identity of 90% or more to a sequence of 10 to 200 nucleotides complementary to the sequence of the second RNA oligomer and hybridizing with the second RNA oligomer, and a first RNA sequence having an identity of 90% or more to a sequence of 12 to 40 nucleotides complementary to the sequence of the mRNA and hybridizing with the mRNA, in this order from the 5'-terminus thereof.

3.2.1. mRNA

The term "mRNA" means a messenger RNA, and the mRNA generally comprises a 5' untranslated region (5' UTR), a coding region, and a 3' untranslated region (3' UTR). In general, the mRNA further comprises a cap structure at the 5'-terminus (5' Cap) and a poly A sequence at the 3'-terminus.

The mRNA used in the mRNA vaccine may be any one of the following mRNAs.

(1) mRNA comprising 5' Cap, 5' UTR, a coding region, 3' UTR, and poly A in this order.

(2) mRNA comprising 5' Cap, 5' UTR, coding region, and poly A in this order.

(3) mRNA comprising 5' UTR, a coding region, 3' UTR, and poly A in this order.

(4) mRNA comprising 5' UTR, a coding region, and poly A in this order.

The mRNA used in the mRNA vaccine can be produced by transcribing a template DNA encoding the target gene under in vitro environment according to a known method. For example, the mRNA encoding a target gene can be produced according to the method described in Blood 108 (13) (2006) 4009-17. Specifically, a template DNA, in which a poly A/T strand is incorporated downstream of a protein coding sequence, is cleaved immediately downstream of the poly A/T strand, and is then subjected to in vitro transcription in a buffer solution containing translation enzymes, nucleosides and 5' Cap analogs. Thereafter, the mRNA is purified, so as to produce an mRNA encoding a target gene. A more specific method of preparing an mRNA is as described in the after-mentioned Examples.

The antigen encoded by the coding region of the mRNA can be arbitrarily selected from known antigens preferably used in induction of an immune response. More specific examples of the antigen may include tumor antigens, virus-derived antigens, bacteria-derived antigens, fungus-derived antigens, protist-derived antigens, animal-derived antigens, plant-derived antigens, and autoantigens of autoimmune diseases. The antigen encoded by the mRNA may be a single antigen, or two or more (e.g., two, three, four, five or more) antigens of the same or different type. In some embodiments of the third aspect of the present invention, the antigen encoded by the mRNA is a single antigen.

The length of the poly A sequence of the mRNA is, for example, 10 to 500 nucleotides, preferably 30 to 300 nucleotides, and more preferably 60 to 250 nucleotides.

The 5' UTR and 3' UTR sequences of the mRNA may have a sequence identity of 100% to naturally occurring sequences. Otherwise, the 5' UTR and 3' UTR sequences of the mRNA may be partially or entirely substituted with other 5' UTR and/or 3' UTR sequences. Examples of such other 5' UTR and/or 3' UTR sequences may include the sequences of the 5' UTR and/or 3' UTR of an mRNA encoding globin, hydroxysteroid (17-β) dehydrogenase 4, or albumin.

In some aspects, the mRNA is not modified. In this case, since the mRNA itself is a natural product, it can be expected that the translation process is hardly impaired.

In some other aspects, in order to further stability the mRNA, the mRNA is modified. Examples of the modification of the mRNA may include chemical modification of the nucleotides of the mRNA, modification of the G/C content in the coding region of the mRNA, and modification of the Cap structure of the mRNA.

It has been known that the chemical modification of the nucleotides of the mRNA is, for example, the improvement of the enzyme resistance of the mRNA. Examples of the chemically modified nucleotides of the mRNA itself may include methylated nucleotides (e.g., 5-methylcytosine), sulfur modified nucleotides (e.g., 2-thiouridine), pseudouridine, Ni methyl pseudouridine, and 5-methoxy-uridine.

Modification of the G/C content in the coding region of the mRNA means that the mRNA is modified so that the content of G (guanine)/C (cytosine) is increased. Thereby, a more stable mRNA can be obtained.

Modification of the Cap structure of the mRNA means that the position 2 of the first or second ribose on the 5'-terminal side is set to be a methoxy group. It has been known that expression efficiency is thereby improved.

Preparation and modification of the mRNA can be carried out according to a known method or a method equivalent thereto.

3.2.2. RNA Oligomer

In the third aspect of the present invention, at least one first RNA oligomer hybridizes with the mRNA. In addition, the second RNA oligomer further hybridizes with the first RNA oligomer.

The first RNA oligomer is an RNA strand comprising:

(a) an RNA sequence comprising a first RNA sequence consisting of a sequence of 12 to 40 nucleotides complementary to the sequence of the mRNA, and a second RNA sequence consisting of a sequence of 10 to 200 nucleotides complementary to the sequence of the second RNA oligomer, in this order from the 5'-terminus thereof, (b) an RNA sequence comprising a first RNA sequence having an identity of 90% or more to a sequence of 12 to 40 nucleotides complementary to the sequence of the mRNA and hybridizing with the mRNA, and a second RNA sequence having an identity of 90% or more to a sequence of 10 to 200 nucleotides complementary to the sequence of the second RNA oligomer and hybridizing with the second RNA oligomer, in this order from the 5'-terminus thereof, (c) an RNA sequence comprising a second RNA sequence consisting of a sequence of 10 to 200 nucleotides complementary to the second RNA oligomer, and a first RNA sequence consisting of a sequence of 12 to 40 nucleotides complementary to the sequence of the mRNA, in this order from the 5'-terminus thereof, or (d) an RNA sequence comprising a second RNA sequence having an identity of 90% or more to a sequence of 10 to 200 nucleotides complementary to the sequence of the second RNA oligomer and hybridizing with the second RNA oligomer, and a first RNA sequence having an identity of 90% or more to a sequence of 12 to 40 nucleotides complementary to the sequence of the mRNA and hybridizing with the mRNA, in this order from the 5'-terminus thereof.

The range of "90% or more" in the "RNA sequence having an identity of 90% or more" is, for example, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more. In general, the numerical value of the above-described identity is preferable, as the numerical value increases. Besides, the identity of RNA sequences can be determined using analysis software such as BLAST (see, for example, Altzshul S. F. et al., J. Mol. Biol. 215, 403(1990)). In the case of using BLAST, the default parameters of each program are used.

The phrase "hybridize with the mRNA" means that the RNA oligomer hybridizes with the mRNA under the after-mentioned hybridization conditions. The phrase "hybridize with the first RNA" means that the second RNA oligomer hybridizes with the first RNA under the after-mentioned hybridization conditions.

The first RNA sequence of the first RNA oligomer is designed to hybridize with the sequence of the mRNA consisting of consecutive 12 to 40 nucleotides. In some aspects, the first RNA sequence of the first RNA oligomer consists of a sequence of 12 to 30 nucleotides that is complementary to the sequence of the mRNA. More preferably, the first RNA sequence of the first RNA oligomer consists of a sequence of 15 to 23 nucleotides that is complementary to the sequence of the mRNA. Further preferably, the first RNA sequence of the first RNA oligomer consists of a sequence of 17 nucleotides that is complementary to the sequence of the mRNA.

The position in the mRNA, with which the RNA oligomer is allowed to hybridize, is any position of 5' UTR, a coding region, 3' UTR, and a poly A sequence. The RNA oligomer is desirably designed, such that it predicts the secondary structure of the mRNA, and hybridizes with a portion of the mRNA strand that does not have the secondary structure. That is to say, the RNA oligomer is preferably designed to hybridize with a portion not having the secondary structure in the entire mRNA sequence. The software that predicts the secondary structure of the mRNA is, for example, the one described in the Examples later. In some aspects, the RNA oligomer is designed to hybridize with at least one sequence of the 5' UTR, coding region, and 3' UTR of the mRNA.

The second RNA sequence of the first RNA oligomer is designed, such that it hybridizes with the sequence of the second RNA oligomer consisting of consecutive 10 to 200 nucleotides, in addition to the first RNA sequence having the above-described nucleotide length. In some aspects, the second RNA sequence of the first RNA oligomer consists of a sequence of 15 to 150 nucleotides that is complementary to the sequence of the second RNA oligomer, in addition to the first RNA sequence having the above-described nucleotide length. More preferably, the second RNA sequence of the first RNA oligomer consists of a sequence of 20 to 100 nucleotides that is complementary to the sequence of the second RNA oligomer, in addition to the first RNA sequence having the above-described nucleotide length. Further preferably, the second RNA sequence of the first RNA oligomer consists of a sequence of 20 to 80 nucleotides that is complementary to the sequence of the second RNA oligomer, in addition to the first RNA sequence having the above-described nucleotide length.

The second RNA sequence of the first RNA oligomer is designed, for example, as follows. That is to say, the second RNA sequence of the first RNA oligomer is designed to satisfy at least one of, and more preferably, 2, 3 or 4 of the following (i) to (iv). In some preferred aspects, the second RNA sequence of the first RNA oligomer is designed, at least, to satisfy the following (i) and (ii), and more preferably, at least one of the following (iii) and (iv), in addition to the following (i) and (ii):

(i) when a template DNA is transcribed under in vitro environment to prepare a second RNA oligomer comprising a triphosphorylated 5'-terminus, a complementary strand RNA (by-product) is not formed to the target RNA oligomer, (ii) the terminus of the double-stranded RNA on the side at which the second RNA oligomer hybridizes with the first RNA oligomer has a 5'-terminal triphosphorylated structure, preferably a blunt 5'-terminal triphosphorylated structure, (iii) the second RNA sequence and the second RNA oligomer do not hybridize with the sequence on the mRNA, and (iv) the first and second RNA oligomers do not form a secondary structure.

Herein, in order to realize "(i) when a template DNA is transcribed under in vitro environment to prepare a second RNA oligomer comprising a triphosphorylated 5'-terminus, a complementary strand RNA (by-product) is not formed to the target RNA oligomer," for example, the second RNA sequence of the first RNA oligomer is designed as follows. That is, the second RNA oligomer is prepared by removing nucleotides necessary for the transcription of the complementary strand RNA. Thus, the template DNA is designed, so that the target second RNA oligomer can be transcribed even though the aforementioned nucleotides are removed. For example, when the sequence GUGUGUGUGU (SEQ ID NO: 67) is subjected to in vitro transcription, the sequence ACACACACAC (SEQ ID NO: 68) may be generated as a by-product. When A is removed and the sequence is then subjected to in vitro transcription, generation of this by-product is avoided. Thus, the second RNA sequence of the first RNA oligomer is designed, so that such a second RNA oligomer can be prepared.

In addition, in order to realize "(ii) the terminus of the double-stranded RNA on the side at which the second RNA oligomer hybridizes with the first RNA oligomer has a 5'-terminal triphosphorylated structure, preferably a blunt 5'-terminal triphosphorylated structure," the second RNA sequence of the first RNA oligomer is designed as follows. That is, when the first RNA oligomer is the RNA sequence (a) or the RNA sequence (b), a second oligomer is prepared by subjecting a second RNA oligomer having a triphosphorylated structure at the 5'-terminus thereof to in vitro transcription. Preferably, at this time, the first oligomer is prepared, such that a blunt end can be obtained by hybridization of the 5'-terminus of the second oligomer with the 3'-terminus of the first oligomer. As such, the second RNA sequence of the first RNA oligomer is designed, so that such first and second RNA oligomers can be prepared.

On the other hand, when the first RNA oligomer is the RNA sequence (c) or the RNA sequence (d), a first oligomer is prepared by subjecting it to in vitro transcription. Preferably, at this time, the second oligomer is prepared, such that a blunt end can be obtained by hybridization of the 5'-terminus of the first RNA oligomer with the 3'-terminus of the second RNA oligomer. As such, the second RNA sequence of the first RNA oligomer is designed, so that such first and second RNA oligomers can be prepared.

In order to realize "(iii) the second RNA sequence and the second RNA oligomer do not hybridize with the sequence on the mRNA," after completion of the designing, the secondary structure is verified using software capable of predicting the secondary structures of a plurality of RNA strands (NUPACK, http://www.nupack.org), etc.

In order to realize "(iv) the first and second RNA oligomers do not form a secondary structure," after completion of the designing, the secondary structure is verified using software capable of predicting the secondary structures of a plurality of RNA strands (NUPACK, http://www.nupack.org), etc.

A linker sequence may be or may not be comprised between the first RNA sequence and the second RNA sequence of the first RNA oligomer. In some aspects, such a linker sequence is comprised between the first and second RNA sequences. The nucleotide length of the linker sequence is preferably 1 to 100 nucleotides, more preferably 2 to 30 nucleotides, and further preferably 2 to 20 nucleotides, in addition to the first RNA sequence and the second RNA sequence each having the above-described nucleotide length. The linker sequence is specifically designed, such that it does not hybridize with or hardly hybridizes with the mRNA or other sites of the RNA oligomers. In some aspects, in order that the linker sequence hardly hybridizes with the mRNA, the linker is designed using adenine (A) or uracil (U). This time, since a linker prepared using U is likely to bind to poly A if it has a certain length or more, in principle, A is preferably used. For example, the linker sequence is an oligo-adenine sequence having the above-described nucleotide length. However, when the position of the mRNA corresponding to the concerned position of the linker sequence is uracil (U), if the nucleotide at the position of the mRNA is adenine (A), the linker sequence hybridizes with the mRNA. In this case, the nucleotide at the position is preferably changed to uracil (U).

The first RNA oligomer may further comprise another sequence, or may not comprise another sequence. In some aspects, the first RNA oligomer may comprise another sequence. Examples of such "another sequence" may include a promoter sequence and a restriction enzyme sequence, which remain upon production of the RNA oligomer, and a sequence inevitably remaining upon the designing of the RNA oligomer, or a part thereof. When the RNA oligomer comprises "another sequence," the nucleotide length of "another sequence" is, for example, 1 to 30 nucleotides, preferably 1 to 25 nucleotides, and more preferably 1 to 2 nucleotides.

The second RNA oligomer comprises, for example, a sequence of 10 to 200 nucleotides, preferably a sequence of 15 to 150 nucleotides, more preferably a sequence of 20 to 100 nucleotides, and further preferably a sequence of 24 nucleotides hybridizes with the second RNA sequence of the first RNA oligomer. The method of designing the second RNA oligomer is as described in the above section regarding the second RNA sequence of the first RNA oligomer.

The second RNA oligomer may further comprise another sequence, or may not comprise another sequence. Examples of such "another sequence" may include a promoter sequence and a restriction enzyme sequence, which remain upon production of the RNA oligomer, and a sequence inevitably remaining upon the designing of the RNA oligomer, or a part thereof. When the RNA oligomer comprises "another sequence," the nucleotide length of "another sequence" is, for example, 1 to 30 nucleotides, preferably 1 to 25 nucleotides, and more preferably 1 to 2 nucleotides.

In some aspects, the first and second RNA oligomers do not comprise chemical modification. In some other aspects, the first and second RNA oligomers comprise chemical modification. The chemical modification may be, for example, modification with a hydrophobic group. Examples of the modification with a hydrophobic group may include cholesterol modification and tocopherol modification. Moreover, the chemical modification may also be, for example, polyethylene glycol modification.

It is to be noted that the definition of "chemical modification" does not include the triphosphoric acid structure at the 5'-terminus.

The first and second RNA oligomers can be prepared according to a known method or a method equivalent thereto. Specifically, the first and second RNA oligomers are each produced from a template DNA by in vitro transcription. In principle, the first and second RNA oligomers can be prepared in almost the same manner as the aforementioned production of the mRNA. However, although a 5' Cap analog is added to the mRNA upon the transcription thereof, such Cap analog is not added upon the production of the first and second RNA oligomers. Thus, when the first and second RNA oligomers are biologically prepared, they can have a triphosphoric acid structure at the 5'-terminus thereof. The method of removing triphosphoric acid is as described later. The RNA oligomer, which does not have a triphosphoric acid structure at the 5'-terminus thereof, can be chemically synthesized.

3.2.3. Double-Stranded RNA

Herein, the "double-stranded RNA" is formed by allowing the aforementioned mRNA to hybridize with at least one of the aforementioned first RNA oligomers, and also allowing the first RNA oligomer to hybridize with the second RNA oligomer. Moreover, the double-stranded RNA consisting of the first RNA oligomer and the second RNA oligomer hybridizing with the first RNA oligomer may also be referred to as a "double-stranded RNA oligomer" in some cases.

The double-stranded RNA can be prepared by hybridization of the mRNA with the first RNA oligomer and hybridization of the first RNA oligomer with the second RNA oligomer. More specifically, the hybridization can be carried out under the conditions described in the after-mentioned Examples, or conditions equivalent thereto.

The number of the first RNA oligomers hybridizing with a single mRNA is at least one, preferably 1 to 50, more preferably 1 to 15, and further preferably 1 to 5. If the number of the first RNA oligomers is within the range of 1 to 50, the translation efficiency of the mRNA can be maintained at a relatively high level. In addition, as the number of double-stranded RNA oligomers each consisting of a first RNA oligomer and a second RNA oligomer, which are allowed to hybridize with a single mRNA, increases, immunostimulation action is improved. Thus, the number of the double-stranded RNA oligomers each consisting of a first RNA oligomer and a second RNA oligomer, which are allowed to hybridize with a single mRNA, is controlled, so that an immune response can be controlled.

Hence, herein, provided is a method for controlling an immune response, comprising controlling the number of double-stranded RNA oligomers allowed to hybridize with a single mRNA.

Moreover, the number of the second RNA oligomers allowed to hybridize with a single first RNA oligomer is 1.

Hybridization of the RNA oligomer(s) with the mRNA can be carried out by applying a known method and known conditions. More specifically, in the hybridization, the reaction mixture is heated and is then left at rest for a certain period of time, and thereafter, the temperature is gradually decreased. The heating is carried out for the purpose of dissociating complementary bonds previously existing in the molecules of the mRNA or the oligomer(s), or among the molecules thereof, and thereby more efficiently binding the mRNA with the oligomer(s). The temperature and the time can be adjusted, as appropriate, as long as suitable hybridization can be guaranteed. In particular, since poly A or poly U is unlikely to bind to another sequence in advance, more moderate heating conditions can be determined. Moreover, moderate temperature decrease brings on an increase in the hybridization specificity. In addition, the chain length of the oligomer does not largely influence on determination of hybridization conditions. Hybridization conditions should be determined, as appropriate, while evaluating hybridization efficiency. For example, the methods and conditions described in the Examples later are applied.

In some aspects, the double-stranded RNA has a triphosphoric acid structure at the 5'-terminus of the RNA oligomer. Since the double-stranded RNA has such a triphosphoric acid structure at the 5'-terminus of the RNA oligomer, it can provoke a stronger inflammatory response.

In some other aspects, the double-stranded RNA does not have a triphosphoric acid structure at the 5'-terminus of the RNA oligomer. Triphosphorylation can be eliminated according to a known method or a method equivalent thereto. The method of eliminating triphosphorylation may be, for example, a method of using Antarctic phosphatase (New England Biolabs, cat. no. M0289S), as in the aftermentioned Examples.

In some aspects, the terminus of the double-stranded RNA on the side, at which the second RNA oligomer hybridizes with the first RNA oligomer, is a blunt end. It has been known that when the 5'-blunt end has a triphosphorylated structure, immune induction via RIG-I is improved. When an RNA comprising a triphosphorylated 5'-terminus is transcribed according to in vitro transcription, the RNA is designed, so that a complementary strand RNA to the transcribed RNA is not formed. Herein, the RNA is prepared, while nucleotides necessary for transcription of the complementary strand RNA are excluded. Thus, the template DNA is designed, such that the target RNA can be transcribed even though the aforementioned nucleotides are excluded. For example, when the sequence GUGUGUGUGU (SEQ ID NO: 67) is subjected to in vitro transcription, the sequence ACACACACAC (SEQ ID NO: 68) may be generated as a by-product. When A is removed and the sequence is then subjected to in vitro transcription, generation of this by-product is avoided.

In some aspects, the double-stranded RNA is in a naked form. That is, the double-stranded RNA is not loaded into carriers.

In some other aspects, the double-stranded RNA is in a form in which it is loaded in a carrier. The type of such a carrier is not particularly limited, as long as it can load the double-stranded mRNA therein and can deliver it to a preferred site in the body of a subject. The carrier is a lipidic mRNA carrier or a cationic polymer complex, and more preferably a polymeric micelle or a lipidic mRNA carrier.

The polymeric micelle has a two-layer structure consisting of an inner core formed with a condensed nucleic acid and a cationic polymer, and an outer shell formed with a hydrophilic polymer. The cationic polymer is, for example, a polyamino acid derivative. The hydrophilic polymer is, for example, polyethylene glycol ("PEG"). The inner core physically or chemically encapsulates the mRNA therein. The outer shell delivers the mRNA encapsulated in the inner core to predetermined tissues by its physicochemical properties. The polymeric micelle can enter the cells by endocytosis. The polymeric micelle can utilize, for example, the interaction of a polycation with a nucleic acid on a block polymer (polyion complex ("PIC")), and can also utilize a hybrid micelle of the polyion complex with an inorganic molecule. Examples of the PIC-type polymeric micelle may include PIC micelles formed by association of mRNA with PEG-PAsp (DET)-Chol, PEG-PAsp (DET), or PEG-PLys (see the Examples as described later), or other polycations such as PAsp(TET) or PAsp(TEP) used in block copolymers (Uchida, S., et al., Biomaterials (2016) 82, pp. 221-228), and those used in triblock copolymers (Osawa, S., et al., Biomacromolecules 17, pp. 354-361 (2016)). Examples of the hybrid micelle with an inorganic molecule may include PEGylated calcium phosphate (CaP) particles (Pittela, et al., Biomaterials (2011) 32, pp. 3106-3114) and PEGylated silica particles (Miyata, K., et al. Biomaterials (2010) 31, pp. 4764-4770).

The lipidic mRNA carrier is formed using a lipid or a cationic lipid as a carrier, and the lipidic mRNA carrier has a form, in which an mRNA is loaded in or bound to the lipidic mRNA carrier. The lipidic mRNA carrier is obtained by mixing an mRNA with one or more selected from the group consisting of: for example, cationic lipids such as N-[1-(2,3-dioleyloxy) propyl]-N,N,N-trimethylammonium chloride (DOTMA), 2,3-dioleyloxy-N-[2-(spermine carboxamido)ethyl]-N, N-dimethyl-1-propanaminium trifluoroacetic acid (DOSPA), 1,2-dioleoyl-3-(trimethylammonium) propane (DOTAP), N-[1-(2,3-dimyristyloxy)propyl]-N,N-dimethyl-N-(2-hydroxyethyl) ammonium bromide (DMRIE), or DC-Cholesterol; neutral phospholipids such as distearoylphosphatidylcholine (DSPC) or dioleoyl phosphatidylethanolamine (DOPE); PEGylated lipids; and cholesterols.

The cationic polymer complex is a mixture of an mRNA and, for example, linear or branched polyethylenimine, polylysine, polyarginine, a chitosan derivative, or a polymethacrylic acid derivative.

These carriers can be prepared by a known method or a method equivalent thereto.

3.2.4. Adjuvant

In some preferred aspects, the RNA vaccine is not used together with an adjuvant.

In some other aspects, the RNA vaccine is used together with an adjuvant. When the RNA vaccine is used together with an adjuvant, it may be formulated together with the adjuvant. The adjuvant is any given compound that is preferable for enhancing an immune response. Such an adjuvant is known, and a person skilled in the art can select a suitable adjuvant from any given adjuvants.

3.3. Prevention or Treatment of Disease

The mRNA vaccine can be used to prevent or treat a disease in a subject in need of the prevention or treatment of the disease.

Examples of the disease to be prevented or treated may include cancers, viral infections, bacterial infections, fungal infections, protozoal infections, and autoimmune diseases. These diseases can be prevented or treated by appropriately selecting the antigen encoded by the coding region of the aforementioned mRNA, depending on the disease to be prevented or treated.

The "subject" is a human, or an organism other than the human, such as, for example, birds and non-human mammals (e.g., bovines, monkeys, cats, mice, rats, Guinea pigs, hamsters, pigs, dogs, rabbits, sheep and horses).

The mRNA vaccine can be formulated according to an ordinary method. In some aspects, the mRNA vaccine comprises a pharmaceutically acceptable additive. Examples of the pharmaceutically acceptable additive may include water, a pharmaceutically acceptable organic solvent, collagen, polyvinyl alcohol, polyvinyl pyrrolidone, a carboxyvinyl polymer, sodium carboxymethyl cellulose, sodium polyacrylate, sodium alginate, water-soluble dextran, sodium carboxymethyl starch, pectin, methyl cellulose, ethyl cellulose, xanthan gum, gum Arabic, casein, agar, polyethylene glycol, diglycerin, glycerin, propylene glycol, Vaseline, paraffin, stearyl alcohol, stearic acid, human serum albumin, mannitol, sorbitol, lactose, and a pharmaceutically acceptable surfactant.

The additives are selected from the above-described additives depending on the dosage form of the mRNA vaccine, and are used alone or by appropriately being combined with one another. For example, when the mRNA vaccine is used as an injection preparation, the purified double-stranded RNA is dissolved in a solvent (e.g. a normal saline, a buffer, a dextrose solution, etc.), and Tween 80, Tween20, gelatin, human serum albumin, etc. are then added to the solution, and the obtained solution can be used as an injection preparation. Alternatively, in order to prepare a dosage form that is dissolved before use, the mRNA vaccine may be freeze-dried. Examples of an excipient for freeze-drying may include: sugars, such as mannitol, dextrose, lactose, sucrose, mannitol, or sorbitol; starches derived from corn, wheat, rice, potato, or other plants; celluloses, such as methyl cellulose, hydroxypropylmethyl cellulose, or carboxymethyl cellulose sodium; rubbers, such as gum Arabic or gum tragacanth; gelatin; and collagen.

The applied dose of the mRNA vaccine can be selected, as appropriate, depending on the age, sex and symptoms of a subject, administration route, the number of administrations, dosage form, etc. The effective dose of the mRNA vaccine means the amount of the vaccine that reduces the symptoms or conditions of the disease. The therapeutic effects and toxicity of such an mRNA vaccine can be determined by standard pharmaceutical procedures applied to cell cultures or experimental animals, for example, based on ED50 (the dose that is therapeutically effective for 50% of a population) and LD50 (the dose that is lethal to 50% of a population). In some aspects, the dose of the mRNA vaccine can be set at an mRNA dose range of 10 ng to 1 g, 100 ng to 100 mg, 1 μg to 10 μg, or 30 μg to 300 μg per adult per day.

The administration route of the mRNA vaccine can be selected, as appropriate. Examples of the administration route may include transdermal, intranasal, transbronchial, intramuscular, intraperitoneal, intravenous, subcutaneous, intrarectal, and intravaginal administrations, but are not limited thereto.

The number of administrations of the mRNA vaccine can be set at once or several times, as long as side effects are within a clinically acceptable range.

In some aspects, an antibody titer or cellular immunity activity in the administration of the mRNA vaccine is measured. For example, then antibody titer can be evaluated by collecting blood from a living body and then quantifying IgG in the serum. The cellular immunity activity can be evaluated by separating lymphocytes from a living body, then culturing them, and then measuring incorporation of $^3$H-thymidine.

3.4. Kit

The kit of the third aspect of the present invention is characterized in that it includes the above-described mRNA vaccine. The present kit can be preferably used, for example, in a method for treating various types of diseases using the above-described mRNA vaccine.

In the kit, the storage state of the above-described mRNA vaccine is not limited. Taking into consideration stability (storability), the ease of use, etc., the state of a solution, powder or the like can be selected.

The kit may include other components, as well as the above-described mRNA vaccine. Examples of such other components may include various types of buffers and an instruction manual (use manual). The kit may include or may not include an adjuvant. Preferably, the kit does not include an adjuvant.

The present invention will be described in more detail in the following Examples. However, it should not be understood that the present invention is limited to these Examples.

EXAMPLES

Example 1-1: Synthesis of Various Types of Block Copolymers 1.1. Synthesis of PEG-PAsp(DET)-Chol PEG-PAsp(DET)-Chol was synthesized according to the previous report (Oba, M., et al., *Biomaterials* (2011) 32, pp. 652-663) (Scheme 1). The following synthetic scheme was applied.

Scheme 1

[Formula 1]

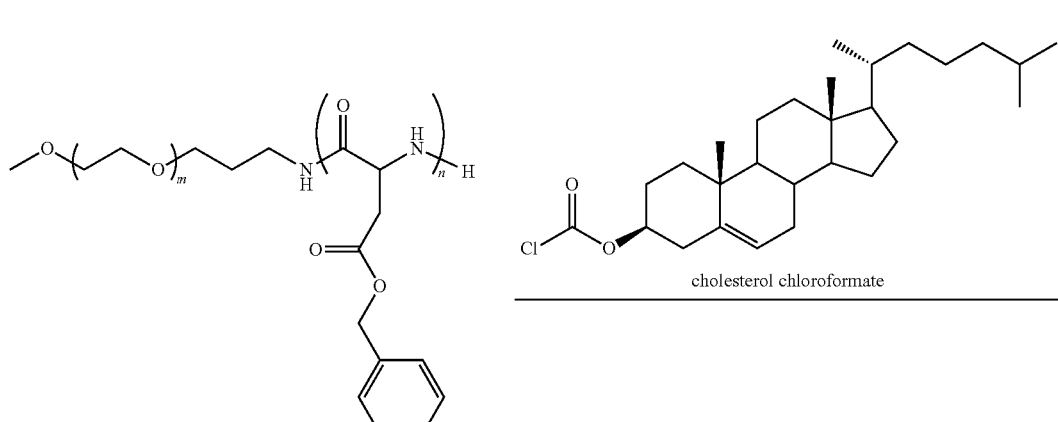

PEG-PBLA

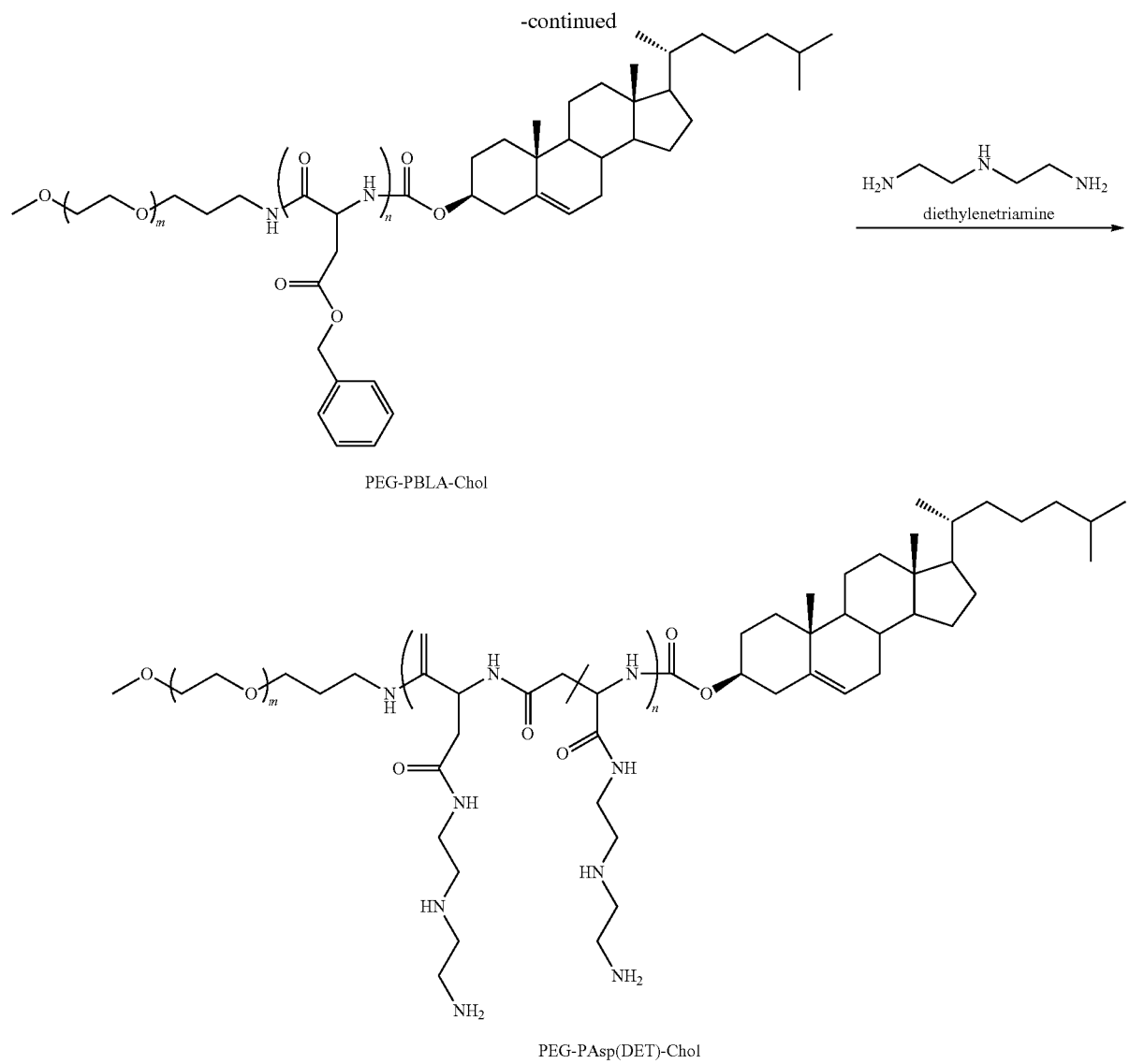

PEG-PBLA-Chol

PEG-PAsp(DET)-Chol

First, using α-methoxy-ω-amino-polyethylene glycol (MeO-PEG-NH2, $M_w$ of PEG: 12 kDa) as an initiator, β-benzyl-L-aspartate-N-carboxylic acid anhydride (NCA-BLA) was subjected to ring-opening polymerization, so as to synthesize PEG-poly(β-benzyl L-aspartate) (PEG-PBLA). 505 mg of MeO-PEG-NH2 was dissolved in benzene, and was then freeze-dried overnight. After completion of the freeze-drying, MeO-PEG-NH2 and NCA-BLA were completely dissolved in a mixed solvent of dimethylformamide (DMF):dichloromethane (DCM) (=1:10) under Ar atmosphere. The NCA-BLA solution was added to the MeO-PEG-NH2 solution, and the mixed solution was then stirred at 25° C. for 3 days. Thereafter, the reaction solution was re-precipitated in an n-hexane/ethyl acetate (3:2) mixed solution to recover PEG-PBLA. Thereafter, PEG-PBLA was vacuum-dried to obtain white powders. The polymerization degree of PBLA was 68 (n=68). Besides, in the above formula, m=293.

Subsequently, a cholesterol group was introduced into the ω terminus of the synthesized PEG-PBLA. Cholesterol chloroformate (328 mg) dissolved in a 11% (v/v) triethylamine (TEA)/DCM mixed solution (200 μL) was slowly added into PEG-PBLA (200 mg) dissolved in DCM (4 mL), and the obtained mixture was then stirred at room temperature for 24 hours. Thereafter, the reaction solution was re-precipitated in diethyl ether, and PEG-PBLA-Cholesterol (Chol) was then recovered.

The recovered PEG-PBLA-Chol was subjected to an aminolysis reaction to synthesize PEG-PAsp(DET)-Chol. PEG-PBLA-Chol (100 mg) was dissolved in benzene and was then freeze-dried, and the dried PEG-PBLA-Chol and dry diethylenetriamine (DET) (in an amount of 50 equivalents with respect to the amount of PBLA) were then dissolved in N-methyl-2-pyrrolidone (NMP) containing 0.5 M thiourea. The thus obtained solution was cooled to 10° C., and the PEG-PBLA-Chol solution was then slowly added dropwise onto the DET solution, and the mixed solution was then stirred for 1 hour. After completion of the reaction, while the temperature of the solution was kept at 10° C. or lower, the reaction solution was neutralized with a 5 N HCl aqueous solution, and was then dialyzed against a 0.01 N HCl aqueous solution at 4° C. for 1 day. Thereafter, the resultant was dialyzed against ion exchange water at 4° C. for one more day. After completion of the dialysis, the resulting solution was freeze-dried to obtain PEG-PAsp (DET)-Chol in the form of white powders.

1.2. Synthesis of PEG-PAsp(DET)

Also, PEG-PAsp(DET) was synthesized by subjecting PEG-PBLA to the same aminolysis reaction as described above (Scheme 2).

Scheme 2

[Formula 2]

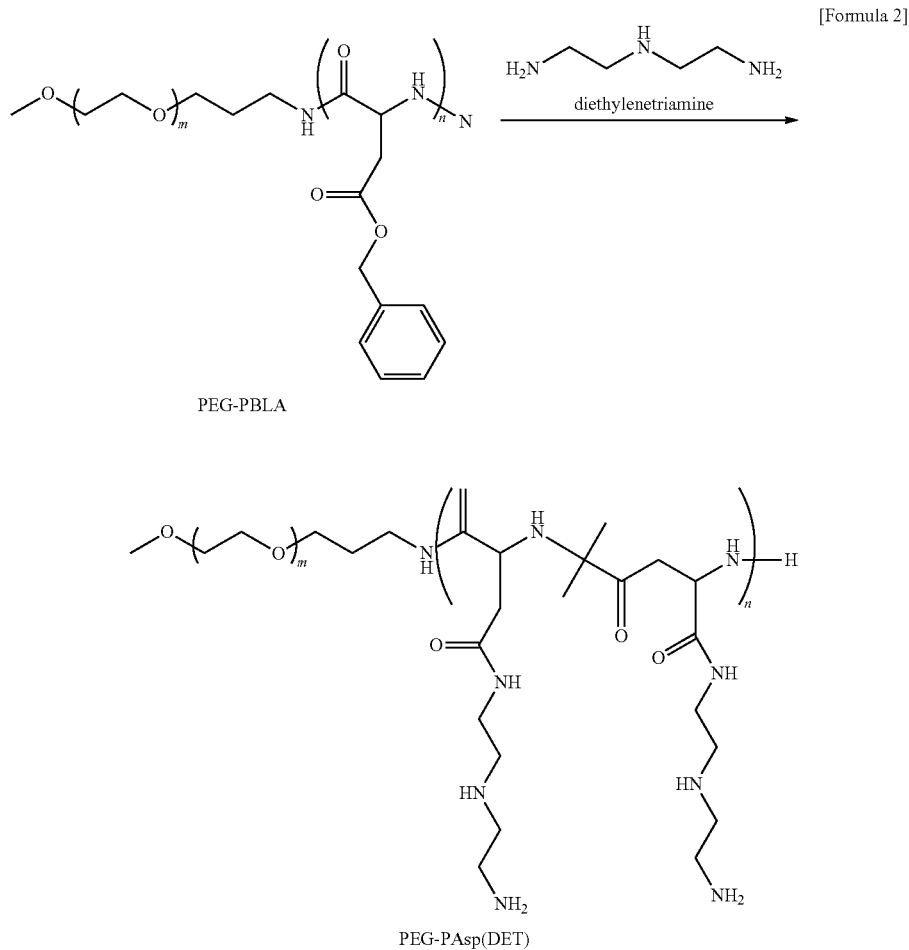

PEG-PBLA (200 mg) was dissolved in benzene and was then freeze-dried, and the dried PEG-PBLA and dry diethylenetriamine (DET) (in an amount of 50 equivalents with respect to the amount of PBLA) were then dissolved in NMP containing 0.5 M thiourea. The thus obtained solution was cooled to 10° C., and the PEG-PBLA solution was then slowly added dropwise onto the DET solution, and the mixed solution was then stirred for 1 hour. After completion of the reaction, while the temperature of the solution was kept at 10° C. or lower, the reaction solution was neutralized with a 5 N HCl aqueous solution, and was then dialyzed against a 0.01 N HCl aqueous solution at 4° C. for 1 day. Thereafter, the resultant was dialyzed against ion exchange water at 4° C. for one more day. After completion of the dialysis, the resulting solution was freeze-dried to obtain PEG-PAsp(DET) in the form of white powders. Besides, in the above formula, n=68, and m=293.

Example 1-2: Preparation of mRNA

An mRNA is generally prepared from a template DNA according to in vitro transcription. Herein, a template DNA was produced as follows. First, a T7-Gluc plasmid was produced by inserting a Gluc coding sequence (FIG. 15 and SEQ ID NO: 32) from pCMV-Gluc control plasmid (New England BioLabs, Ipswich, Mass., USA) into the HindIII-XbaI site of a pSP73 vector (Promega). Thereafter, a T7-Gluc poly A120 plasmid was produced by inserting A120-(BsmBI cleavage site) into the EcoR1-Bgl2 site of the T7-Gluc plasmid. Thereafter, the resultant was cleaved with BsmBI, and was then blunt-ended with T4 DNA Polymerase (Takara Bio, Inc.), and the obtained product was then used in the subsequent in vitro transcription.

Using mMESSAGE mMACHINE (trade name) T7 (Thermo Fisher Scientific), the above-obtained product encoding Gaussia luciferase (Gluc) was subjected to a restriction enzyme treatment, and the blunt-ended template DNA (T7-Gluc poly A120 plasmid) was then transcribed under in vitro environment, so as to produce an mRNA. The transcribed mRNA was purified using RNeasy Mini Kit (QIAGEN), and was then recovered. The concentration of the recovered mRNA was measured using NanoDrop (Thermo Fisher Scientific). Moreover, whether the target mRNA was produced was confirmed by electrophoresis using Agilent 2100 Bioanalyzer (Agilent technologies).

Using NanoDrop, it was confirmed that a high-purity mRNA, in which the ratio between the absorbance at 260 nm and the absorbance at 280 nm was 2.0 to 2.2, was produced at a high concentration of 500 to 1,000 ng/μL. Moreover, according to the analysis using the Bioanalyzer, production of an mRNA having the intended size was confirmed.

The sequence of the produced mRNA is shown in FIG. 14 and SEQ ID NO: 1. In the sequence shown in FIG. 14, the underlined portion indicates an open reading frame (ORF). 5' UTR (54 nucleotides) is located upstream of the ORF and 3' UTR (52 nucleotides) is located downstream of the ORF. 120A located further downstream thereof indicates a poly A sequence.

Herein, regarding the number of Poly A, theoretically, 120 bp are incorporated into the template DNA, and in mRNA, it is 119 nucleotides. However, the number of Poly A may be increased or decreased at the stage of DNA amplification or preparation of the mRNA.

Example 1-3: Hybridization of RNA Oligomer

An RNA oligomer was designed and prepared, as follows. Using RNA secondary structure predicting software (http://rtips.dna.bio.keio.ac.jp/ipknot/), the secondary structure of the Glue mRNA was predicted, and an RNA oligomer was then designed with respect to a portion of the RNA strand, which did not have a secondary structure. The present inventors asked Hokkaido System Science Co., Ltd. to synthesize the RNA oligomer, including cholesterol modification on the 5'-terminus or 3'-terminus. It is to be noted that the underlined portions in the sequences of the following RNA oligomers each indicate an overhang sequence. Moreover, mismatch Chol-RNA oligo indicates 19-mer Chol modified poly A that does not hybridize with the mRNA. "Chol-overhang" indicates that the 5'-terminus of the RNA oligomer has been subjected to cholesterol modification, whereas "Chol-overhang 3'" indicates that the 3'-terminus of the RNA oligomer has been subjected to cholesterol modification.

```
RNA oligomers:
17-mer (1) (SEQ ID NO: 2):
UCUUUGAGCACCUCCAG 17-mer (2) (SEQ ID NO: 3):
CUCUAGAUGCAUGCUCG 17-mer (3) (SEQ ID NO: 4):
CUCGGCCACAGCGAUGC 17-mer (4) (SEQ ID NO: 5):
GCGGCAGCCACUUCUUG 17-mer (5) (SEQ ID NO: 6):
AUCUCAGGAAUGUCGAC 23-mer (SEQ ID NO: 7):
UCCAUCUCUUUGAGCACCUCCAG 40-mer (SEQ ID NO: 8):
CUUUCCGGGCAUUGGCUUCCAUCUCUUUGAGCACCUCCAG 60-mer (SEQ ID NO: 9):
ACAGCCCCUGGUGCAGCCAGCUUUCCGGGCAUUGGCUUCCAUCUCUUUGAG
CACCUCCAG Overhang 2base (1) (SEQ ID NO: 10):
AAUCUUUGAGCACCUCCAG -continued
Chol-overhang 0(1) (17-mer (1); SEQ ID NO: 2):
UCUUUGAGCACCUCCAG Chol-overhang 2base (1) (SEQ ID NO: 10):
AAUCUUUGAGCACCUCCAG Chol-overhang 5base (1) (SEQ ID NO: 11):
AAUAAUCUUUGAGCACCUCCAG Chol-overhang 0(2) (17-mer (2); SEQ ID NO: 3):
CUCUAGAUGCAUGCUCG Chol-overhang 2base (2) (SEQ ID NO: 12):
AACUCUAGAUGCAUGCUCG Chol-overhang 5base (2) (SEQ ID NO: 13):
AAUAACUCUAGAUGCAUGCUCG Chol-overhang 2base (3) (SEQ ID NO: 14):
AACUCGGCCACAGCGAUGC Chol-overhang 2base (4) (SEQ ID NO: 15):
AAGCGGCAGCCACUUCUUG Chol-overhang 2base (5) (SEQ ID NO: 16):
AUAUCUCAGGAAUGUCGAC Chol-overhang 2base (6) (SEQ ID NO: 17):
AAGCAGCCAGCUUUCCCGG Chol-overhang 2base (7) (SEQ ID NO: 18):
AAACUCUUUGUCGCCUUCG Chol-overhang 2base (8) (SEQ ID NO: 19):
AAUUGAGGCAGCCAGUUGU Chol-overhang 2base (9) (SEQ ID NO: 20):
UAGUGGGACAGGCAGAUCA Chol-overhang 2base (10) (SEQ ID NO: 21):
AAUUGAAGUCUUCGUUGUU Chol-overhang 2base (11) (SEQ ID NO: 22):
AAUUUUUUUUUUUUUUUUU Chol-overhang 3' 2base (1) (SEQ ID NO: 23):
UCUUUGAGCACCUCCAGAU Mismatch Chol-RNA oligo (SEQ ID NO: 24):
AAAAAAAAAAAAAAAAAAA
```

The RNA oligomer (overhang 2base (1)) in an amount of 1 equivalent of the mRNA was heated at 65° C. for 5 minutes, and was then cooled to 30° C. over 10 minutes, so as to perform hybridization. The prepared RNA oligomer-modified mRNA was evaluated by polyacrylamide gel electrophoresis. A glycerol solution was added to the mRNA solution (1×TBE buffer) to a final concentration of 5 wt %, and electrophoresis was then carried out under conditions of 100 V, 800 mA, 200 W, and 30 min.

The results are shown in FIG. 1. FIG. 1(2) and (3) show the electrophoresis performed on the Chol-unmodified RNA oligomer (overhang 2base (1)) and the electrophoresis performed on a non-hybridizing mRNA, respectively. In FIG. 1(1), only the RNA oligomer (overhang 2base (1)) that was in an amount of 1/16 of the amount hybridized in FIG. 1(2) was electrophoresed. If hybridization had not taken place in FIG. 1(2), a band derived from the RNA oligomer would have been seen at the same position as that in FIG. 1(1). However, in reality, such a band was hardly seen. That is, hybridization of a majority of RNA oligomers was confirmed.

Thus, in the present Example, hybridization of the RNA oligomers could be confirmed.

Example 1-4: Evaluation of mRNA Expression Ability in Cultured Cells and Cell-Free System In the evaluation using cultured cells, RAW264.7 cells were seeded on a 12-well plate to a cell density of 300,000 cells/well, and were then incubated in a Dulbecco's Modified Eagle Medium (DMEM) supplemented with 10% (v/v) fetal bovine serum (FBS) for 24 hours. After completion of the incubation, DMEM was replaced with Opti-MEM (trade name) (Thermo Fisher Scientific). Thereafter, a complex consisting of Lipofectamine (trade name) LTX (Thermo Fisher Scientific) and an mRNA was added to the reaction mixture, so that the Gluc mRNA prepared in Example 1-2 or the Gluc mRNA prepared in Example 1-3, which had hybridized with an RNA oligomer (17-mer (1), 23-mer, 40-mer, or 60-mer), became 1 μg/well. Four hours after the transfection, the medium was recovered, and the amount of Gluc contained in the medium was evaluated using a luminometer.

In the evaluation using a cell-free system, Rabbit Reticulocyte Lysate System (Promega) was used to evaluate the expression ability of the mRNA prepared in Example 1-2 or the Gluc mRNA prepared in Example 1-3, which had hybridized with an RNA oligomer (17-mer (1), 23-mer, 40-mer, or 60-mer). In accordance with the protocols, a mixed solution comprising the mRNA was prepared, and was then incubated at 30° C. for 90 minutes. The expressed Gluc was evaluated by measuring the luminescent intensity using a luminometer.

The results are shown in FIG. 2. As shown in FIG. 2(A), when the efficiency of mRNA introduction into the cultured cells, the expression level of Gluc was significantly decreased in the case of the mRNA hybridizing with an oligomer having a chain length of 23-mer or more (23-mer, 40-mer, 60-mer), in comparison to the case of using the non-hybridizing mRNA (oligo(−)). On the other hand, the expression level of Gluc in the case of using the mRNA modified with a 17-mer oligomer was almost equivalent to that in the case of using the non-hybridizing mRNA. Meanwhile, as shown in FIG. 2(B), the protein translation efficiency in the cell-free system was constant, regardless of the chain length of the RNA oligomer, and it was almost the same level as that of the non-hybridizing mRNA. That is to say, in the cell-free system, a decrease in the translation efficiency was not observed due to hybridization. From the aforementioned experiments, it was found that the expression level is slightly decreased in the case of hybridization with an oligomer with a long chain length due to certain mechanism in the cells. From these results, it was revealed that the chain length of an RNA oligomer is desirably set at 12 to 40-mer.

Herein, in FIG. 2, "" and "*" indicate that there is a statistically significant difference of $p<0.01$ and $p<0.001$, when compared with the case of not performing oligo modification. For the statistical treatment, after completion of an ANOVA test, a Dunnett's test was carried out using, as a control, the case of not performing oligo modification.

As such, in the present Example, as a result of confirming the efficiency of mRNA introduction into the cultured cells, it could be confirmed that the expression is slightly decreased in the case of an RNA oligomer having a long chain length, but that the expression can be favorably maintained in the case of a 17-mer RNA oligomer (FIG. 2(A)). On the other hand, regarding the protein translation efficiency in the cell-free system, it could be confirmed that the expression level is constant regardless of the chain length of the RNA oligomer (FIG. 2(B)).

Example 1-5: Preparation of PMs Loading mRNA Therein

In the present Example, the Gluc mRNA prepared in Example 1-2, or the Gluc mRNA prepared in Example 1-3 hybridizing with an RNA oligomer (overhang 2base (1) or Chol-overhang 2base (1)) was used.

PEG-PAsp(DET)-Chol and Gluc mRNA were each independently dissolved in a 10 mM HEPES buffer (pH 7.4). The concentration of the PEG-PAsp(DET)-Chol was adjusted, so that the ((positive charge number of PAsp(DET))/(negative charge number of mRNA)) ($N^+/P^−$ ratio) became 1.5 at pH 7.4. The PEG-PAsp(DET)-Chol solution was added to the mRNA solution, so that the final concentration of the mRNA became 33.3 μg/mL, thereby preparing polymeric micelles (PMs). The particle diameter and polydispersity of the PMs were evaluated using ZetasizerNano (Malver Instruments). In addition, using a transmission electron microscope (TEM), the prepared PMs were observed. Also, PMs consisting of PEG-PAsp(DET) were prepared by the same method as described above.

The results are shown in Tables 1 and 2 and FIG. 3.

TABLE 1

Hydrodynamic radius of mRNA-loading PMs according to DLS measurement

| mRNA | PEG-PAsp(DET) | PEG-PAsp(DET)-Chol |
|---|---|---|
| Oligo(−) | 48 nm | 46 nm |
| Modified with RNA oligo | 42 nm | 47 nm |
| Modified with Chol-RNA oligo | 54 nm | 49 nm |

TABLE 2

Core size of PMs by TEM observation

| | Core size (nm) Block copolymers | |
|---|---|---|
| mRNA | PEG-PAsp(DET) | PEG-PAsp(DET)-Chol |
| Oligo(−) | 25 ± 0.23 | 22 ± 0.23 |
| Modified with RNA oligo | 21 ± 0.17 | 21 ± 0.23 |
| Modified with Chol-RNA oligo | 21 ± 0.22 | 21 ± 0.27 |

Example 1-6: Enzyme Resistance Test in Serum

In the present Example, the Gluc mRNA prepared in Example 1-2, or the Gluc mRNA prepared in Example 1-3 hybridizing with each of the following RNA oligomers was used.

RNA oligomers used in the experiments in FIGS. 4(A) and (B):
  Chol-overhang 0(1)
  Chol-overhang 2base (1)
  Chol-overhang 5base (1)
  Mismatch Chol-RNA oligo RNA oligomers used in the experiments in FIGS. 4(C) and (D):
  Chol-overhang 0(2)
  Chol-overhang 2base (2)
  Chol-overhang 5base (2)
  Mismatch Chol-RNA oligo RNA oligomer used in the experiments in FIG. 4(E):
Chol-overhang 2base (11)

Individual PMs were prepared under the same conditions as those in Example 5. It is to be noted that PEG-PAsp (DET)-Chol was used in the experiments shown in FIGS. 4(A), (C) and (E), whereas PEG-PAsp(DET) was used in the experiments shown in FIGS. 4(B) and (D).

Fetal bovine serum (FBS) was diluted with a 10 mM HEPES buffer (pH 7.4) to a predetermined concentration, and a PM solution was then added to the diluted solution. The mixed solution was left at rest at 37° C. for 15 minutes. Thereafter, RNA was extracted from the resulting solution, using RNeasy Mini Kit (QIAGEN). The extracted RNA was reverse-transcribed to complementary DNA (cDNA), and the amount of remaining cDNA was quantified and evaluated according to qRT-PCR. The result was shown as a relative value, while the amount of mRNA that had not been left at rest in the presence of FBS at 37° C. was set at 100%.

The results are shown in FIG. 4. As shown in FIG. 4(A), in the case of using PEG-PAsp(DET)-Chol, in a group involving hybridization with an oligomer having a 2-base overhang, significant improvement of the stability in serum was observed in comparison to a group not involving such hybridization. Besides, in the case of not having an overhang, the stability tended to be improved, but a significant difference could not be obtained. In the case of having a 5-base overhang, stabilizing effects were not observed. On the other hand, in the case of using PEG-PAsp(DET), in a group not having an overhang, and in a group having a 2-base overhang, the improvement of stability was observed (FIG. 4(B)). These data were reproduced even in the case of using another oligo having a different hybridization site (FIG. 4(C): PEG-PAsp(DET)-Chol, and FIG. 4(D): PEG-PAsp(DET)). In the mismatch Chol-RNA oligo, PM was formed by mixing an mRNA and 19-mer Chol modified poly A not hybridizing with the mRNA. In this case, enzyme resistance in the serum was not improved, and thus, it was suggested that hybridization should be performed to obtain effects.

Also, with regard to PM consisting of an mRNA hybridizing with Chol modified oligo having a 2-base overhang to a poly A sequence, and PEG-PAsp(DET)-Chol, stabilization effect caused by the hybridization was observed (FIG. 4(E)).

Hence, in the case of using PEG-PAsp(DET)-Chol, it was found that it exhibited particularly high stability, when a cholesterol-modified oligomer having a 2-base overhang was used (FIGS. 4(A) and (C)). On the other hand, in the case of using PEG-PAsp(DET), the improvement of stability was observed both in the case of not having an overhang and in the case of having a 2-base overhang (FIGS. 4(B) and (D)). Moreover, regarding the hybridization position, it became clear that stability is improved not only when the hybridization position is a protein coding sequence, but also is a poly A portion (FIG. 4(E)).

Example 1-7: Agarose Gel Electrophoresis

In the present Example, the Gluc mRNA prepared in Example 1-2 or the Glue mRNA prepared in Example 1-3 hybridizing with the RNA oligomer (Chol-overhang 2base (1)) was used.

Individual PMs were prepared under the same conditions as those in Example 5.

A 1×TAE buffer (Tris-acetic acid-EDTA buffer) was prepared to result in 40 mM Tris, 20 mM acetic acid, and 1 mM ethylenediaminetetraacetic acid (EDTA).2 Na, and the prepared buffer was then adjusted to pH 7.4 with a sodium hydroxide aqueous solution. The thus obtained solution was used as an electrophoretic buffer. Thereafter, 0.9 wt % agarose gel was prepared, and 5 µL of dextran sulfate and 5 µL of 750 mM NaCl solution were then added to 15 µL of PM solution, depending on the A/P ratio (negative charge number of polyanion/number of phosphoric acid groups in mRNA). Thereafter, the obtained mixture was incubated at 37° C. for 1 hour. After completion of the incubation, 2.5 µL of loading buffer was added to the reaction mixture, and the obtained mixture was then electrophoresed at 100 V for 60 minutes. Thus, the presence or absence of the release of the mRNA was confirmed.

The results are shown in FIG. 5.

In FIG. 5(A) to (D), a naked mRNA was placed on the leftmost lane. When the mRNA was released from the micelles, the band was found at the same position as in the case of the naked mRNA. When the mRNA did not hybridize with a Chol modified oligomer, namely, in the case of using the PEG-PAsp(DET)-Chol shown in FIG. 5(A) and in the case of using the PEG-PAsp(DET) shown in FIG. 5(C), at an A/P ratio from 1.5 to 2, the release of a large amount of mRNA from the micelles was observed. In contrast, when the mRNA hybridizing with a Chol modified oligomer, the release of the mRNA was not observed so much, even at an A/P ratio of 2, even in the case of using any Chol modified oligomers (FIGS. 5(B) and (D)).

As such, it was found that the release of the mRNA was suppressed by Chol oligo (FIGS. 5(B) and (D)).

Example 1-8: Enzyme Resistance Test in Serum in Case of Increasing Number of Hybridizing Oligomers In the present Example, the Gluc mRNA prepared in Example 1-2 or the Glue mRNA prepared in Example 1-3 hybridizing with each of the following RNA oligomers was used.

Chol-overhang 2base (1)
Chol-overhang 2base (2)
Chol-overhang 2base (3)
Chol-overhang 2base (4)
Chol-overhang 2base (5)

Individual PMs were prepared under the same conditions as those in Example 1-5, using PEG-PAsp(DET)-Chol.

An mRNA hybridizing with a Chol modified oligomer(s) at one or five sites thereof was used, and an experiment was carried out by the same method as that of Example 1-6. Besides, in Unmodified Oligo, overhang 2base (1) was used. In the experiment using a single Chol modified oligomer (Chol oligo X1), Chol-overhang 2base (1) was used. In the experiment using five Chol modified oligomers (Chol oligo X5), Chol-overhang 2base (1) to (5) were used.

The results are shown in FIG. 6. In comparison to a non-hybridizing mRNA, an mRNA hybridizing with a Chol modified oligomer at a single site (Chol oligo X1) was improved in terms of stability, and further, an mRNA hybridizing with Chol modified oligomers at five sites (Chol oligo X5) exhibited further higher stability than the mRNA hybridizing with a Chol modified oligomer at a single site (Chol oligo X1).

Example 1-9: PMs Luciferase Expression Test

In the present Example, the Glue mRNA prepared in Example 1-2, or the Glue mRNA prepared in Example 1-3 hybridizing with each of the following RNA oligomers was used.

Chol-overhang 2base (1)
Chol-overhang 2base (2)
Chol-overhang 2base (3)

Chol-overhang 2base (4)
Chol-overhang 2base (5)
17-mer (1)

Individual PMs were prepared under the same conditions as those in Example 5, using PEG-PAsp(DET)-Chol.

HuH-7 cells (5,000 cells/well) were seeded on a 96-well plate, and were then incubated in DMEM (100 µL) supplemented with 10% (v/v) FBS for 24 hours. Thereafter, the medium was replaced with a new medium supplemented with 10% (v/v) FBS, and 7.5 µL of PMs solution containing 250 ng of mRNA was then added thereto. After completion of the incubation of the mixture for 24 hours, 10 µL of a supernatant of DMEM was recovered, and the luminescent intensity of Gluc was then measured using a luminometer.

The mRNA hybridizing with a Chol modified oligomer(s) at one or five sites thereof was used. In the experiment using a single Chol modified oligomer (Chol oligo X1), Chol-overhang 2base (1) was used. In the experiment using five Chol modified oligomers (Chol oligo X5), Chol-overhang 2base (1) to (5) were used. Moreover, in the experiment using an unmodified oligomer (Unmodified Oligo), overhang 2base (1) 17-mer (1) was used.

The results are shown in FIG. 7. A group involving introduction of an mRNA modified with 1 or 5 Chol oligomers (Chol oligo X1 or Chol oligo X5) exhibited high efficiency of luciferase expression from the mRNA, in comparison to a group involving introduction of an mRNA that did not hybridize with an oligomer (Hybridize (−)), or a group involving introduction of an mRNA modified with an oligomer unmodified with Chol (Unmodified Oligo).

Hence, it was found that the expression is increased by modification with Chol oligo. Moreover, no difference was found depending on the number of oligomers.

Example 1-10: Comparison Between 5'-Terminal Side Chol Modification and 3'-Terminal Side Chol Modification In the present Example, the Gluc mRNA prepared in Example 1-2, the Gluc mRNA prepared in Example 1-3 hybridizing with the following RNA oligomer, or a Gluc mRNA hybridizing with the following oligomer that is designed at the same position as above and has a 2-base overhang sequence on the 3'-terminal side, was used.
Chol-overhang 2base (1)
Chol-overhang 3' 2base (1)

Individual PMs were prepared under the same conditions as those in Example 5, using PEG-PAsp(DET)-Chol. A serum resistance test was carried out by the same method as that of Example 1-8, PM were then introduced into HuH-7 cells by the same method as that of Example 1-9, and the expression level of Gluc was then evaluated. The results of the serum resistance test are shown in FIG. 8(A), and the results of the expression level of Gluc are shown in FIG. 8(B). In both of the evaluations, a large difference was not observed between the 3'-terminal side and the 5'-terminal side as a Chol modification position.

Example 1-11: Evaluation of Translation Efficiency from Chol Modified mRNA in Cell-Free System In the present Example, the Gluc mRNA prepared in Example 1-2, or the Gluc mRNA prepared in Example 1-3 hybridizing with each of the following RNA oligomers was used.
Chol-overhang 2base (1)
Chol-overhang 2base (2)
Chol-overhang 2base (3)
Chol-overhang 2base (4)
Chol-overhang 2base (5)

In this evaluation, the mRNA was not loaded into PM, and a naked form of mRNA was used.

In the evaluation using a cell-free system, Rabbit Reticulocyte Lysate System (Promega) was used to evaluate the expression ability of an mRNA modified with a Chol-RNA oligomer. In accordance with the protocols, a mixed solution comprising the mRNA was prepared, and was then incubated at 30° C. for 90 minutes. The expressed Gluc was evaluated by measuring the luminescent intensity using a luminometer.

The results are shown in FIG. 9. It was confirmed that the efficiency of protein translation from the mRNA hybridizing with the Chol-RNA oligomer in a cell-free system is decreased, as the number of Chol-RNA oligomers is increased. That is to say, it became clear that a plurality of Chol groups decrease protein translation efficiency from the mRNA.

Herein, in an experiment in which the number of Chol-RNA oligomers was 1, Chol-overhang 2base (1) was used. In an experiment in which the number of Chol-RNA oligomers was 2, Chol-overhang 2base (1) and (3) were used. In an experiment in which the number of Chol-RNA oligomers was 3, Chol-overhang 2base (1) to (3) were used. In an experiment in which the number of Chol-RNA oligomers was 4, Chol-overhang 2base (1) to (4) were used. In an experiment in which the number of Chol-RNA oligomers was 5, Chol-overhang 2base (1) to (5) were used.

Example 1-12: Influence on Expression of Endogenous Gene

In the present Example, the following RNA oligomers that were designed and prepared in the same manner as that of Example 1-3, or the following siRNAs prepared as described below were used. "Chol-" indicates that the 5'-terminus of the RNA oligomer is modified with cholesterol.

Herein, the sequence of Luc mRNA used in the designing of RNA oligomers is shown in FIG. 16 and SEQ ID NO: 33.

```
luc oligo (SEQ ID NO: 25):
UCGAAGUACUCAGCGUA

Chol-oligo luc (SEQ ID NO: 26):
AAUCGAAGUACUCAGCGUA oligo Scr (SEQ ID NO: 27):
UCUUUGAGCACCUCCAG Chol-oligo Scr (SEQ ID NO: 27):
UCUUUGAGCACCUCCAG siLuc (sense strand) (SEQ ID NO: 28):
CUUACGCUGAGUACUUCGAdTdT siLuc (antisense strand) (SEQ ID NO: 29):
UCGAAGUACUCAGCGUAAGdTdT siScramble (siScr) (sense strand) (SEQ ID NO: 30):
UUCUCCGAACGUGUCACGUdTdT siScr (antisense strand) (SEQ ID NO: 31):
ACGUGACACGUUCGGAGAAdTdT
```

Herein, the present inventors asked Hokkaido System Science Co., Ltd. to synthesize siRNAs, and then, directly used the synthesized siRNAs.

Hela-luc cells (Caliper LifeScience) (5,000 cells/well) constantly expressing Luc were seeded on a 96-well plate, and were then incubated in DMEM (100 μL) supplemented with 10% (v/v) FBS for 24 hours. Thereafter, the medium was replaced with a serum-free medium (Opti-MEM (trade name) (Thermo Fisher Scientific)) (100 μL), and a complex consisting of Lipofectamine RNAiMax (Thermo Fisher Scientific) and RNA oligo or siRNA was then added to the cells. After completion of the incubation for 4 hours, the added each complex was removed. Twenty-four hours after the transfection, the resulting cells were dissolved in a Cell lysate buffer, and the expression level of luciferase in 10 μL of the cell lysate was then evaluated using a luminometer.

Figure 10:
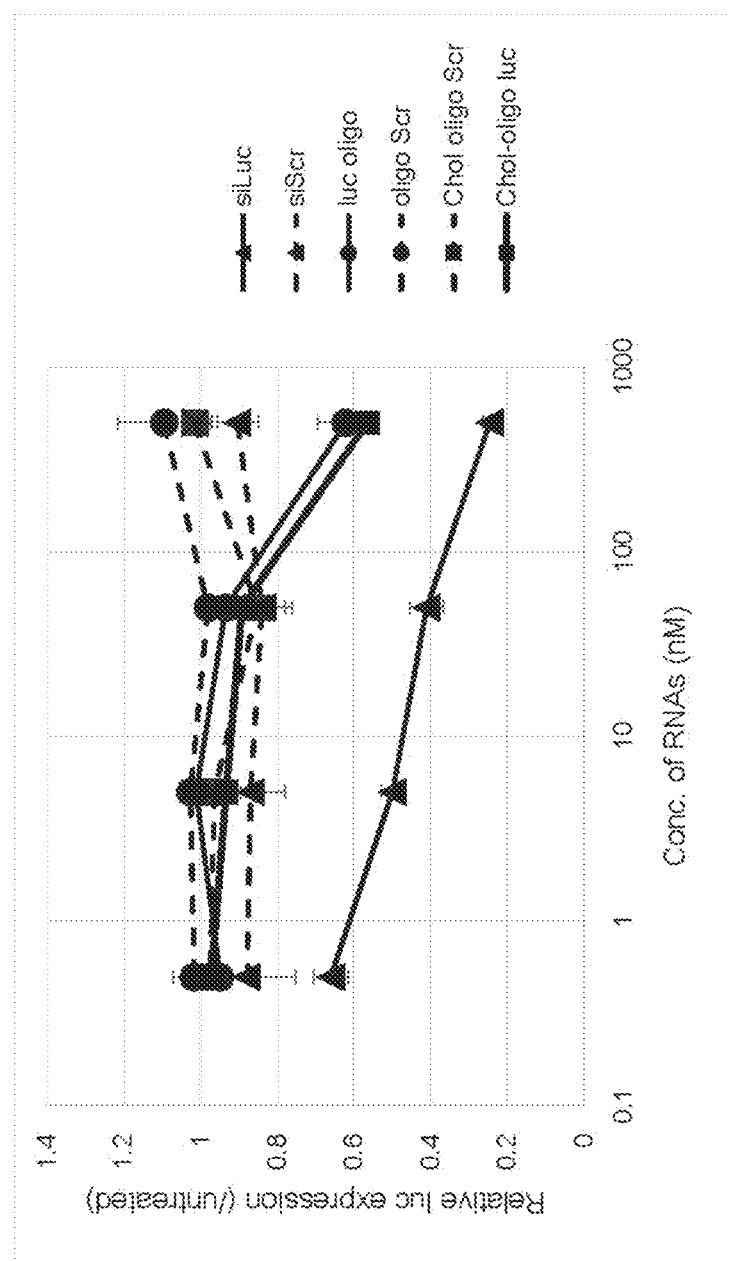
FIG. 10 is a view showing the influence of a Chol modified RNA oligomer on the expression of an endogenous gene.

The results are shown in FIG. 10. Herein, siLuc, Luc Oligo, and Chol Oligo Luc indicate, respectively, siRNA, unmodified RNA Oligo, and Chol modified RNA Oligo, all of which target a Luc sequence. In addition, siScr, Oligo Scr, and Chol Oligo Scr indicate, respectively, siRNA, unmodified RNA Oligo, and Chol modified RNA Oligo, which are not homologous to a Glue sequence. In experiments regarding transfection into the cultured cells, as shown in FIGS. 2 and 7, oligo was used in a concentration of 8 nM. However, in such a concentration, the expression of an endogenous gene was not decreased. Unless it was used in a high concentration that was 1,000 times higher than siRNA, a decrease in the expression of an endogenous gene was not observed. From these results, the influence of the oligo on the endogenous gene seemed to be extremely small. As shown in FIG. 10, it was confirmed that RNA oligomers having the same sequence as the antisense strand siRNA and RNA oligomers having other sequences did not knockdown the endogenous gene, in comparison to siRNA. From the aforementioned results, it was confirmed that the RNA oligomer functionalizes the mRNA without inhibiting endogenous genes.

Example 1-13: Studies with PEG-PLys

PEG-PLys was synthesized according to the previous report (K. Osada et al., *Biomaterials* 33, 325-332, (2012)) (Scheme 3). The synthetic scheme is as follows.

400 mg of MeO-PEG-NH$_2$ was dissolved in benzene, and was then freeze-dried overnight. After completion of the freeze-drying, MeO-PEG-NH$_2$ and NCA-Lys (TFA) were completely dissolved in a 0.5 M dimethylformamide (DMF) solvent under Ar atmosphere. The NCA-Lys (TFA) solution was added to the MeO-PEG-NH$_2$ solution, and the mixed solution was then stirred at 25° C. for 3 days. Thereafter, the reaction solution was re-precipitated in a mixed solution of n-hexane/ethyl acetate (3:2), so as to recover PEG-PLys (TFA). Thereafter, the recovered PEG-PLys (TFA) was vacuum-dried to obtain white powders. Thereafter, the resultant was allowed to react in a methanol mixed solvent containing 0.1 N NaOH at 35° C. for 6 hours, so as to deprotect the TFA groups. After completion of purification by dialysis, PEG-PLys was obtained in the form of white powders. According to 1H-NMR analysis, the polymerization degree of PLys in the recovered PEG-PLys was found to be 69.

In the present Example, the Glue mRNA prepared in Example 1-2, or the Glue mRNA prepared in Example 1-3 hybridizing with each of the following RNA oligomers was used.

Chol-overhang 2base (1)
Chol-overhang 2base (2)
Chol-overhang 2base (3)
Chol-overhang 2base (4)
Chol-overhang 2base (5)

Upon production of PMs, PEG-PLys and mRNA were each independently dissolved in a 10 mM HEPES buffer (pH 7.4). The concentration of the PEG-PLys was adjusted, so that the ((positive charge number of PLys)/(negative charge number of mRNA)) (N$^+$/P$^-$ ratio) became 2 at pH 7.4. The PEG-PLys solution was added to the mRNA solution, so that the final concentration of the mRNA became 33.3 μg/mL, thereby preparing PMs.

The synthesized PEG-PLys was used to perform gel electrophoresis in the same manner as that for the PEG-PAsp(DET)-Chol in Example 1-7. In addition, a luciferase Scheme 3

[Formula 3]

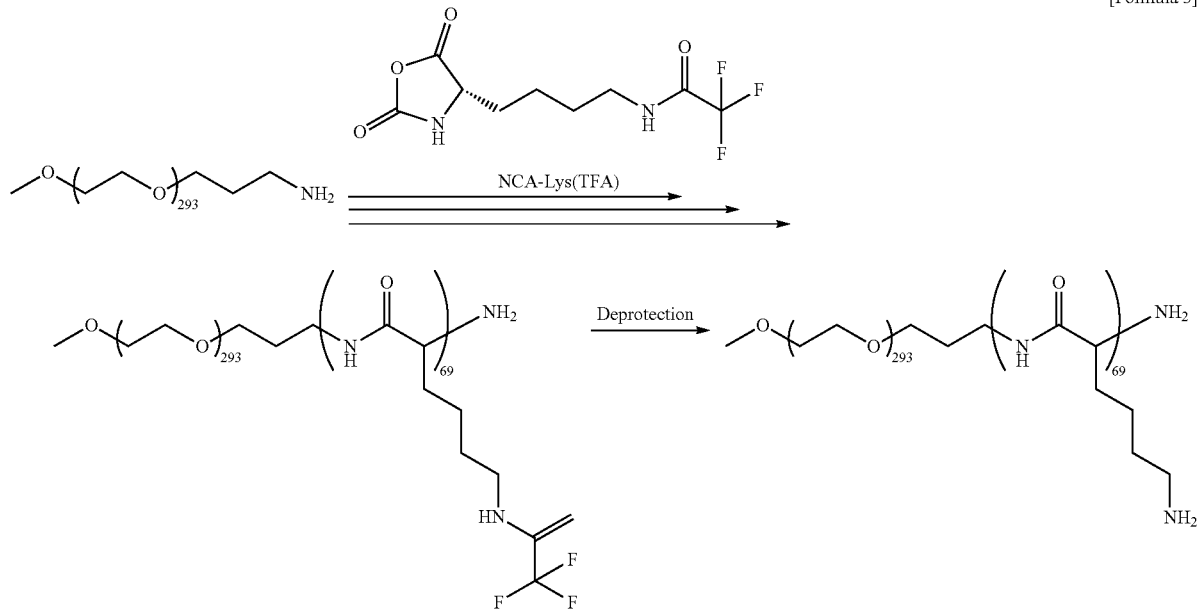

expression test was carried out in the same manner as that for the PEG-PAsp(DET)-Chol in Example 1-9.

In the experiment of performing gel electrophoresis, an mRNA hybridizing with a Chol modified oligomer at a single site was used, and in the luciferase expression experiment, an mRNA hybridizing with a Chol modified oligomer(s) at 1 or 5 sites was used. At this time, in the experiment using a single Chol modified oligomer (Chol oligo X1), Chol-overhang 2base (1) was used. On the other hand, in the experiment using five Chol modified oligomers (Chol oligo X5), Chol-overhang 2base (1) to (5) were used.

The results are shown in FIG. 11. As with the PMs consisting of PEG-PAsp(DET) or PEG-PAsp(DET)-Chol (FIG. 5), also in the case of PMs consisting of PEG-PLys, the release of the mRNA upon addition of polyanion was suppressed by adding the Chol-RNA oligomer (Chol-overhang 2base (1)) (FIG. 11(B)), and the efficiency of the expression of a protein from the mRNA was improved upon introduction thereof into the cells (FIG. 11(C)). In contrast, in a case where the Chol-RNA oligomer was not used, the release of a large amount of mRNA from the micelles was observed at an A/P ratio from 1.5 to 2 (FIG. 11(A)). Accordingly, it became clear that hybridization with Chol modified oligo is effective for the stabilization of polycations having various compositions.

Example 1-14: Blood Stability Test Using Mice

In the present Example, the Gluc mRNA prepared in Example 1-2, or the Gluc mRNA prepared in Example 1-3 hybridizing with each of the following RNA oligomers was used.
Chol-overhang 2base (1)
Chol-overhang 2base (2)
Chol-overhang 2base (3)
Chol-overhang 2base (4)
Chol-overhang 2base (5)
Chol-overhang 2base (6)
Chol-overhang 2base (7)
Chol-overhang 2base (8)
Chol-overhang 2base (9)
Chol-overhang 2base (10)

The PEG-PAsp(DET)-Chol and the mRNA were each independently dissolved in a 10 mM HEPES buffer (pH 7.4). The concentration of the PEG-PAsp(DET)-Chol was adjusted, so that the ((positive charge number of PAsp(DET))/(negative charge number of mRNA)) ($N^+/P^-$ ratio) became 1.5 at pH 7.4. The PEG-PAsp(DET)-Chol solution was added to the mRNA solution, so that the final concentration of the mRNA became 200 µg/mL, thereby preparing PMs.

The PMs solution (200 µL) comprising 40 µg of the mRNA was administered to Balb/C mice (female, 6 weeks old) through the caudal vein thereof. Then, 2.5, 5 and 10 minutes after the administration, 2 µL of blood was collected from the caudal vein. Thereafter, mRNA was extracted from the collected blood, using RNeasy Mini Kit (QIAGEN), and the extracted mRNA was then reverse-transcribed to cDNA. After that, the amount of remaining cDNA was quantified and evaluated according to qRT-PCR. The statistical treatment was carried out according to a Student's t test.

Figure 12:
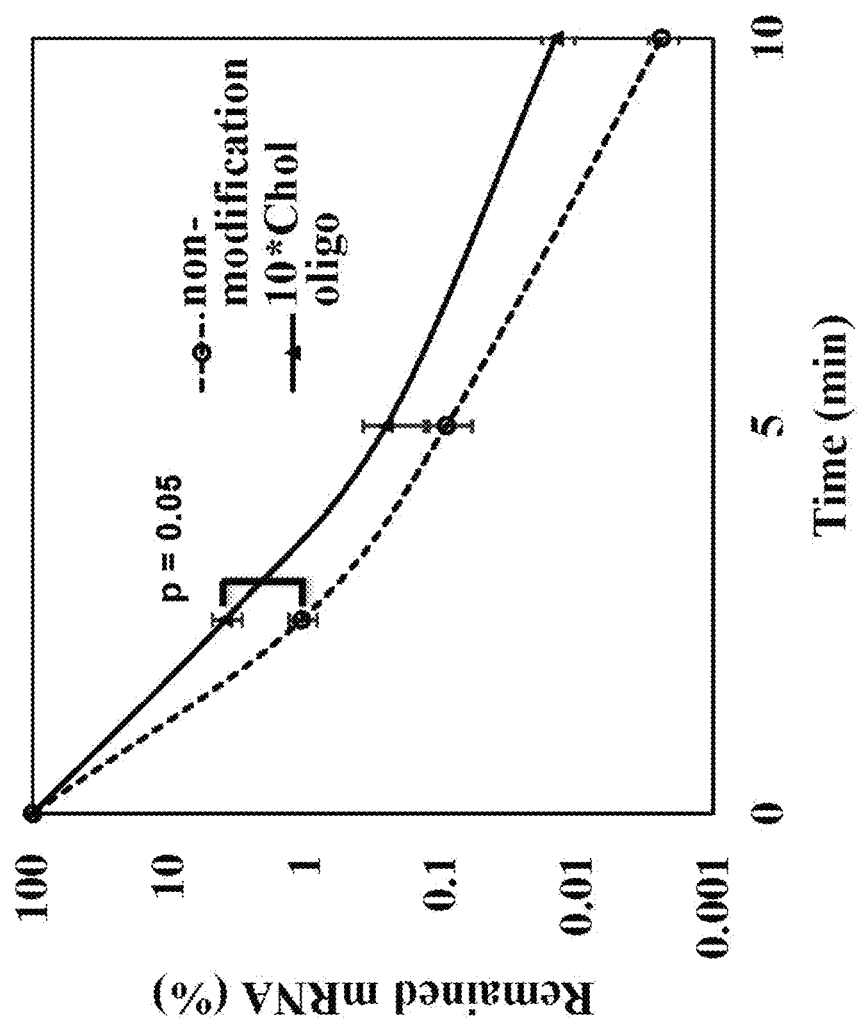
FIG. 12 is a view showing the results of a blood stability test using mice.

The results are shown in FIG. 12. As shown in FIG. 12, the blood retentivity of the mRNA tended to be improved by allowing 10 Chol modified oligomers to hybridize with the mRNA.

Example 1-15: Local Administration of PMs to Mouse Lung

In the present Example, the Gluc mRNA prepared in Example 1-2, or the Gluc mRNA prepared in Example 1-3 hybridizing with each of the following RNA oligomers was used.
Chol-overhang 2base (1)
Chol-overhang 2base (2)
Chol-overhang 2base (3)
Chol-overhang 2base (4)
Chol-overhang 2base (5)

Individual PMs were prepared under the same conditions as those in Example 5, using PEG-PAsp(DET)-Chol.

The trachea of a Balb/C mouse (female, 6 weeks old) was excised, and 50 µL of the PMs solution comprising 1.67 µg of the mRNA was directly administered into the lung using a sprayer. Twenty-four hours after the administration, the lung of the mouse was extirpated and was then homogenized, and the amount of a Gluc protein contained in the homogenate was then quantified using a luminometer. Moreover, for the purpose of quantifying the Gluc mRNA remaining in the lung, the lung 4 hours after the administration was used, and mRNA was extracted using RNeasy Mini Kit (QIAGEN). The extracted RNA was reverse-transcribed to cDNA, and the amount of the remaining cDNA was quantified and evaluated according to qRT-PCR. At this time, the expression level of the mRNA was standardized based on the amount of actin contained in the tissues.

The results are shown in FIG. 13. As shown in FIG. 13(A), significantly high efficiency of the expression of a protein from the mRNA was obtained in the mRNA hybridizing with five Chol modified oligomers, in comparison to the non-hybridizing mRNA. In addition, as shown in FIG. 13(B), the amount of the mRNA remaining without degradation in lung tissues was significantly increased by hybridization with the five Chol modified oligomers, and thus, it became clear that the stability of the mRNA in a living body was improved. Moreover, regarding safety, a significant difference was not found between the non-hybridizing mRNA and the mRNA hybridizing with the five Chol modified oligomers, in terms of the expression level of (c) interferon β and (d) interleukin 6 in the lung tissues after completion of the administration, and it remained at a low value. Thus, it was considered that the safety was guaranteed.

In view of the foregoing, it was found that improved safety (FIG. 13(B)) results in the improvement of the expression (FIG. 13(A)). From these results, it is found that the present mRNA is effective even in vivo.

Example 1-15: Production of Polyethylene Glycolated (PEGylated) mRNA

A PEGylated mRNA was produced as follows. Using RNA secondary structure prediction software (http://rtips.dna.bio.keio.ac.jp/ipknot/), the secondary structure of a Gluc mRNA was predicted, and an RNA oligomer was designed with respect to a portion of the RNA strand, which did not have a secondary structure. The present inventors asked GeneDesign, Inc. to synthesize the RNA oligomer, including PEG modification on the 5'-terminus. Herein, linear PEG having a weight average molecular weight of 12,000 was used. Then, the following RNA oligomers each having a PEG-modified 5'-terminus were purchased from GeneDesign, Inc.

```
Sequence p1 (SEQ ID NO: 34):
5'-PEG-ACUCUUUGUCGCCUUCG-3'

Sequence p2 (SEQ ID NO: 35):
5'-PEG-CUCGGCCACAGCGAUGC-3'

Sequence p3 (SEQ ID NO: 36):
5'-PEG-UCUUUGAGCACCUCCAG-3'

Sequence p4 (SEQ ID NO: 37):
5'-PEG-CUCUAGAUGCAUGCUCG-3'

Sequence p5 (SEQ ID NO: 38):
5'-PEG-GCGGCAGCCACUUCUUG-3'

Sequence p6 (SEQ ID NO: 39):
5'-PEG-AUCUCAGGAAUGUCGAC-3'

Sequence p7 (SEQ ID NO: 40):
5'-PEG-GCAGCCAGCUUUCCGGG-3'

Sequence p8 (SEQ ID NO: 41):
5'-PEG-UUGAGGCAGCCAGUUGU-3'

Sequence p9 (SEQ ID NO: 42):
5'-PEG-UGAUCUUGUCCACCUGG-3'

Sequence p10 (SEQ ID NO: 43):
5'-PEG-GAUGAACUUCUUCAUCU-3'

Sequence p11 (SEQ ID NO: 44):
5'-PEG-GUGGGACAGGCAGAUCA-3'

Sequence p12 (SEQ ID NO: 45):
5'-PEG-UUGAAGUCUUCGUUGUU-3'

Sequence p13 (SEQ ID NO: 46):
5'-PEG-GGGCAACUUCCCGCGGU-3'

Sequence p14 (SEQ ID NO: 47):
5'-PEG-CUGCUCCAUGGGCUCCA-3'

Sequence p15 (SEQ ID NO: 48):
5'-PEG-CUUGCUGGCAAAGGUCG-3'
```

In the following Examples 1-16 to 1-18, the mRNA prepared in Example 1-3 was used. The RNA oligomer in an amount of 1 equivalent of the mRNA was added to the mRNA, and the mixture was heated at 65° C. for 5 minutes, and was then cooled to 30° C. over 10 minutes, so as to perform hybridization. Thereby, a PEGylated mRNA was produced.

Example 1-16: Change in Translation Efficiency of mRNA by Hybridization of PEG-Modified RNA Oligomer with mRNA An mRNA hybridizing with a PEG-modified RNA oligomer(s) at 1, 5, 10, or 15 sites thereof was used. It is to be noted that, in individual experiments using 1, 5, 10, and 15 PEG-modified RNA oligomers, the following PEG-modified RNA oligomers produced in Example 1-15 were used, respectively.
Experiment using one PEG-modified RNA oligomer: Sequence p1
Experiment using 5 PEG-modified RNA oligomers: Sequences p1 to p5
Experiment using 10 PEG-modified RNA oligomers: Sequences p1 to p10
Experiment using 15 PEG-modified RNA oligomers: Sequences p1 to p15
Moreover, in the experiment without using such PEG-modified RNA oligomers, only the mRNA was heated at 65° C. for 5 minutes, and was then cooled to 30° C. over 10 minutes, and it was then used.

The experiments were each carried out three times.

The protein translation efficiency of the prepared mRNA samples in a cell-free system was evaluated using Rabbit Reticulocyte Lysate System, Nuclease treated (Promega Co., Madison, Wis.). A sample solution containing 300 ng of GLuc mRNA was added to a Rabbit reticulocyte lysate, and the obtained mixture was then incubated at 30° C. for 90 minutes. Thereafter, the luminescent intensity of 10 μL of the reaction solution was quantified using Renilla Luciferase assay kit (Promega). For the measurement, Mithras LB 940 (Berthold technologies Co.) was used.

Figure 18:
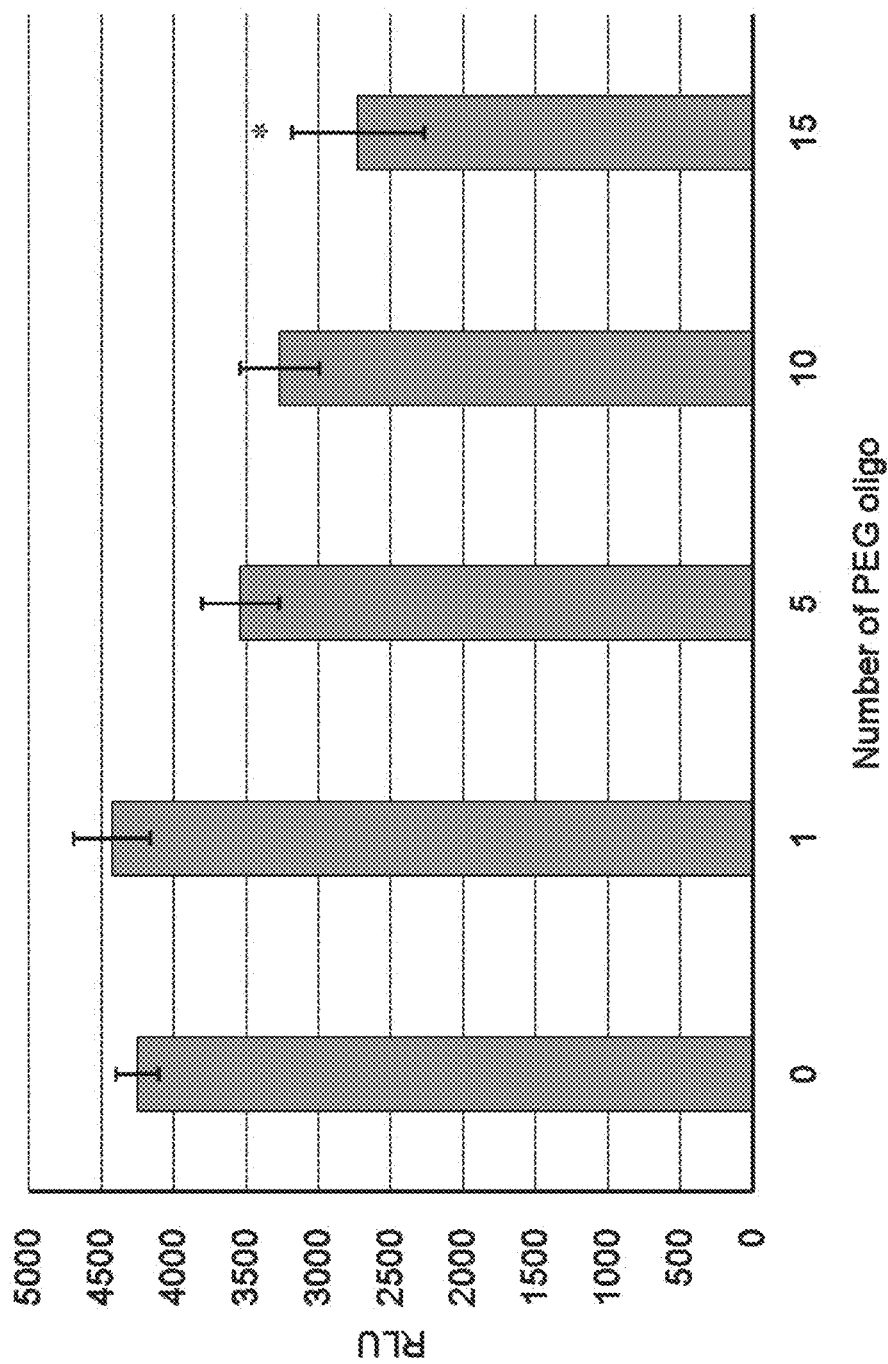
FIG. 18 is a view showing a change in translation efficiency caused by hybridization of a PEG-modified RNA oligomer with an mRNA.

The results are shown in FIG. 18. A decrease in the translation activity was slightly observed, as the amount of PEG increased. However, even though the mRNA was modified with 15 PEG-modified RNA oligomers, a translation activity of approximately 64% was obtained in comparison to an unmodified mRNA.

Herein, in FIG. 18, "*" indicates that there is a statistically significant difference of $p<0.05$, when compared with an mRNA that has not been subjected to oligo modification. For the statistical analyses, after completion of an ANOVA test, a Dunnett's test was carried out using, as a control, the mRNA that had not been subjected to oligo modification.

Example 1-17: Stabilizing Effects Obtained by Hybridization f PEG-Modified RNA Oligomer(s) with mRNA An mRNA hybridizing with a PEG-modified RNA oligomer(s) at 1, 5, 10, or 15 sites thereof was used. It is to be noted that, in individual experiments using 1, 5, 10, and 15 PEG-modified RNA oligomers, the following PEG-modified RNA oligomers produced in Example 1-15 were used, respectively.
Experiment using one PEG-modified RNA oligomer: Sequence p1
Experiment using 5 PEG-modified RNA oligomers: Sequences p1 to p5
Experiment using 10 PEG-modified RNA oligomers: Sequences p1 to p10
Experiment using 15 PEG-modified RNA oligomers: Sequences p1 to p15
Moreover, in the experiment without using such PEG-modified RNA oligomers, only the mRNA was heated at 65° C. for 5 minutes, and was then cooled to 30° C. over 10 minutes, and it was then used.

The experiments were each carried out three times.

Figure 19:
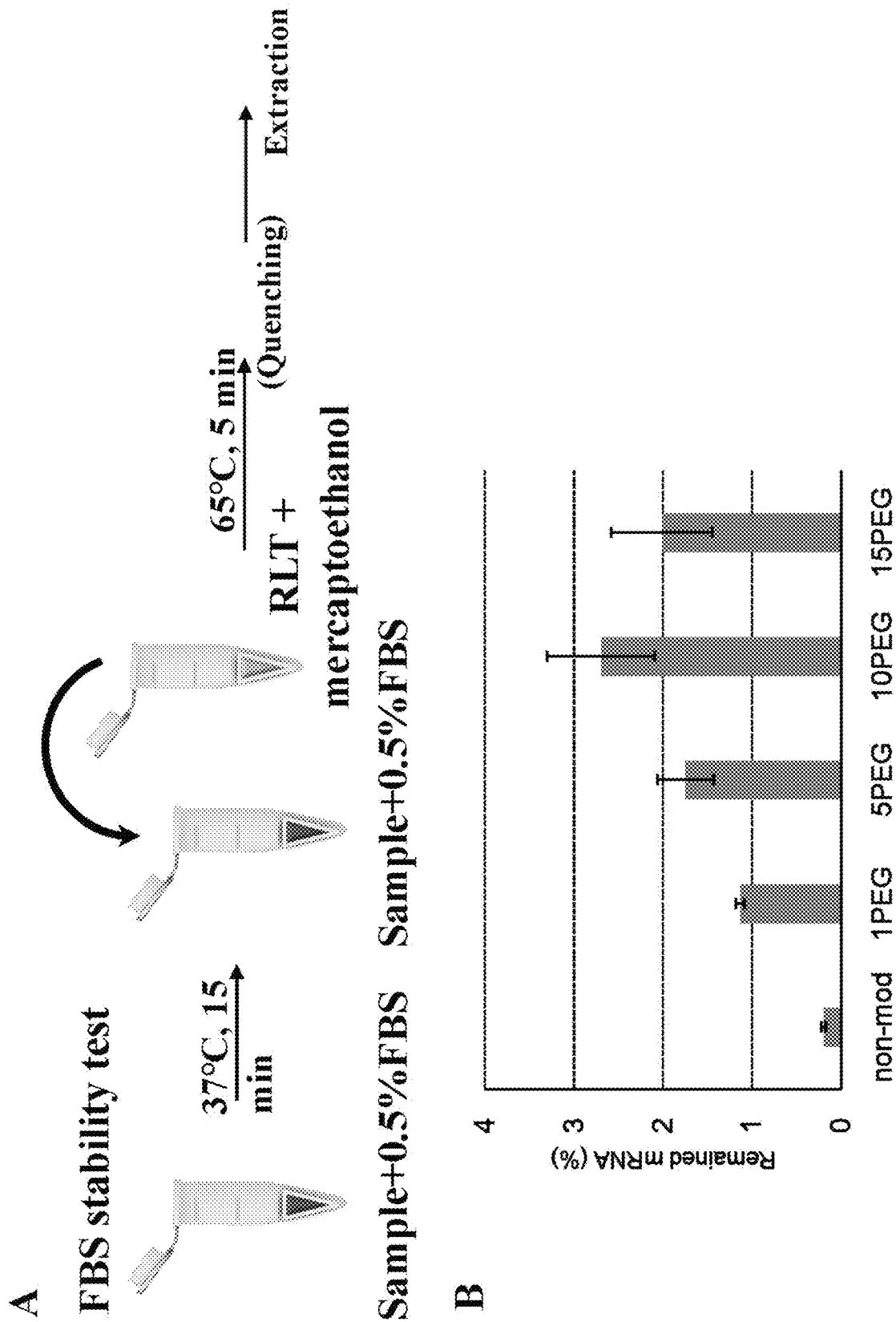
FIG. 19 is a view showing a change in stabilization effects caused by hybridization of a PEG-modified RNA oligomer with an mRNA. (A) Experimental procedures, and (B) influence on stability.

Procedures for the test of confirming stability to FBS are as shown in FIG. 19(A). A sample containing 100 ng of GLuc mRNA was incubated in a 0.5% Fetal Bovine Serum (FBS, Dainippon Sumitomo Pharma Co., Ltd., Osaka, Japan) solution at 37° C. for 15 minutes. Thereafter, 350 μL of an RLT buffer (Qiagen, Hilden, Germany) containing 1% (v/v) 2-mercaptoethanol was added to the reaction solution. The obtained mixture was incubated at 65° C. for 5 minutes, and was then placed on ice for rapid cooling, so as to denature PEG-RNA oligomers. The mRNA was purified using RNeasy Mini Kit (Qiagen), and was then reverse transcribed to complementary DNA (cDNA) using ReverTra Ace (trade name) qPCR RT Master Mix with gDNA Remover (TOYOBO CO., Ltd., Osaka, Japan). The reverse-transcribed cDNA was quantified and evaluated according to quantitative RT-PCR (qRT-PCR). Herein, for the qRT-PCR measurement, the primers having the following sequences were used.

```
Forward (SEQ ID NO: 49):
TGAGATTCCTGGGTTCAAGG

Reverse (SEQ ID NO: 50):
GTCAGAACACTGCACGTTGG
```

The results are shown in FIG. 19(B). It was suggested that the resistance to RNA-degrading enzyme be improved by using a PEG-modified oligomer(s). In addition, such resistance to RNA-degrading enzyme tended to be improved, as the number of PEG-modified oligomers increased.

Example 1-18: PEGylated mRNA Expression Test

An mRNA hybridizing with PEG-modified RNA oligomers at 15 sites thereof was used. It is to be noted that, in the experiments using 15 PEG-modified RNA oligomers, the following PEG-modified RNA oligomers produced in Example 1-15 were used.
Experiment Using 15 PEG-Modified RNA Oligomers: Sequences p1 to p15

Moreover, in the experiment without using such PEG-modified RNA oligomers, only the mRNA was heated at 65° C. for 5 minutes, and was then cooled to 30° C. over 10 minutes, and it was then used.

The experiments were each carried out three times.

An mRNA expression test was carried out in cultured cells (HuH-7 cells) as follows. Human hepatoma cells (HuH-7 cells) were seeded at a cell density of 5,000 cells/well on a 96-well plate, and were then incubated under a humidified atmosphere with 5% $CO_2$ at 37° C. for 24 hours. After the serum medium was removed, it was replaced with 100 μL of a serum-free medium (Opti-MEM, Thermo Fisher Scientific Inc., Waltham, Mass.), and a sample solution containing 250 ng of Gluc mRNA was then added thereto. Four hours later, using Renilla Luciferase assay kit (Promega), the luminescent intensity in 10 μL of a supernatant was quantified. For the measurement, Mithras LB 940 (Berthold technologies Co.) was used.

Figure 20:
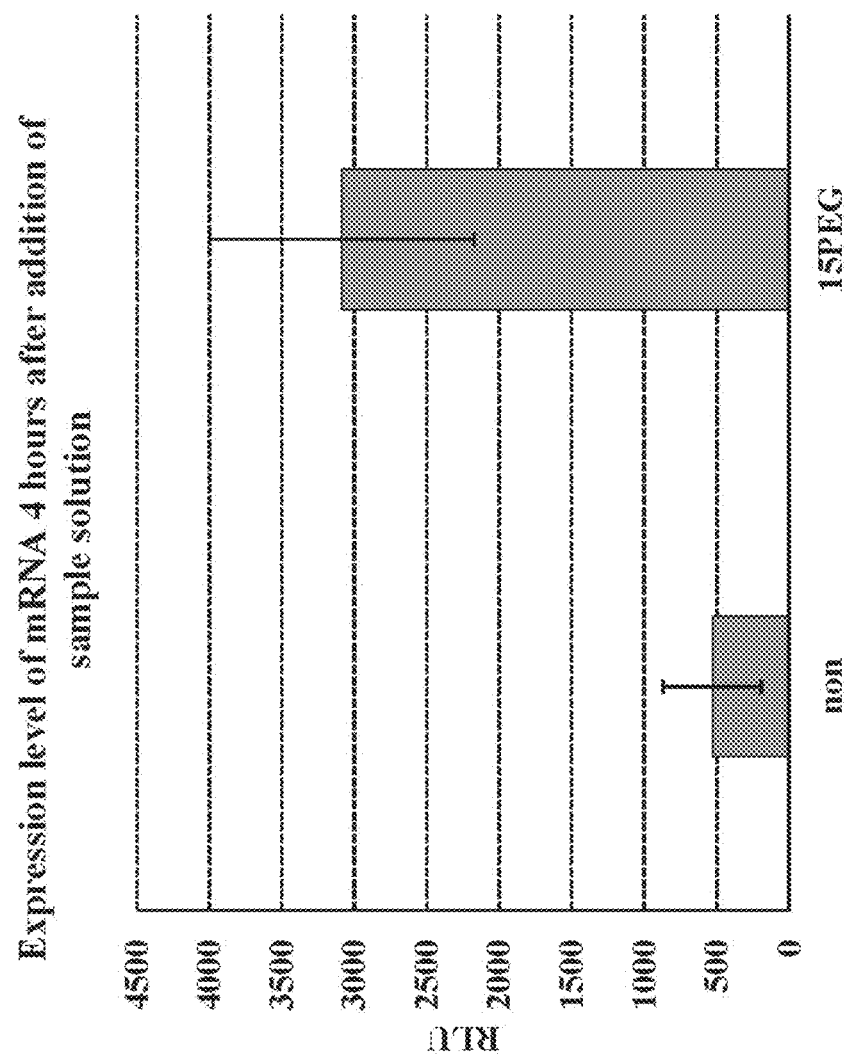
FIG. 20 is a view showing the results of a PEGylated mRNA expression test.

The results are shown in FIG. 20. The PEG-modified mRNA was significantly highly expressed in the cultured cells, in comparison to an unmodified mRNA. It is considered that this is because of the stabilizing effects of the PEG-modified mRNA.

Example 2-1: Production of Various Double-Stranded RNAs

A T7-Gluc plasmid was produced by inserting a Glue coding sequence (SEQ ID NO: 57 and FIG. 33) from a pCMV-Gluc control plasmid (New England BioLabs, Ipswich, Mass., USA) into the HindIII-XbaI site of a pSP73 vector (Promega).

A T7-Gluc poly A120 plasmid was produced by inserting A120- (BsmBI cleavage site) into the EcoR1-Bgl2 site of the T7-Gluc plasmid.

Figure 21:
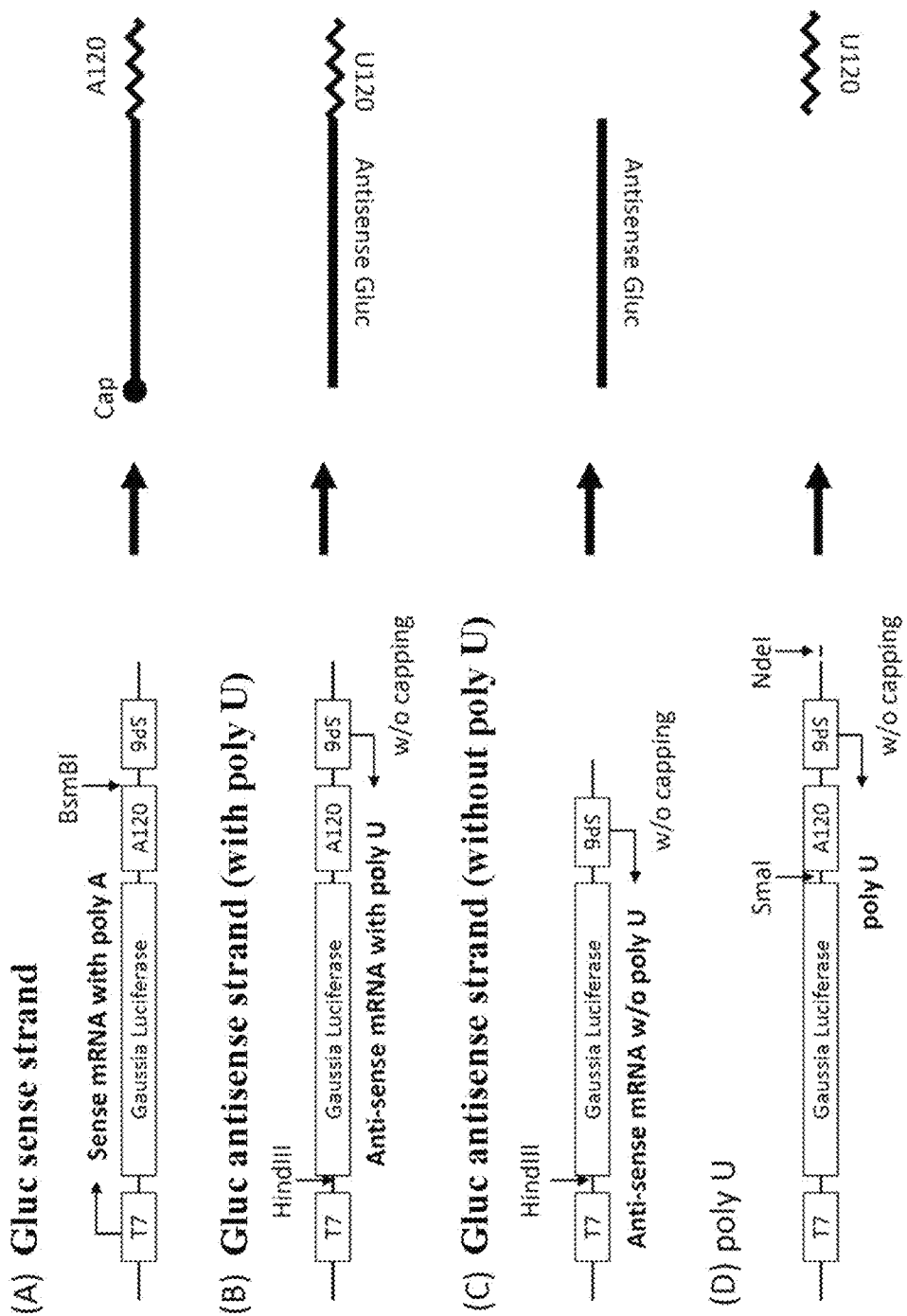
FIG. 21 is a view showing the sense strand and antisense strand of Gaussia luciferase (Glue or Luc) mRNA. (A) Glue sense strand, (B) Glue antisense strand (with poly U), (C) Glue antisense strand (without poly U), and (D) poly U.

As shown in FIG. 21(A), a Gluc sense strand was produced by cleaving the T7-Gluc poly A120 plasmid with BsmBI, and then transcribing RNA from a T7 promoter, using mMESSAGE mMACHINE T7 Ultra Kit (Thermo Fisher Scientific). When the RNA was produced using this kit, the 5'-terminus thereof is modified with Cap.

As shown in FIG. 21(B), a Gluc antisense strand (with poly U) was produced by cleaving the T7-Gluc poly A120 plasmid with HindIII, and then transcribing RNA from a Sp6 promoter, using MEGAscript (registered trademark) SP6 Transcription Kit (Thermo Fisher Scientific). Herein, since the RNA was produced without addition of a Cap analog, the 5'-terminus thereof is not modified with Cap, but is bound to a triphosphoric acid group.

As shown in FIG. 21(C), a Glue antisense strand (without poly U) was produced by cleaving the T7-Gluc plasmid with HindIII, and then transcribing RNA from a Sp6 promoter, using MEGAscript (registered trademark) SP6 Transcription Kit (Thermo Fisher Scientific).

As shown in FIG. 21(D), poly U was produced by cleaving the T7-Gluc poly A120 plasmid with SmaI, and then transcribing RNA from a Sp6 promoter, using MEGAscript (registered trademark) SP6 Transcription Kit (Thermo Fisher Scientific). Such poly U comprises a sequence (120 nucleotides) complementary to the entire poly A sequence, and a sequence (19 nucleotides) complementary to a part of the 3' UTR of the mRNA (i.e., a sequence with a nucleotide length of approximately 37% of the 3' UTR) located downstream of the sequence of 120 nucleotides. In addition, such poly U further comprises, as other sequences (17 nucleotides), a sequence in the SP6 promoter and a restriction enzyme sequence used in cloning, upstream thereof. That is to say, the poly U used herein has a sequence with a length consisting of 156 nucleotides. Moreover, the poly U has a triphosphoric acid structure at the 5'-terminus thereof.

The nucleotide sequences of the produced sense strand, antisense strand, and poly U are shown below.
Glue sense strand (SEQ ID NO: 51 and FIG. 27)
Glue antisense strand (with poly U) (SEQ ID NO: 52 and FIG. 28)
Glue antisense strand (without poly U) (SEQ ID NO: 53 and FIG. 29)
poly U (SEQ ID NO: 54 and FIG. 30)

Herein, in the sequence shown in FIG. 27, the underlined portion indicates an open reading frame (ORF), 5' UTR (with a length of 54 nucleotides) is present upstream of the ORF, 3' UTR (with a length of 52 nucleotides) is present downstream of the ORF, and 119A located further downstream thereof is a poly A sequence.

Herein, regarding the number of Poly A, theoretically, an mRNA, which is incorporated into 120 bp of the template DNA and is transcribed from the T7 promoter, has 119 nucleotides of A, whereas, an RNA, which is transcribed from the Sp6 promoter, has 120 nucleotides of U. However, the number of Poly A may be increased or decreased at the stage of DNA amplification or preparation of the mRNA.

Using the produced sense strand, antisense strand, and poly U, a double-stranded RNA was produced as follows. First, a 10 mM Hepes buffer, which comprised an equimolar amount of the sense strand, antisense strand or poly U, and has an RNA concentration of 300 μg/ml, was prepared. This solution was kept at 65° C. for 5 minutes, and was then cooled to 30° C. over 10 minutes, so as to perform hybridization.

Upon elimination of triphosphorylation, Antarctic phosphatase (New England Biolabs, cat. no. M0289S) was used.

Figure 22:
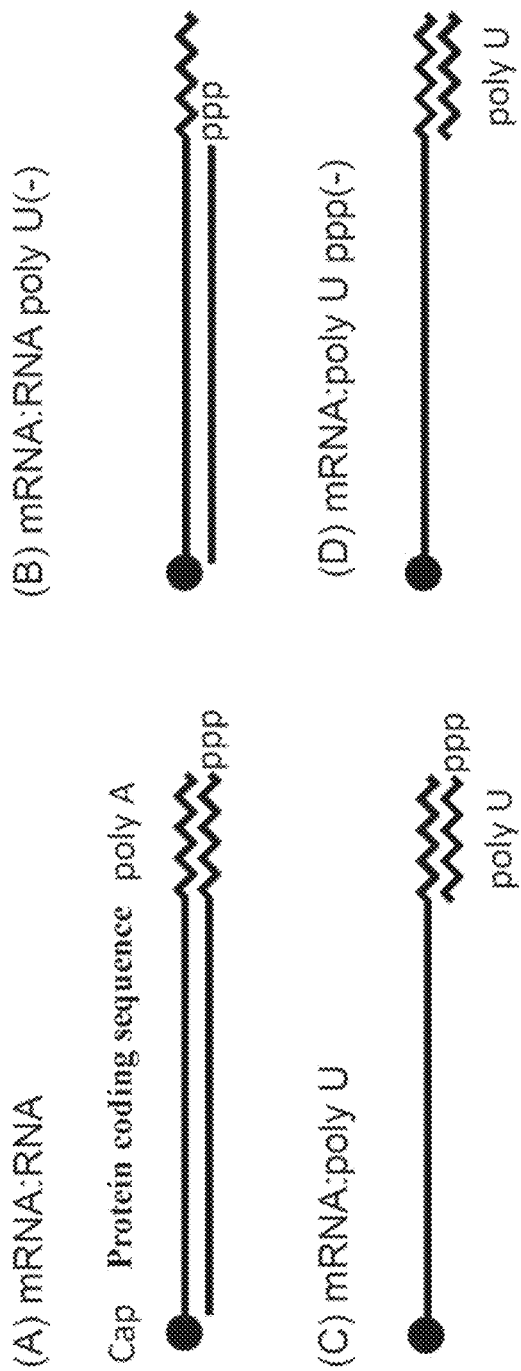
FIG. 22 is a view showing double-stranded RNAs. (A) mRNA:RNA, (B) mRNA:RNA poly U(-), (C) mRNA:poly U, and (D) mRNA:poly U ppp(-).

Herein, FIG. 22 is a schematic view showing the produced double-stranded RNA. FIG. 22(A) shows mRNA: RNA, FIG. 22(B) shows mRNA: RNA poly U(−), FIG. 22(C) shows mRNA: poly U, and FIG. 22(D) shows mRNA: poly U ppp(−).

Besides, in FIG. 22, 5' UTR is present upstream of the protein coding sequence of the mRNA, and 3' UTR is present downstream thereof.

Example 2-2: Optimization of Double-Stranded RNA Vaccine Using Dendritic Cell Line DC2.4 cells were seeded on a 6-well plate at a cell density of 1,000,000 cells/well, and 24 hours later, the medium was exchanged with a fresh one. That is, the medium was replaced with the serum-free medium Opti-MEM (trade name) (Thermo Fisher Scientific), and thereafter, using Lipofectamine (trade name) LTX (Thermo Fisher Scientific), an mRNA was administered thereto in an amount of 2.5 µg/well. Four hours after the administration, using RNeasy mini kit (QIAGEN), RNA was purified from the cells, and then, using ReverTra Ace qPCR RT Master Mix (TOYOBO), the RNA was converted to complementary DNA (cDNA). Thereafter, using Taqman gene expression assay (Applied Biosystems), the expression level of interferon β was examined. At this time, the obtained expression level was standardized based on the expression level of actin b. Moreover, the amount of a Glue protein contained in the medium was quantified using Renilla Luciferase Assay System (Promega).

Figure 23:
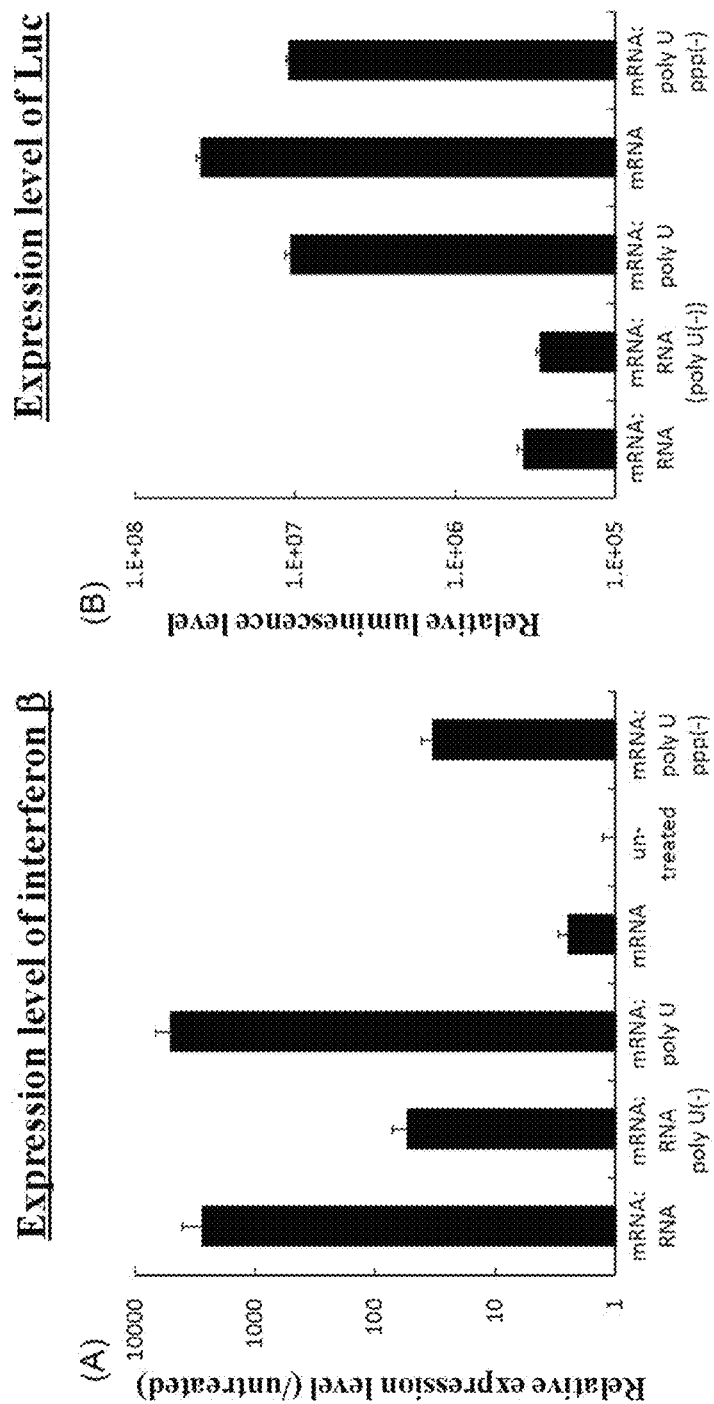
FIG. 23 is a view showing the results of introduction of a double-stranded RNA into a dendritic cell line (DC2.4). (A) The expression level of interferon β, and (B) the expression level of Luc.

The results are shown in FIG. 23. In the case of the mRNA: RNA involving full length hybridization, a strong inflammatory response could be provoked (FIG. 23(A)), but the expression level of the Gluc protein from the mRNA was decreased by approximately 100 times, in comparison to a single-stranded mRNA (FIG. 23(B)). On the other hand, in the case of the mRNA: RNA poly U(−), the inflammatory response was significantly decreased in comparison to the mRNA: RNA (FIG. 23(A)), and also, the expression level of Gluc was at the same level as that of the mRNA: RNA (FIG. 23(B)). In contrast, in the case of an mRNA hybridizing only with the poly U portion, a strong inflammatory response that was equivalent to that of the mRNA: RNA was observed (FIG. 23(A)), and the expression level of the protein from the mRNA was also kept at the same level as that of the single-stranded mRNA (FIG. 23(B)). Herein, the 5'-terminus of the antisense strand RNA was in a triphosphorylated state. It has been known that this is recognized by the intracellular nucleic acid receptor RIG-I and provokes a strong inflammatory response. Hence, in order to examine the relationship between triphosphoric acid and inflammatory response, an mRNA hybridizing with poly U excluding triphosphoric acid was introduced. As a result, the inflammatory response was decreased to some extent in comparison to the case of triphosphorylated poly U. Therefore, it became clear that when the RNA oligomer has triphosphoric acid at the 5'-terminus, it provokes a stronger inflammatory response.

Since inflammation hardly occurred in the mRNA: RNA poly U(−), it is strongly suggested that recognition of triphosphoric acid by RIG-I be different depending on the type of a complementary strand used. In the case of poly U, it is considered: that its 5'-terminus is exposed to the terminus of the mRNA, and thus, triphosphoric acid is likely to become three-dimensionally easily recognizable by RIG-I; and also that the sequence around triphosphoric acid contains many U, but since AU bonds are weak, the motility of triphosphoric acid is increased and thus is likely to become easily recognizable. Hence, it was strongly suggested that selection of the complementary strand be important for innate immune response via RIG-I.

As such, it was found that, when a complementary strand (poly U) is allowed to mainly hybridize with a poly A strand portion to be added to the 3'-terminus of the mRNA, a strong inflammatory response is provoked, while the protein expression efficiency is hardly decreased.

Example 2-3: Intralymphatic Administration of Poly U-Hybridized mRNA mRNA:poly U was produced in the same manner as that of Example 2-2. 10 µL of a 10 mM Hepes solution containing 3 µg of Gluc mRNA was administered into the inguinal lymph node of C57BL6N mice. Four hours after the administration, the inguinal lymph node was recovered, and was then dissolved in Passive lysis buffer (Promega). Thereafter, the expression level of Luc was quantified using Renilla Luciferase Assay System (Promega). Moreover, using RNeasy mini kit (QIAGEN), RNA was extracted, and then, using ReverTra Ace qPCR RT Master Mix (TOYOBO), the RNA was converted to complementary DNA (cDNA). Thereafter, using Taqman gene expression assay (Applied Biosystems), the expression levels of interferon β and interleukin 6 were examined. At this time, the obtained expression levels were standardized based on the expression level of actin b.

Figure 24:
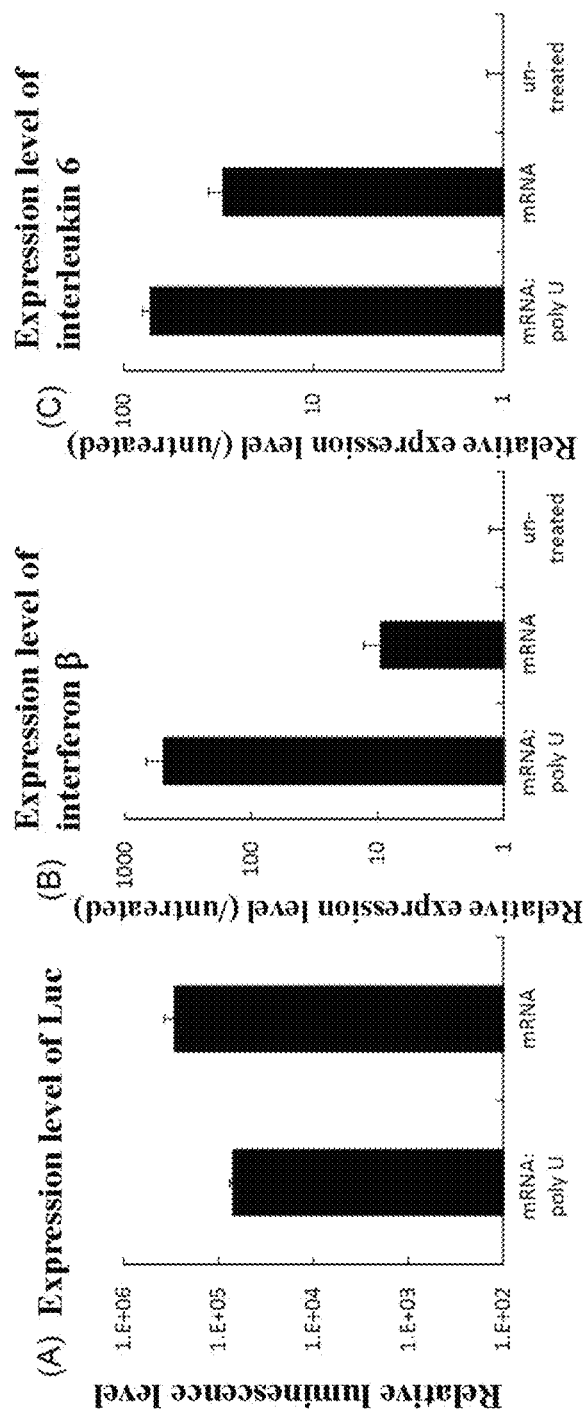
FIG. 24 is a view showing the results of administration of double-stranded RNA to mice. (A) The expression level of Luc, (B) the expression level of interferon β, and (C) the expression level of interleukin 6.

The results are shown in FIG. 24. As a result, as with the analysis using the cultured cells shown in FIG. 23, the inflammatory response was significantly improved, in comparison to a single-stranded mRNA, only by hybridization with poly U (FIGS. 24(B) and (C)), and further, the efficiency of Gluc expression from the mRNA was at almost the same level as that of the single-stranded mRNA (FIG. 24(A)).

Thus, it was found that the poly U-hybridized mRNA provokes a strong inflammatory response even in vivo, without largely impairing translation efficiency.

Example 2-4: Induction of Cellular Immunity by Poly U-Hybridized mRNA

A T7-OVA poly A120 plasmid was produced by inserting the OVA coding sequence (SEQ ID NO: 58 and FIG. 34) that had been subjected to codon optimization by Genscript into the XhoI-EcoR1 site of a pSP73 vector (Promega). An OVA sense strand was produced by cleaving the T7-OVA poly A120 plasmid with BsmBI, and then transcribing RNA from a T7 promoter, using mMESSAGE mMACHINE T7 Ultra Kit (Thermo Fisher Scientific), poly U was produced by cleaving the T7-Gluc poly A120 plasmid with EcoRI, and then transcribing RNA from a Sp6 promoter, using MEGAscript (registered trademark) SP6 Transcription Kit (Thermo Fisher Scientific).

Herein, the poly U comprises a sequence (120 nucleotides) complementary to the entire poly A sequence, and a sequence (5 nucleotides) complementary to a part of the 3' UTR of the mRNA (i.e., a sequence with a nucleotide length of approximately 83% of the 3' UTR) located downstream of the sequence of 120 nucleotides. Besides, the poly U used herein further comprises, as other sequences (17 nucleotides), a sequence in the SP6 promoter and a restriction enzyme sequence used in cloning. That is to say, the poly U used herein has a sequence with a length consisting of 142 nucleotides. Moreover, the poly U has a triphosphoric acid structure at the 5'-terminus thereof.

The nucleotide sequences of the produced sense strand and poly U are shown below.

OVA sense strand (SEQ ID NO: 55 and FIG. 31)
Poly U (SEQ ID NO: 56 and FIG. 32)

Besides, in the sequence shown in FIG. 31, the underlined portion indicates an open reading frame (ORF), 5' UTR (with a length of 16 nucleotides) is present upstream of the ORF, 3' UTR (with a length of 6 nucleotides) is present downstream of the ORF, and 119A located further downstream thereof is a poly A sequence.

Regarding the number of A or U, they are the same as those in Example 2-1. The mRNA transcribed from the T7 promoter has 119 nucleotides of A, whereas the mRNA transcribed from the Sp6 promoter has 120 nucleotides of U.

However, the number of Poly A may be increased or decreased at the stage of DNA amplification or preparation of the mRNA.

The poly U-hybridized OVA-expressing mRNA (mRNA: poly U) was produced in the same manner as that of Example 2-2. Specifically, a 10 mM Hepes buffer, which comprised an equimolar amount of the sense strand, antisense strand or poly U, and has an RNA concentration of 300 µg/ml, was prepared. This solution was kept at 65° C. for 5 minutes, and was then cooled to 30° C. over 10 minutes, so as to perform hybridization.

Procedures for the following experiment are shown in FIG. 25(A). First, 10 µL of a 10 mM Hepes solution containing 3 µg of OVA mRNA was administered into the inguinal lymph node of C57BL6N mice. Seven days later, the splenic cells were recovered, and Enzyme-Linked Inmmunospot (ELISPOT) Assay was carried out using IFN-γ ELISpot PLUS, Mouse(−)HRP kit (MABTECH). Herein, the cells were seeded at a cell density of 250,000 cells/well on a 96-well plate. The cells were cultured for 24 hours to a final OVA concentration of 10 µg/mL, and thereafter, the number of IFN-γ-producing cells was counted.

The results are shown in FIG. 25(B). The longitudinal axis of FIG. 25(B) shows the number of splenic cells that have reacted with OVA and have produced IFN-γ, and it serves as an indicator of cellular immunity. As shown in FIG. 25(B), the single-stranded OVA mRNA could hardly induce cellular immunity, whereas in the poly U-hybridized OVA mRNA (mRNA: poly U), a significant cellular immune reaction was observed.

Hence, it was found that stronger cellular immunity can be induced by poly U hybridization.

Example 2-5: Induction of Humoral Immunity by Poly U-Hybridized mRNA

The OVA mRNA was administered to C57BL6N mice by the same method as that of Example 2-4, and 7 days after the administration, blood was collected (FIG. 26(A)). Anti-OVA IgG in the serum was quantified using Mouse Anti-OVA IgG Antibody Assay Kit (Chondrex, Inc.).

The results are shown in FIG. 26(B). The OVA-reactive IgG value was not increased in the single-stranded mRNA, in comparison to a control group. In contrast, a significant increase in the IgG value was observed in the poly U-hybridized OVA mRNA (mRNA: poly U).

In view of the foregoing, it was found that stronger humoral immunity can be induced by poly U hybridization.

Example 2-6: Optimization of Double-Stranded RNA Vaccine Using Dendritic Cells The expression level of a protein from the mRNA (i.e., the expression level of luciferase) was quantified in dendritic cells (D.C.2.4 cells) by the same method as that of Example 2-2.

The experiment was carried out by seeding the D.C.2.4 cells at a cell density of 40,000 cells/well on a 96-well plate. In addition, the following three RNA oligomers were used.

Poly U (chain length of sequence complementary to 3' UTR: 5 nucleotides) (SEQ ID NO: 56, FIG. 36(B))

Poly U (chain length of sequence complementary to 3' UTR: 19 nucleotides) (SEQ ID NO: 54, FIG. 36(B))

Poly U (chain length of sequence complementary to 3' UTR: 50 nucleotides) (SEQ ID NO: 59, FIG. 36(B))

The "poly U (chain length of sequence complementary to 3' UTR: 5 nucleotides) (SEQ ID NO: 56)" was produced by cleaving the T7-Gluc poly A120 plasmid with EcoRI, and then transcribing RNA from a Sp6 promoter, using MEGAscript (registered trademark) SP6 Transcription Kit (Thermo Fisher Scientific) (FIG. 36(A)).

The "Poly U (chain length of sequence complementary to 3' UTR: 19 nucleotides) (SEQ ID NO: 54)" was produced by cleaving the T7-Gluc poly A120 plasmid with SmaI, and then transcribing RNA from a Sp6 promoter, using MEGAscript (registered trademark) SP6 Transcription Kit (Thermo Fisher Scientific) (FIG. 36(A)).

Besides, the "poly U (chain length of sequence complementary to 3' UTR: 5 nucleotides) (SEQ ID NO: 56)" comprises a sequence (5 nucleotides) complementary to a portion of the 3' UTR of the mRNA (i.e., a sequence having a nucleotide length that is approximately 10% of the 3' UTR (with a length of 52 nucleotides).

In addition, the poly U (chain length of sequence complementary to 3' UTR: 19 nucleotides) comprises a sequence (19 nucleotides) complementary to a portion of the 3' UTR of the mRNA (i.e., a sequence having a nucleotide length that is approximately 36% of the 3' UTR (with a length of 52 nucleotides).

The "poly U (chain length of sequence complementary to 3' UTR: 50 nucleotides)" was produced by cleaving the T7-Gluc poly A120 plasmid with NotI, and then transcribing RNA from a Sp6 promoter, using MEGAscript (registered trademark) SP6 Transcription Kit (Thermo Fisher Scientific) (FIG. 36(A)).

Herein, the poly U comprises a sequence (120 nucleotides) complementary to the entire poly A sequence, and a sequence (50 nucleotides) complementary to a part of the 3' UTR of the mRNA (i.e., a sequence with a nucleotide length of approximately 96% of the 3' UTR (with a length of 52 nucleotides) located downstream of the sequence of 120 nucleotides. Besides, the poly U used herein further comprises, as other sequences (17 nucleotides), a sequence in the SP6 promoter and a restriction enzyme sequence used in cloning. That is to say, the poly U used herein has a sequence with a length consisting of 187 nucleotides. Moreover, the poly U has a triphosphoric acid structure at the 5'-terminus thereof.

Figure 35:
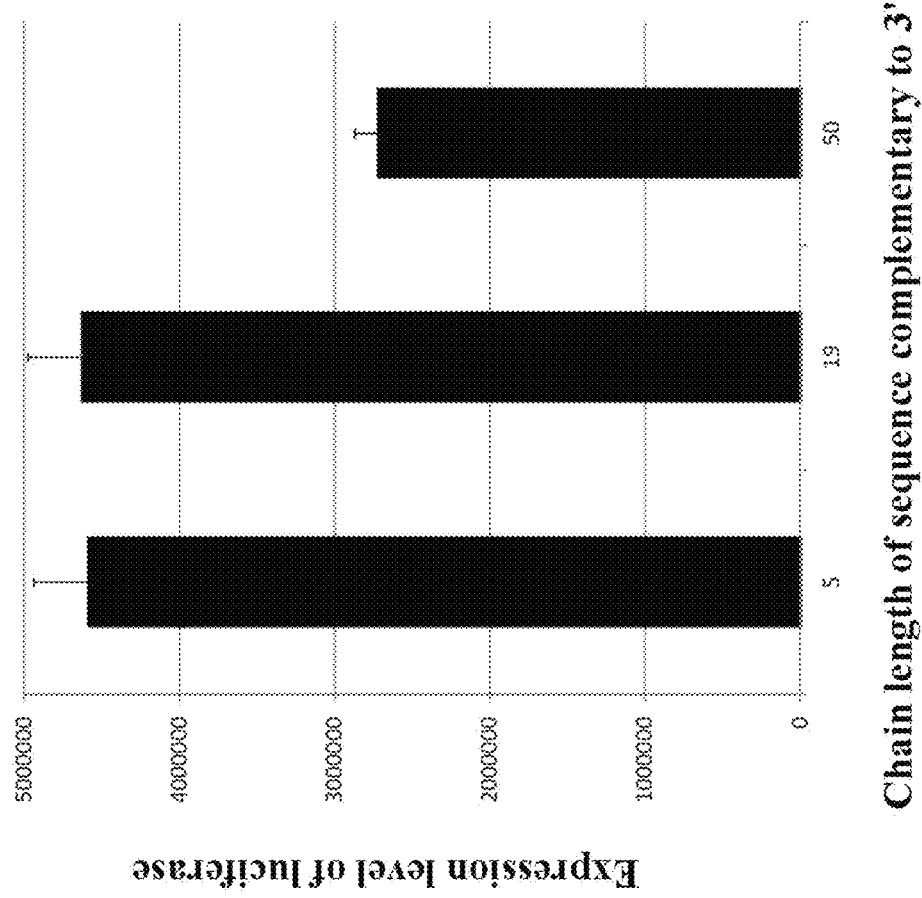
FIG. 35 is a view showing the results obtained by introducing a double-stranded RNA into a dendritic cell line (DC2.4) and then confirming the expression level of luciferase.

The results are shown in FIG. 35. As shown in FIG. 35, it is found that the shorter the chain length of the sequence complementary to the 3' UTR of each poly U, the more preferable it is for maintaining the expression of a protein from the mRNA.

Example 3-1: Hybridization with RNA Oligomer

A synthetic RNA oligomer was produced as follows. First, with regard to a first sequence complementary to a Gluc mRNA, using RNA secondary structure prediction software (http://rtips.dna.bio.keio.ac.jp/ipknot/), the secondary structure of the Gluc mRNA was predicted, and an RNA oligomer was designed with respect to a portion of the RNA strand, which did not have a secondary structure. The overhang sequence was designed using A or U, so that it did not hybridize with the mRNA strand as much as possible. With regard to a second sequence complementary to a 5' ppp-RNA oligomer, first, the sequence of the 5' ppp-RNA oligomer was designed, and the second sequence complementary to the designed sequence was then obtained. For the 5' ppp-RNA oligomer, a GU-repeat sequence was used. Using this GU-repeat sequence, in vitro transcription is performed in an ATP-free system, so that generation of by-products of the complementary strand can be suppressed. In addition, the GU-repeat sequence is characterized in that it does not form a secondary structure in the RNA itself. As a sequence complementary to this 5' ppp-RNA oligomer, the second sequence was obtained. At this time, the sequence was designed so that the triphosphorylated 5'-terminus of the 5' ppp-RNA oligomer could be blunt-ended.

The present inventors asked to a third party the synthesis of the thus designed synthetic RNA oligomers, and then, purchased the following synthetic RNA oligomers each consisting of, from the 5'-terminus, a sequence of 17 nucleotides complementary to the Gluc mRNA, an overhang sequence of 2 nucleotides, and a sequence of 24 nucleotides complementary to the 5' ppp-RNA oligomer.

The synthetic RNA oligomers were purchased from Hokkaido System Science Co., Ltd.

```
Synthetic RNA oligomer sequence 1 (SEQ ID NO: 60):
CAGCCAGCUUUCCGGGCUACACACACACACACACACACACACC Synthetic RNA oligomer sequence 2 (SEQ ID NO: 61):
ACUCUUUGUCGCCUUCGAUCACACACACACACACACACACACC Synthetic RNA oligomer sequence 3 (SEQ ID NO: 62):
GCGGCAGCCACUUCUUGUACACACACACACACACACACACACC
```

The 5' ppp-RNA oligomer was produced as follows. First, a DR274 vector (Addgene) was cleaved with BsaI, and two types of oligomers hybridizing with each other were then inserted therein.

```
DNA oligomer (SEQ ID NO: 63):
TAGGTGTGTGTGTGTGTGTGTGTGGGCCC

DNA oligomer (SEQ ID NO: 64):
AAACGGGCCCACACACACACACACACACACA
```

Thereby, the vector having the nucleotide sequence shown in FIG. 41 (SEQ ID NO: 65) was produced. Next, the 5' ppp-RNA oligomer was produced by cleaving the vector having the nucleotide sequence shown in FIG. 41 (SEQ ID NO: 65) with ApaI and SnaBI and then performing in vitro transcription. Upon the in vitro transcription, by using a reaction solution containing no ATP, transcription of the complementary strand RNA of a target sequence was suppressed. Thereby, the following 5' ppp-RNA oligomer with a triphosphorylated 5'-terminus was prepared.

```
5' ppp-RNA oligomer (SEQ ID NO: 66):
GGUGUGUGUGUGUGUGUGUGUGUG
```

It was expected that, as a result of hybridization of each of the synthetic RNA oligomer sequences 1 to 3 with the 5' ppp-RNA oligomer, a blunt 5'-terminal triphosphorylated structure could be obtained on the side at which the hybridization was carried out.

One×24 nt: The 5' ppp-RNA oligomer, the synthetic RNA oligomer sequence 1, and the Gluc mRNA were mixed with one another at a molar ratio of 1:1:1, for hybridization.

Two×24 nt: The 5' ppp-RNA oligomer, the synthetic RNA oligomer sequences 1 and 2, and the Gluc mRNA were mixed with one another at a molar ratio of 1:1:1:1, for hybridization.

Three×24 nt: The 5' ppp-RNA oligomer, the synthetic RNA oligomer sequences 1, 2 and 3, and the Gluc mRNA were mixed with one another at a molar ratio of 1:1:1:1:1, and hybridization was carried out under the following conditions.

In the following Examples 3-2 and 3-3, the Gluc mRNA prepared in Example 1-3 was used. In the hybridization, the mixed solution was heated at 65° C. for 5 minutes, and was then cooled to 30° C. over 10 minutes, so as to perform hybridization.

In addition, in Example 3-3, the "mRNA: poly U" prepared in Example 2-1 was used as "mRNA: pU."

Example 3-2: Immunostimulation

DC2.4 cells were seeded on a 12-well plate at a cell density of 400,000 cells/well, and 24 hours later, the medium was exchanged with a fresh one. That is, the medium was replaced with the serum-free medium Opti-MEM (trade name) (Thermo Fisher Scientific), and thereafter, using Lipofectamine (trade name) LTX (Thermo Fisher Scientific), an mRNA was administered thereto in an amount of 2.5 µg/well. Four hours after the administration, using RNeasy mini kit (QIAGEN), RNA was purified from the cells, and then, using ReverTra Ace qPCR RT Master Mix (TOYOBO), the RNA was converted to complementary DNA (cDNA). Thereafter, using Taqman gene expression assay (Applied Biosystems), the expression levels of interferon β and interleukin 6 were examined. At this time, the obtained expression levels were standardized based on the expression level of actin b.

The results are shown in FIG. 38 and FIG. 39. As the number of double strand structures each consisting of the 5' ppp-RNA oligomer and the synthetic RNA oligomer increased, the expression levels of interferon β and interleukin 6 were also increased. From these results, it became clear that immunostimulation effects were increased, as the number of the double strand structures increased.

Example 3-3: Protein Translation

DC2.4 cells were seeded on a 96-well plate at a cell density of 40,000 cells/well, and 24 hours later, the medium was exchanged with a fresh one. That is, the medium was replaced with the serum-free medium Opti-MEM (trade name) (Thermo Fisher Scientific), and thereafter, using Lipofectamine (trade name) LTX (Thermo Fisher Scientific), an mRNA was administered thereto in an amount of 0.25 µg/well. Four hours after the administration, the amount of a Gluc protein was quantified using Renilla Luciferase Assay System (Promega).

The results are shown in FIG. 40. As the number of double strand structures each consisting of the 5' ppp-RNA oligomer and the synthetic RNA oligomer increased, a slight decrease in the translation activity was observed. However, even in a case where the three RNA oligomers bound to the RNA, a translation activity of approximately 70% was maintained in comparison to a single-stranded RNA. When compared with the mRNA: pU as a second aspect, excellent translation activity was obtained.

Herein, the P value shown in FIGS. 38 to 40 indicates a statistically significant difference obtained after an ANOVA test was performed as a statistical treatment and a Tukey test was then carried out.

INDUSTRIAL APPLICABILITY

It has been expected that mRNA delivery will be applied to the medical field as a method of supplying a therapeutic protein into a body safely and continuously. On the other hand, such mRNA delivery has been greatly problematic in that enzymatic degradation of mRNA promptly occurs in a living body. In contrast, according to the first aspect of the present invention, the mRNA molecule itself has been chemically modified, so that enzymatic degradation of the mRNA has been significantly suppressed when the mRNA has been loaded in a polymeric micelle, and the efficiency of mRNA introduction has been successfully enhanced. The polymeric micelle loading mRNA therein, which is used herein, has exhibited excellent effects in therapeutic experiments performed on animal models suffering from various diseases such as central nervous system disease, motor sense organ disease, liver disease, and malignant tumor, and studies regarding future clinical application of the polymeric micelle have been conducted. The composition of such a polymeric micelle is different depending on a target organ and an administration method. Since the technique according to the first aspect of the present invention can stabilize micelles with various compositions, it can be applied to a wide range of field.

The mRNA vaccine is positioned as a pharmaceutical product that is based on a mechanism completely different from the mechanism of conventional vaccines. The mRNA vaccine is characterized in that an antigenic protein to be expressed can be freely constructed, and in that cellular immunity can be induced. As a similar type of nucleic acid vaccine, a DNA vaccine has been studied. However, DNA may cause the risk of inducing mutation due to random insertion into the host genome, and such risk may impair practical realization. In contrast, mRNA does not have such risk.

The development of vaccines using conventional single-stranded mRNAs has progressed mainly in U.S.A. and Germany. However, the combined use of an adjuvant has been inevitable for effectively provoking an inflammatory response. The mRNA vaccine according to the second and third aspects of the present invention does not necessarily require such an adjuvant, and the inflammatory response can be effectively provoked only by mRNA. Moreover, the mRNA can provoke the inflammatory response, simultaneously and sympatrically with antigen presentation.

The mRNA vaccine can be flexibly applied depending on intended use or purpose, regardless of administration route (subcutaneous administration, intramuscular administration, transmucosal administration, etc.), carrier, and the like. Moreover, the mRNA used in the mRNA vaccine is purified on the basis of a chemical reaction, and can be applied to all types of proteins only by modification of the nucleotide sequence thereof. Accordingly, significant cost reduction can be expected by economies of scale. These are advantages clearly different from the conventional vaccines. It is expected that the vaccine according to the second and third aspects of the present invention can be used as a novel vaccine system in a wide range of market, such as a personalized treatment for cancer and the like, and an infectious disease vaccine rapidly coping with virus mutation.

Sequence Listing Free Text
SEQ ID NOS: 1 to 27—Synthetic RNA
SEQ ID NOS: 28 to 31—Synthetic DNA/RNA
SEQ ID NO: 32—Synthetic DNA
SEQ ID NO: 33—Synthetic RNA
SEQ ID NOS: 34 to 48—Synthetic RNA
SEQ ID NOS: 49 and 50—Synthetic DNA
SEQ ID NOS: 51 to 56—Synthetic RNA
SEQ ID NOS: 57 and 58—Synthetic DNA
SEQ ID NO: 59—Synthetic RNA
SEQ ID NOS: 60 to 62—Synthetic RNA
SEQ ID NOS: 63 to 65—Synthetic DNA
SEQ ID NOS: 66 to 68—Synthetic RNA

The invention claimed is:

1. An mRNA vaccine, which comprises a double-stranded RNA consisting of an mRNA encoding an antigen, at least one first RNA oligomer hybridizing with the mRNA, and a second RNA oligomer hybridizing with the first RNA oligomer, wherein
the first RNA oligomer comprises:
   (a) an RNA sequence comprising a first RNA sequence consisting of a sequence of 12 to 40 nucleotides complementary to the sequence of the mRNA, and a second RNA sequence consisting of a sequence of 10 to 200 nucleotides complementary to the sequence of the second RNA oligomer, in this order from the 5'-terminus thereof,
   (b) an RNA sequence comprising a first RNA sequence having an identity of 90% or more to a sequence of 12 to 40 nucleotides complementary to the sequence of the mRNA and hybridizing with the mRNA, and a second RNA sequence having an identity of 90% or more to a sequence of 10 to 200 nucleotides complementary to the sequence of the second RNA oligomer and hybridizing with the second RNA oligomer, in this order from the 5'-terminus thereof,
   (c) an RNA sequence comprising a second RNA sequence consisting of a sequence of 10 to 200 nucleotides complementary to the second RNA oligomer, and a first RNA sequence consisting of a sequence of 12 to 40 nucleotides complementary to the sequence of the mRNA, in this order from the 5'-terminus thereof, or
   (d) an RNA sequence comprising a second RNA sequence having an identity of 90% or more to a sequence of 10 to 200 nucleotides complementary to the sequence of the second RNA oligomer and hybridizing with the second RNA oligomer, and a first RNA sequence having an identity of 90% or more to a sequence of 12 to 40 nucleotides complementary to the sequence of the mRNA and hybridizing with the mRNA, in this order from the 5'-terminus thereof.

2. The mRNA vaccine according to claim 1, wherein the first RNA oligomer consists of a sequence of 22 to 240 nucleotides.

3. The mRNA vaccine according to claim 1, wherein the number of the first RNA oligomers to be allowed to hybridize with one mRNA is 1 to 50.

4. The mRNA vaccine according to claim 1, wherein the first RNA oligomer comprises the RNA sequence (a) or the RNA sequence (b), and the second RNA oligomer has a triphosphoric acid structure at the 5'-terminus thereof.

5. The mRNA vaccine according to claim 1, wherein the first RNA oligomer comprises the RNA sequence (c) or the RNA sequence (d), and the first RNA oligomer has a triphosphoric acid structure at the 5'-terminus thereof.

6. The mRNA vaccine according to claim 1, wherein the terminus of the double-stranded RNA on the side at which the second RNA oligomer hybridizes with the first RNA oligomer is a blunt end.

7. The mRNA vaccine according to claim 1, wherein the second RNA oligomer comprises a sequence of 10 to 200 nucleotides.

8. The mRNA vaccine according to claim 1, wherein the double-stranded RNA is in a naked form.

9. The mRNA vaccine according to claim 1, which is not used together with an adjuvant.

10. The mRNA vaccine according to claim 1, which is for use in the prevention or treatment of a disease in a subject in need thereof.

* * * * *